(12) United States Patent
Viola et al.

(10) Patent No.: US 10,962,524 B2
(45) Date of Patent: Mar. 30, 2021

(54) CHARACTERIZATION OF BLOOD HEMOSTASIS AND OXYGEN TRANSPORT PARAMETERS

(71) Applicant: HemoSonics LLC, Charlottesville, VA (US)

(72) Inventors: Francesco Viola, Charlottesville, VA (US); William F. Walker, Charlottesville, VA (US)

(73) Assignee: HomoSonics LLC, Charlottesville, VA (US)

( * ) Notice: Subject to any disclaimer, the term of this patent is extended or adjusted under 35 U.S.C. 154(b) by 0 days.

(21) Appl. No.: 14/687,837

(22) Filed: Apr. 15, 2015

(65) Prior Publication Data

US 2016/0139080 A1 May 19, 2016

Related U.S. Application Data

(63) Continuation of application No. 13/397,481, filed on Feb. 15, 2012, now Pat. No. 9,031,701.
(Continued)

(51) Int. Cl.
*C12Q 1/68* (2018.01)
*G01N 15/06* (2006.01)
(Continued)

(52) U.S. Cl.
CPC ....... *G01N 33/4905* (2013.01); *G01N 29/024* (2013.01); *G01N 29/028* (2013.01);
(Continued)

(58) Field of Classification Search
USPC ........ 702/19; 700/266; 422/62, 68.1, 73, 80; 435/13
See application file for complete search history.

(56) References Cited

U.S. PATENT DOCUMENTS 3,996,791 A 12/1976 Niklas et al.
3,996,792 A 12/1976 Kubota et al.
(Continued)

FOREIGN PATENT DOCUMENTS

AU 2011/237383 10/2011
CA 2774680 3/2011
(Continued)

OTHER PUBLICATIONS

Huang et al., Detection of Blood Coagulation and Clot Formation Using Quantitative Ultrasonic Parameters, Ultrasound in Med. & Biol., vol. 31, No. 11, pp. 1567-1573, 2005.*
(Continued)

*Primary Examiner* — Dean Kwak
(74) *Attorney, Agent, or Firm* — Meunier Carlin & Curfman LLC

(57) ABSTRACT

An integrated system for determining a hemostasis and oxygen transport parameter of a blood sample, such as blood, is disclosed. The system includes a measurement system, such as an ultrasonic sensor, configured to determine data characterizing the blood sample. For example, the data could be displacement of the blood sample in response to ultrasonic pulses. An integrated aspect of the system may be a common sensor, sample portion or data for fast and efficient determination of both parameters. The parameters can also be used to correct or improve measured parameters. For example, physiological adjustments may be applied to the hemostatic parameters using a HCT measurement. Also, physical adjustments may be applied, such as through calibration using a speed or attenuation of the sound pulse through or by the blood sample. These parameters may be displayed on a GUI to guide treatment.

18 Claims, 30 Drawing Sheets

Related U.S. Application Data

(60) Provisional application No. 61/443,084, filed on Feb. 15, 2011.

(51) Int. Cl.
| | |
|---|---|
| *G01N 21/00* | (2006.01) |
| *G01N 33/00* | (2006.01) |
| *G01N 31/12* | (2006.01) |
| *C12Q 1/56* | (2006.01) |
| *G05B 21/00* | (2006.01) |
| *G01N 33/48* | (2006.01) |
| *G01N 33/49* | (2006.01) |
| *G01N 29/024* | (2006.01) |
| *G01N 29/032* | (2006.01) |
| *G01N 29/028* | (2006.01) |
| *G01N 29/44* | (2006.01) |

(52) U.S. Cl.
CPC .......... *G01N 29/032* (2013.01); *G01N 29/44* (2013.01); *G01N 33/49* (2013.01); *G01N 33/492* (2013.01); *G01N 2291/018* (2013.01); *G01N 2291/022* (2013.01); *G01N 2291/02466* (2013.01); *G01N 2291/02818* (2013.01); *G01N 2291/044* (2013.01)

(56) References Cited

U.S. PATENT DOCUMENTS

| | | |
|---|---|---|
| 4,105,018 A | 8/1978 | Greenleaf et al. |
| 4,112,740 A | 9/1978 | Brandestini |
| 4,123,731 A | 10/1978 | Kanbara et al. |
| 4,238,725 A | 12/1980 | Karplus et al. |
| 4,248,092 A | 2/1981 | Vasile et al. |
| 4,292,848 A | 10/1981 | Rainey et al. |
| 4,293,934 A | 10/1981 | Herolz et al. |
| 4,305,294 A | 12/1981 | Vasile et al. |
| 4,406,167 A | 9/1983 | Maeda |
| 4,435,984 A | 3/1984 | Gruber |
| 4,522,064 A | 6/1985 | McMillan |
| 4,558,589 A | 12/1985 | Hemmes et al. |
| 4,559,827 A | 12/1985 | Kupperman et al. |
| 4,570,487 A | 2/1986 | Gruber |
| 4,598,973 A | 7/1986 | Greenleaf |
| 4,641,531 A | 2/1987 | Reeves et al. |
| 4,658,649 A | 4/1987 | Brook |
| 4,658,827 A | 4/1987 | He et al. |
| 4,679,437 A | 7/1987 | Koike et al. |
| 4,695,956 A | 9/1987 | Leveen et al. |
| 4,702,110 A | 10/1987 | Holt |
| 4,705,756 A | 11/1987 | Spillert et al. |
| 4,735,096 A | 4/1988 | Dorr |
| 4,756,884 A | 7/1988 | Hillman et al. |
| 4,806,070 A | 2/1989 | Poux et al. |
| 4,814,247 A | 3/1989 | Spillert et al. |
| 4,829,430 A | 5/1989 | Greenleaf et al. |
| 4,852,577 A | 8/1989 | Smith et al. |
| 4,891,587 A | 1/1990 | Squire |
| 4,900,679 A | 2/1990 | Spillert et al. |
| 4,947,851 A | 8/1990 | Sarvazyan et al. |
| 5,007,291 A | 4/1991 | Walters et al. |
| 5,016,469 A | 5/1991 | Henderson |
| 5,036,286 A | 7/1991 | Holm-Kennedy |
| 5,038,787 A | 8/1991 | Antich et al. |
| 5,056,357 A | 10/1991 | Dymling et al. |
| 5,078,013 A | 1/1992 | Kuramochi et al. |
| 5,081,995 A | 1/1992 | Lu et al. |
| 5,082,418 A | 1/1992 | Poux et al. |
| 5,091,304 A | 2/1992 | La Duca |
| 5,104,975 A | 4/1992 | McCormick et al. |
| 5,115,808 A | 5/1992 | Popovic et al. |
| 5,204,525 A | 4/1993 | Hillman et al. |
| 5,205,159 A | 4/1993 | Carr, Jr. |
| 5,234,839 A | 8/1993 | McCormick et al. |
| 5,265,612 A | 11/1993 | Sarvazyan et al. |
| 5,273,517 A | 12/1993 | Barone et al. |
| 5,311,908 A | 3/1994 | Barone et al. |
| 5,331,964 A | 7/1994 | Trahey et al. |
| 5,408,882 A | 4/1995 | McKinley et al. |
| 5,431,054 A | 7/1995 | Reeves et al. |
| 5,439,157 A | 8/1995 | Geier et al. |
| 5,469,743 A | 11/1995 | Zorn |
| 5,473,536 A | 12/1995 | Wimmer |
| 5,474,225 A | 12/1995 | Geier et al. |
| 5,487,387 A | 1/1996 | Trahey et al. |
| RE35,171 E | 3/1996 | McCormick et al. |
| 5,504,011 A | 4/1996 | Gavin et al. |
| 5,524,636 A | 6/1996 | Sarvazyan et al. |
| 5,533,402 A | 7/1996 | Sarvazyan et al. |
| 5,534,226 A | 7/1996 | Gavin et al. |
| 5,605,154 A | 2/1997 | Ries et al. |
| 5,606,971 A | 3/1997 | Sarvazyan et al. |
| 5,614,670 A | 3/1997 | Nazarian et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,659,129 A | 8/1997 | Asoyan et al. |
| 5,673,699 A | 10/1997 | Trahey et al. |
| 5,678,565 A | 10/1997 | Sarvazyan |
| 5,681,996 A | 10/1997 | White |
| 5,706,815 A | 1/1998 | Sarvazyan et al. |
| 5,714,688 A | 2/1998 | Buttram et al. |
| 5,720,708 A | 2/1998 | Lu et al. |
| 5,744,898 A | 4/1998 | Smith et al. |
| 5,777,215 A | 7/1998 | Calatzis et al. |
| 5,777,229 A | 7/1998 | Geier et al. |
| 5,785,663 A | 7/1998 | Sarvazyan |
| 5,800,781 A | 9/1998 | Gavin et al. |
| 5,804,698 A | 9/1998 | Belonenko et al. |
| 5,810,731 A | 9/1998 | Sarvazyan et al. |
| 5,836,894 A | 11/1998 | Sarvazyan |
| 5,854,423 A | 12/1998 | Venegas |
| 5,860,934 A | 1/1999 | Sarvazyan |
| 5,888,826 A | 3/1999 | Ostgaard et al. |
| 5,899,861 A | 5/1999 | Friemel et al. |
| 5,903,516 A | 5/1999 | Greenleaf et al. |
| 5,921,928 A | 7/1999 | Greenleaf et al. |
| 5,922,018 A | 7/1999 | Sarvazyan |
| 5,952,560 A | 9/1999 | Collings et al. |
| 5,952,578 A | 9/1999 | White |
| 5,991,239 A | 11/1999 | Fatemi-Booshehri et al. |
| 6,016,701 A | 1/2000 | McClelland et al. |
| 6,016,712 A | 1/2000 | Warden et al. |
| 6,039,691 A | 3/2000 | Walker et al. |
| 6,046,051 A | 4/2000 | Jina |
| 6,068,597 A | 5/2000 | Lin |
| 6,070,466 A | 6/2000 | Taran et al. |
| 6,083,159 A | 7/2000 | Driscoll, Jr. et al. |
| 6,105,431 A | 8/2000 | Duffill et al. |
| 6,114,135 A | 9/2000 | Goldstein |
| 6,117,081 A | 9/2000 | Jago et al. |
| 6,135,957 A | 10/2000 | Cohen et al. |
| 6,142,959 A | 11/2000 | Sarvazyan et al. |
| 6,148,224 A | 11/2000 | Jensen |
| 6,155,117 A | 12/2000 | Stevens et al. |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lane et al. |
| 6,246,895 B1 | 6/2001 | Plewes |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,288,542 B1 | 9/2001 | Proksa et al. |
| 6,293,156 B1 | 9/2001 | Shen et al. |
| 6,318,191 B1 | 11/2001 | Chen |
| 6,360,610 B1 | 3/2002 | Jarzynski et al. |
| 6,371,912 B1 | 4/2002 | Nightingale et al. |
| 6,385,474 B1 | 5/2002 | Rather et al. |
| 6,402,704 B1 | 6/2002 | McMorrow |
| 6,412,344 B1 | 7/2002 | Danicich et al. |

(56) References Cited

U.S. PATENT DOCUMENTS

| | | |
|---|---|---|
| 6,432,236 B1 | 8/2002 | Leemon et al. |
| 6,436,722 B1 | 8/2002 | Clark et al. |
| 6,451,610 B1 | 9/2002 | Gorman et al. |
| 6,454,714 B1 | 9/2002 | Ng et al. |
| 6,486,669 B1 | 11/2002 | Sinkus et al. |
| 6,494,834 B2 | 12/2002 | Konofagou et al. |
| 6,508,768 B1 | 1/2003 | Hall et al. |
| 6,511,427 B1 | 1/2003 | Sliwa, Jr. et al. |
| 6,511,429 B1 | 1/2003 | Fatemi et al. |
| 6,514,204 B2 | 2/2003 | Alam et al. |
| 6,520,913 B1 | 2/2003 | Pesavento et al. |
| 6,535,835 B1 | 3/2003 | Rubin et al. |
| 6,537,819 B2 | 3/2003 | Cohen et al. |
| 6,546,278 B2 | 4/2003 | Walsh |
| 6,561,981 B2 | 5/2003 | Bonnefous |
| 6,569,108 B2 | 5/2003 | Sarvazyan et al. |
| 6,573,104 B2 | 6/2003 | Carr, Jr. et al. |
| 6,613,286 B2 | 9/2003 | Braun et al. |
| 6,613,573 B1 | 9/2003 | Cohen |
| 6,620,115 B2 | 9/2003 | Sarvazyan et al. |
| 6,626,049 B1 | 9/2003 | Ao |
| 6,632,678 B2 | 10/2003 | Aiken et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,705,993 B2 | 3/2004 | Ebbini et al. |
| 6,709,407 B2 | 3/2004 | Fatemi |
| 6,716,168 B2 | 4/2004 | Nock et al. |
| 6,726,629 B1 | 4/2004 | Frinking et al. |
| 6,728,567 B2 | 4/2004 | Rather et al. |
| 6,758,815 B2 | 7/2004 | Bernardi |
| 6,763,698 B2 | 7/2004 | Greenwood |
| 6,764,448 B2 | 7/2004 | Trahey et al. |
| 6,770,033 B1 | 8/2004 | Fink et al. |
| 6,787,363 B2 | 9/2004 | Cohen et al. |
| 6,797,519 B2 | 9/2004 | Cohen et al. |
| 6,824,516 B2 | 11/2004 | Batten et al. |
| 6,833,703 B2 | 12/2004 | Sinkus et al. |
| 6,837,109 B2 | 1/2005 | Okuno et al. |
| 6,837,854 B2 | 1/2005 | Moore et al. |
| 6,851,319 B2 | 2/2005 | Ziola et al. |
| 6,875,176 B2 | 4/2005 | Mourad et al. |
| 6,890,299 B2 | 5/2005 | Cohen et al. |
| 6,899,680 B2 | 5/2005 | Hoff et al. |
| 6,926,672 B2 | 8/2005 | Moore et al. |
| 6,937,886 B2 | 8/2005 | Zavislan |
| 6,939,298 B2 | 9/2005 | Brown et al. |
| 6,949,074 B2 | 9/2005 | Fatemi |
| 6,951,540 B2 | 10/2005 | Ebbini et al. |
| 6,951,544 B2 | 10/2005 | Trahey et al. |
| 6,964,640 B2 | 11/2005 | Zumeris et al. |
| 6,984,208 B2 | 1/2006 | Cheng |
| 6,984,209 B2 | 1/2006 | Hynynen et al. |
| 6,984,210 B2 | 1/2006 | Chambers et al. |
| 6,984,211 B2 | 1/2006 | Hao et al. |
| 7,001,335 B2 | 2/2006 | Adachi et al. |
| 7,016,725 B2 | 3/2006 | Palti |
| 7,022,077 B2 | 4/2006 | Mourad et al. |
| 7,025,253 B2 | 4/2006 | Sinkus et al. |
| 7,034,534 B2 | 4/2006 | Ehman et al. |
| 7,042,218 B2 | 5/2006 | Sellers |
| 7,089,054 B2 | 8/2006 | Palti |
| 7,114,373 B2 | 10/2006 | Hazelden et al. |
| 7,136,699 B2 | 11/2006 | Palti |
| 7,146,210 B2 | 12/2006 | Palti |
| 7,175,599 B2 | 2/2007 | Hynynen et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,207,939 B2 | 4/2007 | Husher |
| 7,225,010 B1 | 5/2007 | Zavislan |
| 7,240,556 B2 | 7/2007 | Georgeson et al. |
| 7,247,488 B2 | 7/2007 | Ghai et al. |
| 7,252,004 B2 | 8/2007 | Fink et al. |
| 7,261,861 B2 | 8/2007 | Kautzky |
| 7,268,548 B2 | 9/2007 | Sellers |
| 7,272,431 B2 | 9/2007 | McGrath |
| 7,275,439 B2 | 10/2007 | Zagzebski et al. |
| 7,285,092 B2 | 10/2007 | Duric et al. |
| 7,291,109 B1 | 11/2007 | Sarvazyan |
| 7,307,423 B2 | 12/2007 | Ehman et al. |
| 7,333,852 B2 | 2/2008 | Palti |
| 7,344,509 B2 | 3/2008 | Hynynen et al. |
| 7,367,948 B2 | 5/2008 | O'Donnell et al. |
| 7,370,534 B2 | 5/2008 | Lasser et al. |
| 7,374,538 B2 | 5/2008 | Nightingale et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,439,736 B2 | 10/2008 | Meaney et al. |
| 7,444,875 B1 | 11/2008 | Wu et al. |
| 7,467,011 B2 | 12/2008 | Palti |
| 7,519,420 B2 | 4/2009 | Palti |
| 7,520,172 B2 | 4/2009 | Gifford et al. |
| 7,520,855 B2 | 4/2009 | Tamano et al. |
| 7,524,670 B2 | 4/2009 | Cohen et al. |
| 7,547,283 B2 | 6/2009 | Mourad et al. |
| 7,549,985 B2 | 6/2009 | O'Donnell |
| 7,553,283 B2 | 6/2009 | Sandrin et al. |
| 7,565,205 B2 | 7/2009 | Palti |
| 7,565,206 B2 | 7/2009 | Palti |
| 7,597,665 B2 | 10/2009 | Wilk et al. |
| 7,599,745 B2 | 10/2009 | Palit |
| 7,599,746 B2 | 10/2009 | Palti |
| 7,611,465 B2 | 11/2009 | Antich et al. |
| 7,650,795 B2 | 1/2010 | Abousleiman et al. |
| 7,669,477 B2 | 3/2010 | Georgeson et al. |
| 7,674,616 B2 | 3/2010 | Farnam, III et al. |
| 7,706,890 B2 | 4/2010 | Palti |
| 7,713,201 B2 | 5/2010 | Chen et al. |
| 7,715,921 B2 | 5/2010 | Palti |
| 7,731,661 B2 | 6/2010 | Salcudean et al. |
| 7,732,213 B2 | 6/2010 | Cohen et al. |
| 7,740,051 B2 | 6/2010 | Iizuka et al. |
| 7,744,537 B2 | 6/2010 | Kenai et al. |
| 7,753,847 B2 | 7/2010 | Greenleaf et al. |
| 7,785,259 B2 | 8/2010 | Zheng et al. |
| 7,804,595 B2 | 9/2010 | Matula et al. |
| 7,805,201 B2 | 9/2010 | Palti |
| 7,806,823 B2 | 10/2010 | Sakai et al. |
| 7,811,234 B2 | 10/2010 | McGrath |
| 7,815,574 B2 | 10/2010 | Mourad et al. |
| 7,819,824 B2 | 10/2010 | Sarvazyan et al. |
| 7,822,243 B2 | 10/2010 | Demharter |
| 7,841,983 B2 | 11/2010 | Harada et al. |
| 7,857,766 B2 | 12/2010 | Lasater et al. |
| 7,871,379 B2 | 1/2011 | Ohtsuka |
| 7,871,406 B2 | 1/2011 | Nields et al. |
| 7,890,183 B2 | 2/2011 | Palti et al. |
| 7,892,188 B2 | 2/2011 | Walker et al. |
| 7,901,355 B2 | 3/2011 | Querleux et al. |
| 7,905,148 B2 | 3/2011 | Righetti et al. |
| 7,912,540 B2 | 3/2011 | Palti |
| 7,912,661 B2 | 3/2011 | Zeng |
| 7,917,227 B2 | 3/2011 | Palti |
| 7,922,674 B2 | 4/2011 | Sarvazyan et al. |
| 7,927,279 B2 | 4/2011 | Kubota et al. |
| 7,935,058 B2 | 5/2011 | Dupps, Jr. et al. |
| 7,938,778 B2 | 5/2011 | Sakai |
| 7,949,498 B2 | 5/2011 | Walker et al. |
| 7,955,278 B1 | 6/2011 | Sarvazyan |
| 7,966,882 B2 | 6/2011 | Greenwood |
| 7,971,630 B2 | 7/2011 | Iizuka et al. |
| 7,972,271 B2 | 7/2011 | Johnson et al. |
| 7,975,555 B2 | 7/2011 | Zhuang et al. |
| 7,987,718 B2 | 8/2011 | Huber et al. |
| 7,993,271 B2 | 8/2011 | Liu et al. |
| 7,999,945 B2 | 8/2011 | Zara |
| 8,019,414 B2 | 9/2011 | Palti |
| 8,027,738 B2 | 9/2011 | Palti |
| 8,052,602 B2 | 11/2011 | Sunagawa et al. |
| 8,052,622 B2 | 11/2011 | Egorov et al. |
| 8,058,023 B2 | 11/2011 | Gurbel |
| 8,066,644 B2 | 11/2011 | Sarkar et al. |

(56) References Cited

U.S. PATENT DOCUMENTS

| | | |
|---|---|---|
| 8,100,831 B2 | 1/2012 | Hiltawsky et al. |
| 8,107,694 B2 | 1/2012 | Hamilton et al. |
| 8,110,392 B2 | 2/2012 | Battrell et al. |
| 8,118,744 B2 | 2/2012 | Palmeri et al. |
| 8,121,670 B2 | 2/2012 | Zavislan |
| 8,137,275 B2 | 3/2012 | Fan et al. |
| 8,147,410 B2 | 4/2012 | Zheng |
| 8,150,128 B2 | 4/2012 | Konofagou et al. |
| 8,155,416 B2 | 4/2012 | Nields et al. |
| 8,155,725 B2 | 4/2012 | Pernot et al. |
| 8,170,684 B2 | 5/2012 | Palti |
| 8,175,698 B2 | 5/2012 | Palti et al. |
| 8,184,351 B2 | 5/2012 | Mills et al. |
| 8,187,187 B2 | 5/2012 | Fan et al. |
| 8,187,208 B2 | 5/2012 | Egorov et al. |
| 8,197,408 B2 | 6/2012 | Fan et al. |
| 8,207,733 B2 | 6/2012 | Meaney et al. |
| 8,225,666 B2 | 7/2012 | Mcaleavey |
| 8,244,345 B2 | 8/2012 | Palti |
| 8,249,691 B2 | 8/2012 | Chase et al. |
| 8,267,865 B2 | 9/2012 | Hoyt et al. |
| 8,281,663 B2 | 10/2012 | Ehman et al. |
| 8,286,467 B2 | 10/2012 | Fatemi et al. |
| 8,287,455 B2 | 10/2012 | Phung |
| 8,305,076 B2 | 11/2012 | Sack et al. |
| 8,306,293 B2 | 11/2012 | Walker |
| 8,323,199 B2 | 12/2012 | Salcudean et al. |
| 8,325,877 B2 | 12/2012 | Abenaim |
| 8,347,692 B2 | 1/2013 | Sinkus et al. |
| 8,353,096 B2 | 1/2013 | Ladabaum |
| 8,372,343 B2 | 2/2013 | Goldstein |
| 8,376,946 B2 | 2/2013 | Littrup et al. |
| 8,398,549 B2 | 3/2013 | Palmeri et al. |
| 8,398,550 B2 | 3/2013 | Insana et al. |
| 8,403,850 B2 | 3/2013 | Varghese et al. |
| 8,406,870 B2 | 3/2013 | Palti |
| 8,409,099 B2 | 4/2013 | Vitek et al. |
| 8,419,642 B2 | 4/2013 | Sandrin et al. |
| 8,419,659 B2 | 4/2013 | Egorov et al. |
| 8,425,424 B2 | 4/2013 | Zadicario et al. |
| 8,428,687 B2 | 4/2013 | Konofagou et al. |
| 8,447,395 B2 | 5/2013 | Palti et al. |
| 8,447,396 B2 | 5/2013 | Palti et al. |
| 8,465,533 B2 | 6/2013 | Palti |
| 8,469,891 B2 | 6/2013 | Maleke et al. |
| 8,494,791 B2 | 7/2013 | Hazard et al. |
| 8,500,639 B2 | 8/2013 | Yao |
| 8,523,787 B2 | 9/2013 | Ludwin et al. |
| 8,545,407 B2 | 10/2013 | Bercoff et al. |
| 8,545,410 B2 | 10/2013 | Hope Simpson et al. |
| 8,548,759 B2 | 10/2013 | Walker et al. |
| 8,556,888 B2 | 10/2013 | Nields et al. |
| 8,602,994 B2 | 12/2013 | Zheng et al. |
| 8,606,343 B2 | 12/2013 | Zavislan |
| 8,608,672 B2 | 12/2013 | Vortman et al. |
| 8,615,285 B2 | 12/2013 | Ehman et al. |
| 8,617,073 B2 | 12/2013 | Prus et al. |
| 8,685,636 B2 | 4/2014 | Braun et al. |
| 8,697,449 B2 | 4/2014 | Gregor et al. |
| 8,740,818 B2 | 6/2014 | Walker et al. |
| 8,809,007 B2 | 8/2014 | Christ et al. |
| 8,889,370 B2 | 11/2014 | Kappel et al. |
| 8,932,826 B2 | 1/2015 | Zander |
| 8,945,825 B2 | 2/2015 | Dekevic et al. |
| 9,272,280 B2 | 3/2016 | Viola et al. |
| 9,410,971 B2 | 8/2016 | Viola et al. |
| 9,915,671 B2 | 3/2018 | Schubert et al. |
| 9,977,039 B2 | 5/2018 | Viola et al. |
| 10,031,144 B2 | 7/2018 | Viola et al. |
| 10,161,944 B2 | 12/2018 | Viola et al. |
| 2001/0031934 A1 | 10/2001 | Sarvazyan et al. |
| 2001/0037074 A1 | 11/2001 | Sarvazyan et al. |
| 2001/0053384 A1 | 12/2001 | Greenleaf et al. |
| 2002/0004630 A1 | 1/2002 | Sarvazyan et al. |
| 2002/0013530 A1 | 1/2002 | Cespedes et al. |
| 2002/0040187 A1 | 4/2002 | Alam et al. |
| 2002/0081741 A1 | 6/2002 | Braun et al. |
| 2002/0143275 A1 | 10/2002 | Sarvazyan et al. |
| 2003/0013958 A1 | 1/2003 | Govari et al. |
| 2003/0073244 A1 | 4/2003 | Cohen et al. |
| 2003/0078227 A1 | 4/2003 | Greenleaf et al. |
| 2003/0083595 A1 | 5/2003 | Fatemi |
| 2003/0105398 A1 | 6/2003 | Vitek |
| 2003/0113929 A1 | 6/2003 | Baugh et al. |
| 2003/0128033 A1 | 7/2003 | Sinkus et al. |
| 2003/0153850 A1 | 8/2003 | Davis et al. |
| 2003/0170883 A1 | 9/2003 | Martin et al. |
| 2003/0171676 A1 | 9/2003 | Trahey et al. |
| 2003/0199082 A1 | 10/2003 | Miller |
| 2003/0201878 A1 | 10/2003 | Bai et al. |
| 2003/0204141 A1 | 10/2003 | Nock et al. |
| 2003/0236635 A1 | 12/2003 | Priev et al. |
| 2004/0054268 A1* | 3/2004 | Esenaliev ............ A61B 5/0095 600/322 |
| 2004/0065143 A1 | 4/2004 | Husher |
| 2004/0068184 A1 | 4/2004 | Trahey et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0093641 A1 | 5/2004 | Goddijn et al. |
| 2004/0123671 A1 | 7/2004 | Priev et al. |
| 2004/0133103 A1 | 7/2004 | Adachi et al. |
| 2004/0162504 A1 | 8/2004 | Fatemi |
| 2004/0167403 A1 | 8/2004 | Nightingale et al. |
| 2004/0199077 A1 | 10/2004 | Hao et al. |
| 2004/0203163 A1 | 10/2004 | Cohen et al. |
| 2004/0214337 A1 | 10/2004 | Kautzky |
| 2004/0225215 A1 | 11/2004 | Querleux et al. |
| 2004/0254503 A1 | 12/2004 | Sarvazyan et al. |
| 2004/0267121 A1 | 12/2004 | Sarvazyan et al. |
| 2004/0267165 A1 | 12/2004 | Sarvazyan et al. |
| 2005/0004463 A1 | 1/2005 | Chen et al. |
| 2005/0015001 A1* | 1/2005 | Lec .................... A61B 8/12 600/369 |
| 2005/0015009 A1* | 1/2005 | Mourad ............... A61B 5/031 600/438 |
| 2005/0053305 A1 | 3/2005 | Li et al. |
| 2005/0104588 A1 | 5/2005 | Sinkus et al. |
| 2005/0148899 A1 | 7/2005 | Walker et al. |
| 2005/0164373 A1 | 7/2005 | Oldham et al. |
| 2005/0165306 A1 | 7/2005 | Zheng et al. |
| 2005/0215899 A1 | 9/2005 | Trahey et al. |
| 2005/0215901 A1 | 9/2005 | Anderson et al. |
| 2005/0216987 P1 | 9/2005 | Murakami |
| 2005/0233460 A1 | 10/2005 | Clague et al. |
| 2005/0252295 A1 | 11/2005 | Fink et al. |
| 2006/0024746 A1 | 2/2006 | Sarvazyan |
| 2006/0207343 A1 | 9/2006 | Clifton et al. |
| 2006/0238763 A1 | 10/2006 | Sarvazyan et al. |
| 2006/0258934 A1 | 11/2006 | Zenge et al. |
| 2007/0016022 A1 | 1/2007 | Blalock et al. |
| 2007/0038095 A1 | 2/2007 | Greenleaf et al. |
| 2007/0038152 A1 | 2/2007 | Sarvazyan et al. |
| 2007/0059840 A1 | 3/2007 | Cohen et al. |
| 2007/0078631 A1 | 4/2007 | Ariyoshi et al. |
| 2007/0172388 A1* | 7/2007 | Padmanabhan ... B01L 3/502715 422/400 |
| 2007/0184508 A1 | 8/2007 | Cohen et al. |
| 2007/0259348 A1 | 11/2007 | Phadke et al. |
| 2007/0266778 A1* | 11/2007 | Corey ................ A61B 5/14535 73/61.75 |
| 2007/0276236 A1 | 11/2007 | Jong |
| 2008/0038828 A1 | 2/2008 | Cohen et al. |
| 2008/0076099 A1 | 3/2008 | Sarvazyan et al. |
| 2008/0097211 A1 | 4/2008 | Sarvazyan et al. |
| 2008/0154154 A1 | 6/2008 | Sarvazyan et al. |
| 2008/0194967 A1 | 8/2008 | Sliwa et al. |
| 2008/0200343 A1 | 8/2008 | Clemens |
| 2008/0221484 A1 | 9/2008 | Sarvazyan et al. |
| 2008/0249408 A1 | 10/2008 | Palmeri et al. |
| 2008/0261261 A1 | 10/2008 | Grimes et al. |
| 2008/0297169 A1 | 12/2008 | Greenquist et al. |
| 2008/0302187 A1 | 12/2008 | Huber et al. |
| 2009/0005707 A1 | 1/2009 | Sarvazyan et al. |

(56) References Cited

U.S. PATENT DOCUMENTS

| | | |
|---|---|---|
| 2009/0052272 A1 | 2/2009 | Sarvazyan |
| 2009/0052273 A1 | 2/2009 | Sarvazyan |
| 2009/0053688 A1 | 2/2009 | Bystryak et al. |
| 2009/0056453 A1 | 3/2009 | McAleavey |
| 2009/0093724 A1 | 4/2009 | Pernot et al. |
| 2009/0099485 A1 | 4/2009 | Sarvazyan et al. |
| 2009/0112483 A1 | 4/2009 | Cohen |
| 2009/0114019 A1 | 5/2009 | Fatemi et al. |
| 2009/0124901 A1 | 5/2009 | Fink et al. |
| 2009/0130645 A1 | 5/2009 | Schubert et al. |
| 2009/0216128 A1 | 8/2009 | Sarvazyan |
| 2009/0269837 A1 | 10/2009 | Shevkoplyas et al. |
| 2010/0010346 A1 | 1/2010 | Greenleaf et al. |
| 2010/0143241 A1 | 6/2010 | Johnson et al. |
| 2010/0154520 A1 | 6/2010 | Schubert |
| 2010/0170342 A1 | 7/2010 | Sinkus et al. |
| 2010/0190193 A1 | 7/2010 | Calatzis et al. |
| 2010/0191110 A1 | 7/2010 | Insana et al. |
| 2010/0204643 A1 | 8/2010 | Sarvazyan |
| 2010/0222678 A1 | 9/2010 | Bercoff et al. |
| 2010/0241001 A1 | 9/2010 | Palmeri et al. |
| 2010/0274130 A1 | 10/2010 | Anand et al. |
| 2011/0015547 A1 | 1/2011 | Sarvazyan et al. |
| 2011/0028838 A1 | 2/2011 | Pernot et al. |
| 2011/0034805 A1 | 2/2011 | Walker et al. |
| 2011/0054357 A1 | 3/2011 | Egorov et al. |
| 2011/0063950 A1 | 3/2011 | Greenleaf et al. |
| 2011/0065989 A1 | 3/2011 | Sarvazyan et al. |
| 2011/0065991 A1 | 3/2011 | Sarvazyan et al. |
| 2011/0066078 A1 | 3/2011 | Sarvazyan et al. |
| 2011/0092818 A1 | 4/2011 | Sarvazyan |
| 2011/0130660 A1 | 6/2011 | Cloutier et al. |
| 2011/0130683 A1 | 6/2011 | Sarvazyan |
| 2011/0130685 A1 | 6/2011 | Sarvazyan et al. |
| 2011/0144493 A1 | 6/2011 | Sarvazyan |
| 2011/0151491 A1 | 6/2011 | Dennis et al. |
| 2011/0166442 A1 | 7/2011 | Sarvazyan |
| 2011/0172661 A1 | 7/2011 | Designer et al. |
| 2011/0184287 A1 | 7/2011 | McAleavey |
| 2011/0196263 A1 | 8/2011 | Egorov et al. |
| 2011/0201931 A1 | 8/2011 | Palmeri et al. |
| 2011/0252352 A1 | 10/2011 | Viola et al. |
| 2011/0263978 A1 | 10/2011 | Chen et al. |
| 2011/0301465 A1 | 12/2011 | Waki |
| 2011/0319756 A1 | 12/2011 | Zheng et al. |
| 2012/0029286 A1 | 2/2012 | Sarvazyan et al. |
| 2012/0053450 A1 | 3/2012 | Salcudean et al. |
| 2012/0130248 A1 | 5/2012 | Fatemi |
| 2012/0143042 A1 | 6/2012 | Palmeri et al. |
| 2012/0203306 A1 | 8/2012 | Sarvazyan |
| 2012/0226158 A1 | 9/2012 | Greenleaf et al. |
| 2012/0232803 A1 | 9/2012 | Viola et al. |
| 2012/0244392 A1 | 9/2012 | Kleiman |
| 2012/0244564 A1* | 9/2012 | Walker ............... G01N 29/032 435/13 |
| 2012/0252127 A1 | 10/2012 | Bansil et al. |
| 2012/0259247 A1 | 10/2012 | Egorov et al. |
| 2012/0277632 A1 | 11/2012 | Sarvazyan et al. |
| 2012/0294767 A1 | 11/2012 | Viola et al. |
| 2012/0329082 A1 | 12/2012 | Viola et al. |
| 2013/0031981 A1 | 2/2013 | Montaldo et al. |
| 2013/0058195 A1 | 3/2013 | Cloutier et al. |
| 2013/0079645 A1 | 3/2013 | Amirana et al. |
| 2013/0102862 A1 | 4/2013 | Mercader et al. |
| 2013/0131754 A1 | 5/2013 | Sarvazyan |
| 2013/0144191 A1 | 6/2013 | Egorov et al. |
| 2013/0165778 A1 | 6/2013 | McAleavey |
| 2013/0190584 A1 | 7/2013 | Walker et al. |
| 2013/0237807 A1 | 9/2013 | Maitre et al. |
| 2013/0237821 A1 | 9/2013 | Amador et al. |
| 2014/0154706 A1 | 6/2014 | Zheng et al. |
| 2014/0242621 A1 | 8/2014 | Patzke et al. |
| 2014/0328732 A1 | 11/2014 | Delmenico et al. |

FOREIGN PATENT DOCUMENTS

| | | |
|---|---|---|
| CN | 1816306 | 8/2006 |
| CN | 101035479 | 9/2007 |
| CN | 103649751 | 3/2014 |
| DE | 202014002289 | 10/2014 |
| EP | 1162457 | 12/2001 |
| EP | 1347058 | 9/2003 |
| EP | 1901065 | 3/2008 |
| EP | 2555704 | 2/2013 |
| EP | 2676136 | 12/2013 |
| EP | 2676143 | 12/2013 |
| EP | 2690437 | 1/2014 |
| EP | 1618375 | 5/2014 |
| EP | 2772762 | 9/2014 |
| EP | 2484776 | 12/2014 |
| EP | 2634584 | 12/2014 |
| EP | 2513647 | 4/2015 |
| JP | 5401062 | 1/2014 |
| JP | 5563470 | 6/2014 |
| JP | 5655091 | 1/2015 |
| WO | 2008093216 | 8/2008 |
| WO | 2009123555 | 10/2009 |
| WO | 2009152094 | 12/2009 |
| WO | 2011/035162 | 3/2011 |
| WO | 2011/127436 | 10/2011 |
| WO | 2012/159021 | 11/2012 |
| WO | 2013/105986 | 7/2013 |
| WO | 2013/105987 | 7/2013 |
| WO | 2014/088987 | 6/2014 |
| WO | 2014/138533 | 9/2014 |
| WO | 2014/144259 | 9/2014 |
| WO | 2014/186411 | 11/2014 |
| WO | 2015/017535 | 2/2015 |
| WO | 2015/034646 | 3/2015 |

OTHER PUBLICATIONS

Voleisis et al., Ultrasonic method for the whole blood coagulation analysis, Ultrasonics 40 (2002) 101-107.*

Patent Examination Report No. 1, issued by IP Australia dated Dec. 4, 2015.

Amukele, T.K. et al., "Comparison of Plasma With Whole Blood Prothrombin Time and Fibrinogen on the Same Instrument," American Journal of Clinical Pathology, vol. 133, No. 4, 2010, pp. 550-556.

Anderson, M.E., "Multi-Dimensional Velocity Estimation with Ultrasound Using Spatial Quadrature," IEEE Transactions on Ultrasonics, Ferroelectrics, and Frequency Control, vol. 45, No. 3, 1998, pp. 852-861.

Anderson, Jr., F.A. et al., "Preventing Deep Vein Thrombosis and Pulmonary Embolism," Center for Outcomes Research, U Mass Med Center, 1998, 23 pages.

Becker, R.C., "Cell-Based Models of Coagulation: A Paradigm in Evolution," Journal of Thrombosis and Thrombolysis, vol. 20, No. 1, pp. 65-68.

Beer, A.E., "Thrombophilia: Inherited and Acquired," Center for Reproductive Immunology & Genetics, http://repro-med.net/papers/thromb.php, 2004, 6 pages.

Bell, C.R.W. et al., "Thrombelastographic evaluation of coagulation in transurethral prostatectomy," British Journal of Urology, vol. 78, No. 5, 1996, pp. 737-741.

Bercoff, J. et al., "In vivo Breast Tumor Detection Using Transient Elastography," Ultrasound in Medicine & Biology, vol. 29, No. 10, 2003, pp. 1387-1396.

Bercoff, J. et al., "Supersonic Shear Imaging: A New Technique for Soft Tissue Elasticity Mapping," IEEE Transactions on Ultrasonics, Ferroelectrics, and Frequency Control, vol. 51, No. 4, 2004, pp. 396-409.

Bilgen, M. et al., "Error analysis in acoustic elastography. II. Strain estimation and SNR analysis", Journal of the Acoustical Society of America, vol. 101, 1997, pp. 1147-1154.

Bohs, L.N. et al., "A Real Time System for Quantifying and Displaying Two-Dimensional Velocities Using Ultrasound," Ultrasound in Medicine & Biology, vol. 19, No. 9, 1993, pp. 751-761.

(56) References Cited

OTHER PUBLICATIONS

Bombeli, T. et al., "Updates in perioperative coagulation: physiology and management of thromboembolism and haemorrhage," British Journal of Anaesthesia; vol. 93, No. 2, 2004, pp. 275-287.
Bonnefous, O. et al., "Time Domain Formulation of Pulse-Doppler Ultrasound and Blood Velocity Estimation by Cross Correlation," Ultrasonic Imaging 8, 1986, pp. 73-85.
Brock, T.K. et al., "Assessing Thrombin Generation at the Point of Care," Clinical Chemistry, vol. 55, No. 3, 2009, pp. 389-399.
Carr, Jr., M.E., "In Vitro Assessment of Platelet Function," Transfusion of Medicine Reviews, vol. 11, No. 2, 1997, pp. 106-115.
Carroll, R.C. et al., "Measurement of functional fibrinogen levels using the Thrombelastograph," Journal of Clinical Anesthesia, vol. 20, No. 3, 2008, pp. 186-190.
Carter, G.C., "Coherence and Time Delay Estimation," Proceedings of the IEEE, vol. 75, No. 2, 1987, pp. 236-255.
Chakroun, T. et al., "The influence of fibrin polymerization and platelet-mediated contractile forces on citrated whole blood thromboelastography profile," Thrombosis and Haemostasis, vol. 95, No. 5, 2006, pp. 822-828.
Chandler, W.L. et al., "Development of a rapid emergency hemorrhage panel," Transfusion, vol. 50, No. 12, 2010, pp. 2547-2552.
Chandler, W.L. et al., "Estimating the rate of thrombin and fibrin generation in vivo during cardiopulmonary bypass," Blood, vol. 101, No. 11, 2003, pp. 4355-4362.
Chaturvedi, P. et al., "Testing the Limitations of 2-D Companding for Strain Imaging Using Phantoms," IEEE Transactions on Ultrasonics, Ferroelectrics, and Frequency Control, vol. 45, No. 4, 1998, pp. 1022-1031.
Chavez, J.J., "A Novel Thrombelastograph Tissue Factor/Kaolin Assay of Activated Clotting Times for Monitoring Heparin Anticoagulation During Cardiopulmonary Bypass," Anesthesia and Analgesia; vol. 99, No. 5, 2004, pp. 1290-1294.
Chonavel, T. et al., "Fast adaptive eigenvalue decomposition: a maximum likelihood approach," Signal Processing, vol. 83, 2003, pp. 307-324.
Cohn, N. A. et al., "An Elasticity Microscope. Part I: Methods," IEEE Transactions on Ultrasonics, Ferroelectrics, and Frequency Control, vol. 44, No. 6, 1997, pp. 1304-1319.
Cohn, N.A. et al., "An Elasticity Microscope. Part II: Experimental Results," IEEE Transactions on Ultrasonics, Ferroelectrics, and Frequency Control, vol. 44, No. 6, 1997, pp. 1320-1331.
Craft, R.M. et al., "A novel modification of the Thrombelastograph assay, isolating platelet function, correlates with optical platelet aggregation," The Journal of Laboratory and Clinical Medicine, vol. 143, No. 5, 2004, pp. 301-309.
Curry, A. et al., "Convention and near-patient tests of coagulation," British Journal of Anaesthesia, vol. 7, No. 2, Apr. 2007, pp. 45-50.
Dahlbäck, B., "Blood coagulation," The Lancet, Haematology, vol. 355, 2000, pp. 1627-1632.
Despotis, G.J. et al., "Monitoring of hemostasis in cardiac surgical patients: impact of point-of-care testing on blood loss and transfusion outcomes," Clinical Chemistry, vol. 43, No. 9, 1997, pp. 1684-1696.
Embree, P.M. et al., "Volumetric Blood Flow via Time-Domain Correlation: Experimental Verification," IEEE Transactions on Ultrasonics, Ferroelectrics, and Frequency Control, vol. 37, No. 2, 1990, pp. 176-189.
Emelianov, S.Y. et al., "Ultrasound Elasticity Imaging of Deep Venous Thrombosis," IEEE Ultrasonics Symposium, 2000, pp. 1791-1794.
Evans, P.A. et al., "Rheometry and associated techniques for blood coagulation studies," Medical Engineering and Physics, 2007, pp. 671-679.
Fatemi, M. et al., "Application of Radiation Force in Noncontact Measurement of the Elastic Parameters," Ultrasonic Imaging, vol. 21, No. 2, 1999, pp. 147-154.
Fatemi, M. et al., "C-Scan Imaging by Radiation Force Stimulated Acoustic Emission Method," IEEE Ultrasonics Symposium, 1996, pp. 1459-1462.

Fatemi, M. et al., "Ultrasound-Stimulated Vibro-Acoustic Spectography," Science, vol. 280, 1998, pp. 82-85.
Ferraris, V.A. et al., "2011 Update to the Society of Thoracic Surgeons and the Society of Cardiovascular Anesthesiologists Blood Conservation Clinical Practice Guidelines," Annals of Thoracic Surgery, vol. 91, 2011, pp. 944-982.
Fertner, A. et al., "Comparison of Various Time Delay Estimation Methods by Computer Simulation," IEEE Transactions on Acoustics, Speech, and Signal Processing, vol. ASSP-34, No. 5, 1986, pp. 1329-1330.
Flax, S.W. et al., "Phase-Aberration Correction Using Signals From Point Reflectors and Diffuse Scatterers: Basic Principles," IEEE Transactions on Ultrasonics, Ferroelectrics, and Frequency Control, vol. 35, No. 6, 1988, pp. 758-767.
Freedman, K.B. et al., "A Meta-Analysis of Thromboembolic Prophylaxis Following Elective Total Hip Arthroplasty," The Journal of Bone and Joint Surgery, vol. 82-A, No. 7, 2000, pp. 929-938.
Gaetano, G. de et al., "Effect of Platelets on Clot Structuration, a Thrombelastographic Study," Thrombosis Research, vol. 3, 1973, pp. 425-435.
Gallippi, C.M. et al., "Adaptive Clutter Filtering Via Blind Source," Ultrasonic Imaging, vol. 24, No. 4, 2002, pp. 193-214.
Gallippi, C.M. et al., "BSS-Based Filtering of Physiological and ARFI-Induced Tissue and Blood Motion," Ultrasound in Medicine and Biology, vol. 29, No. 11, 2003, pp. 1583-1592.
Gallippi, C.M. et al., "Complex Blind Source Separation for Acoustic Radiation Force Impulse Imaging in the Peripheral Vasculature, In Vivo," IEEE Ultrasonics Symposium, vol. 1, 2004, pp. 596-601.
Ganter, M.T. et al., "Active, Personalized, and Balanced Coagulation Management Saves Lives in Patients with Massive Bleeding," Anesthesiology, vol. 113, No. 5, 2010, pp. 1016-1018.
Ganter, M.T. et al., "Coagulation Monitoring: Current Techniques and Clinical Use of Viscoelastic Point-of-Care Coagulation Devices," Anesthesia and Analgesia, vol. 106, No. 5, 2008, pp. 1366-1375.
Gauss, R.C. et al., "Adaptive Imaging in the Thyroid Using Fundamental and Harmonic Echo Data," IEEE Ultrasonics Symposium, 1999, pp. 1515-1519.
Gauss, R.C. et al., "Wavefront Estimation in the Human Breast," Ultrasonic Imaging and Signal Processing, Proceedings of SPIE Medical Imaging, 2001, pp. 172-180.
Giunta, G. et al., "Estimation of Global Motion Parameters by Complex Linear Regression," IEEE Transactions on Image Processing, vol. 8, No. 11, 1999, pp. 1652-1657.
Glidden, P.F. et al., "Thromboelastograph Assay for Measuring the Mechanical Strength of Fibrin Sealant Clots," Clinical and Applied Thombosis/Hemostasis, vol. 6, No. 4, 2000, pp. 226-233.
Gottumukkala, V.N.R. et al., "Assessing Platelet and Fibrinogen Contribution to Clot Strength Using Modified Thromboelastography in Pregnant Women," Anesthiology and Analgesia, vol. 89, 1999, pp. 1453-1455.
Greilich, P.E. et al., "A Modified Thromboelastographic Method for Monitoring c7E3 Fab in Heparinized Patients," Anesthesia & Analgesia, vol. 84, 1997, pp. 31-38.
Greilich, P.E. et al., "Near-Site Monitoring of the Antiplatelet Drug Abciximad Using the Hemodyne Analyzer and Modified Thrombelastograph," Journal of Cardiothoracic and Vascular Anesthesia, vol. 13, No. 1, Feb. 1999, pp. 58-64.
Gurbel, P.A. et al., "Platelet Function Monitoring in Patients With Coronary Artery Disease," Journal of the American College of Cardiology, vol. 50, No. 19, 2007, pp. 1822-1834.
Harris, J.M. et al., "Evaluation of Recurrent Thrombosis and Hypercoagulability," American Family Physicians, vol. 56, No. 6, 1997, 6 pages.
Hartley, C.J., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, C.J, "Doppler Measurement of Acoustic Streaming," IEEE Ultrasonics Symposium, 1995, pp. 1537-1540.
Hett, D.A. et al., "Sonoclot Analysis," British Journal of Anaesthesia, vol. 75, 1995, pp. 771-776.
Hirsh, J. et al., "How we diagnose and treat deep vein thrombosis," Blood, vol. 99, No. 9, 2002, pp. 3102-3110.

(56) References Cited

OTHER PUBLICATIONS

Hirsh, J. et al., "Management of Deep Vein Thrombosis and Pulmonary Embolism," Circulation, American Heart Association, vol. 93, 1996, pp. 2212-2245.
Hoffman, M. et al., "A Cell-based Model of Hemostasis," Thrombosis and Haemostasis, vol. 85, 2001, pp. 958-965.
Huang, C-C et al., "Characterization of Blood Properties from Coagulating Blood of Different Hematocrits Using Ultrasonic Backscatter and Attenuation," Japanese Journal of Applied Physics, vol. 45, No. 9A, 2006, pp. 7191-7196.
Huang, C-C et al., "Detection of Blood Coagulation and Clot Formation Using Quantitative Ultrasonic Parameters," Ultrasound in Medicine and Biology, vol. 31, No. 11, 2005, pp. 1567-1573.
Ickx, B., "Point-of-Care Monitoring of Haemostasis in the OR and the ICU," European Society of Anaesthesiologists, 2004, pp. 79-83.
Ivandic, B.T. et al., "Determination of Clopidogrel Resistance by Whole Blood Platelet Aggregometry and Inhibitors of the $P2Y_{12}$ Receptor," Clinical Chemistry, vol. 52, No. 3, 2006, pp. 383-388.
Jacovitti, G. et al., "Discrete Time Techniques for Time Delay Estimation," IEEE Transactions on Signal Processing, vol. 41, No. 2, 1993, pp. 525-533.
Jensen, J.A. et al., "A New Method for Estimation of Velocity Vectors," IEEE Transactions on Ultrasonics, Ferroelectrics, and Frequency Control, vol. 45, No. 3, 1998, pp. 837-851.
Jensen, J.A. et al., "Calculation of Pressure Fields from Arbitrarily Shaped, Apodized, and Excited Ultrasound Transducers," IEEE Transactions on Ultrasonics, Ferroelectrics, and Frequency Control, vol. 39, No. 2, 1992, pp. 262-267.
Jensen, J.A., "Color flow mapping using phase shift estimation," Estimation of Blood Velocities Using Ultrasound: A Signal Processing Approach, 1996, pp. 195-225.
Jolliffe, I.T., "Principal Component Analysis," Second Edition, Springer Series in Statistics, Springer, New York, 2002, 40 pages.
Kadi, A.P. et al., "On the Performance of Regression and Step-Initialized IIR Clutter Filters for Color Doppler Systems in Diagnostic Medical Ultrasound," IEEE Transactions on Ultrasonics, Ferroelectrics, and Frequency Control, vol. 42, No. 5, 1995, pp. 927-937.
Kasai, C. et al., "Real-Time Two-Dimensional Blood Flow Imaging Using an Autocorrelation Technique," IEEE Transactions on Sonics and Ultrasonics, vol. SU-32, No. 3, 1985, pp. 458-464.
Katori, N. et al., "The Effects of Platelet Count on Clot Retraction and Tissue Plasminogen Activator-Induced Fibrinolysis on Thrombelastography," Anesthesia and Analgesia, vol. 100, No. 6, 2005, pp. 1781-1785.
Keresztes, P.A. et al., "The PFA-100: Analysis and Interpretation of a Platelet Function Measurement," The Journal of Cardiovascular Nursing, vol. 20, No. 6, 2005, pp. 405-407.
Kettner, S.C. et al., "Use of abciximab-Modified Thrombelatography in Patients Undergoing Cardiac Surgery," Anesthesia & Analgesia, vol. 89, 1999, pp. 580-584.
Khurana, S. et al., "Monitoring Platelet Glycoprotein IIb/IIa-fibrin Interaction with tissue factor-activated thromboelastography," Journal of Laboratory and Clinical Medicine, vol. 130, No. 4, 1997, pp. 401-411.
Khurana, S., "Thromboelastography Can Rapidly Bioassay Fibrinogen," Anesthesiology, vol. 85, No. 3A, 1996, 1 page.
Koepke, J., "Point-of-Care Coagulation Testing," Laboratory Medicine, vol. 31, No. 6, 2000, pp. 343-346.
Kruse, D.E. et al., "A New High Resolution Color Flow System Using an Eigendecomposition-Based Adaptive Filter for Clutter Rejection," IEEE Transactions on Ultrasonics, Ferroelectrics, and Frequency Control, vol. 49, No. 10, 2002, pp. 1384-1399.
Ledoux, L.A.F. et al., "Reduction of the Clutter Component in Doppler Ultrasound Signals Based on Singular Value Decomposition: a Simulation Study," Ultrasonic Imaging, vol. 19, No. 1, 1997, pp. 1-18.

Lerner, R.M. et al., "Sono-Elasticity: Medical Elasticity Images Derived from Ultrasound Signals in Mechanically Vibrated Targets," Ultrasound in Medicine & Biology, vol. 16, 1998, pp. 317-327.
Libgot, R. et al., "High frequency ultrasound characterization of the blood clotting process: intra- and inter-individual variations," IEEE Ultrasonics Symposium, pp. 2259-2262.
Loupas, T. et al., "An Axial Velocity Estimator for Ultrasound Blood Flow Imaging, Based on a Full Evaluation of the Doppler Equation by Means of a Two-Dimensional Autocorrelation Approach," IEEE Transactions on Ultrasonics, Ferroelectrics, and Frequency Control, vol. 42, No. 4, 1995, pp. 672-688.
Lubinski, M.A. et al., "Adaptive Strain Estimation Using Retrospective Processing," IEEE Transactions on Ultrasonics, Ferroelectrics, and Frequency Control, vol. 46, No. 1, 1999, pp. 97-107.
Mahla, E. et al., "Thromboelastography for Monitoring Prolonged Hypercoagulability After Major Abdominal Surgery," Anesthesia and Analgesia, vol. 92, No. 3, 2001, pp. 572-577.
Malinin, A. et al., "Validation of a VerifyNow-P2Y12® Cartridge for Monitoring Platelet Inhibition with Clopidogrel," Methods and Findings in Experimental and Clinical Pharmacology, vol. 28, No. 5, 2006, pp. 315-322.
Mauldin, Jr., F.W. et al., "Adaptive Force Sonorheometry for Assessment of Whole Blood Coagulation," Clinica Chimica Acta, vol. 411, Issues 9-10, 2010, pp. 638-644.
Mauldin, Jr., F.W. et al., "Robust Principal Component Analysis and Clustering Methods for Automated Classification of Tissue Response to ARFI Excitation," Ultrasound in Medicine & Biology, vol. 34, No. 2, 2008, pp. 309-325.
McAleavey, S.A. et al., "Estimates of Echo Correlation and Measurement Bias in Acoustic Radiation Force Impulse Imaging," IEEE Transactions on Ultrasonics, Ferroelectrics, and Frequency Control, vol. 50, No. 6, 2003, pp. 631-641.
Ng, G.C. et al., "A Comparative Evaluation of Several Algorithms for Phase Aberration Correction," IEEE Transactions on Ultrasonics, Ferroelectrics, and Frequency Control, vol. 41, No. 5, 1994, pp. 631-643.
Nielson, V.G. et al., "Effects of coagulation factor deficiency on plasma coagulation kinetics determined via thrombelastography®: critical roles of fibrinogen and factors II, VII, X and XII," Acta Anesthesiologica Scandanavia, vol. 49, No. 2, 2005, pp. 222-231.
Nightingale, K. et al., "Acoustic Radiation Force Impulse Imaging: In Vivo Demonstration of Clinical Feasibility," Ultrasound in Medicine & Biology, vol. 28, 2002, pp. 227-235.
Nightingale, K. et al., "Acoustic Remote Palpation: Initial In Vivo Results," IEEE Ultrasonics Symposium, 2000, pp. 1553-1558.
Nightingale, K. et al., "Shear-Wave Generation Using Acoustic Radiation Force: In Vivo and Ex Vivo Results," Ultrasound in Medicine & Biology, vol. 29, No. 12, 2003, pp. 1715-1723.
O'Donnell, M. et al., "Internal Displacement and Strain Imaging using Ultrasonic Speckle Tracking," IEEE Transactions on Ultrasonics, Ferroelectrics, and Frequency Control, vol. 41, No. 3, 1994, pp. 314-325.
O'Donnell, J. et al., "Role of the Thrombelastograph as an adjunctive test in thrombophilia screening," Blood Coagulation and Fibrinolysis, vol. 15, No. 3, 2004, pp. 207-211.
Oberhardt, B.J. et al., "Dry Reagent Technology for Rapid, Convenient Measurements of Blood Coagulation and Fibrinolysis," Clinical Chemistry, vol. 37, No. 4, 1991, pp. 520-526.
Ophir, J. et al., "Elastography: A Quantitative Method for Imaging the Elasticity of Biological Tissues," Ultrasonic Imaging, vol. 13, 1991, pp. 111-134.
Packham, M.A., "Role of platelets in thrombosis and hemostasis," Canadian Journal of Physiology and Pharmacology, vol. 72, No. 3, 1994, pp. 278-284.
Palmeri, M.L. et al., "Ultrasonic Tracking of Acoustic Radiation Force-Induced Displacements in Homogeneous Media," IEEE Transactions on Ultrasonics, Ferroelectrics, and Frequency Control, vol. 53, No. 7, 2006, pp. 1300-1313.
Parsons, R.E. et al., "Age determination of experimental venous thrombi by ultrasonic tissue characterization," Journal of Vascular Surgery, vol. 17, No. 3, 1993, 470-478.

(56) References Cited

OTHER PUBLICATIONS

Patil, A.V. et al., "3D prostate elastography: algorithm, simulations and experiments," Physics in Medicine & Biology, vol. 52, 2007, pp. 3643-3663.
Perry, D.J. et al., "Point-of-care testing in haemostasis," British Journal of Haematology, vol. 150, 2010, pp. 501-514.
Pivalizza, E.G. et al., "Perioperative thromboelastography and sonoclot analysis in morbidly obese patients," Canadian Journal of Anaesthesia, vol. 44, No. 9, 1997, pp. 942-945.
Rao, G., "Need for a Point-Of-Care Assay for Monitoring Antiplatelet and Antithrombotic Therapies," Stroke, vol. 40, 2009, pp. 2271-2272.
Rubin, J.M. et al., "Clinical Application of Sonographic Elasticity Imaging for Aging of Deep Venous Thrombosis: Preliminary Findings," Journal of Ultrasound in Medicine, vol. 22, 2003, pp. 443-448.
Sakharov, D.V. et al., "Acceleration of Fibrinolysis by High-frequency Ultrasound: The Contribution of Acoustic Streaming and Temperature Rise," Thrombosis Research, vol. 100, 2000, pp. 333-340.
Sarvazyan, A.P. et al., "Shear Wave Elasticity Imagining: A New Ultrasonic Technology of Medical Diagnostics," Ultrasound in Medicine and Biology, vol. 24, No. 9, 1998, pp. 1419-1436.
Schmitt, C. et al., "Characterization of blood clot viscoelasticity by dynamic ultrasound elastography and modeling of the rheological behavior," Journal of Biomechanics, vol. 44, 2011, pp. 622-629.
Shi, X. et al., "Color Doppler Detection of Acoustic Streaming in a Hematoma Model," Ultrasound in Medicine and Biology, vol. 27, No. 9, 2001, pp. 1255-1264.
Shi, X. et al., "Color Doppler imaging of acoustic streaming in blood and clot," IEEE Ultrasonics Symposium, vol. 2, 1999, pp. 1315-1318.
Shi et al., "Experimental Investigation and Finite Element Simulation of Streaming in Blood in Cylindrical Models," IEEE Ultrasonics Symposium, vol. 2, 2000, pp. 1509-1512.
Shi, X. et al., "Quantitative investigation of acoustic streaming in blood," Journal of the Acoustical Society of America, vol. 111, No. 2, 2002, pp. 1110-1121.
Shih, C-C et al., "In Vitro Assessments of Viscoelastic Properties of Fibrin Clot by Using Acoustic Radiation Force on a Solid Sphere," IEEE Proceedings of the International Ultrasonics Symposium, 2010, pp. 479-482.
Shung, K.K. et al., "Ultrasonic Characterization of Blood During Coagulation," Journal of Clinical Ultrasound, vol. 12, 1984, pp. 147-153.
Skovoroda, A.R. et al., "Tissue Elasticity Reconstruction Based on Ultrasonic Displacement and Strain Images," IEEE Transactions on Ultrasonics, Ferroelectrics, and Frequency Control, vol. 42, No. 4, 1995, pp. 747-765.
Srinivasan, S. et al., "Elastographic Imaging Using Staggered Strain Estimates," Ultrasonic Imaging, vol. 24, 2002, pp. 229-245.
Strobach, P., "Low-Rank Adaptive Filters," IEEE Transactions on Signal Processing, vol. 44, No. 12, 1996, pp. 2932-2947.
Sugimoto, T. et al., "Tissue Hardness Measurement Using the Radiation Force of Focused Ultrasound," Proceedings of the IEEE Ultrasonic Symposium, 1990, pp. 1377-1380.
Sumino, Y. et al., "Measurements of ultrasonic pulse arrival time differences produced by abdominal wall specimens," Journal of the Acoustical Society of America, vol. 90, No. 6, 1991, pp. 2924-2930.
Thuerlemann, C. et al., "Monitoring Thrombin Generation by Electrochemistry: Development of an Amperometric Biosensor Screening Test for Plasma and Whole Blood," Clinical Chemistry, vol. 55, No. 3, 2009, pp. 505-512.
Toner, M. et al., "Blood-On-A-Chip," Annual Review of Biomedical Engineering, vol. 7, 2005, pp. 77-103.
Torr, G.R., "The Acoustic Radiation Force," American Journal of Physics, vol. 52, No. 5, 1984, pp. 402-408.
Trahey, G.E. et al., "Synthetic Receive Aperture Imaging with Phase Correction for Motion and for Tissue Inhomogeneities—Part II: Effects of and Correction for Motion," IEEE Transactions on Ultrasonics, Ferroelectrics, and Frequency Control, vol. 39, No. 4, 1992, pp. 496-501.
Traverso, C.I. et al., "Prospective assessment of the risk of deep vein thrombosis in elective abdominal surgery. Predictive role of Thromboelastography," Thrombotics and Haemorrhagic Disorders, vol. 7, No. 1, 1993, pp. 9-15.
Vig, S. et al., "Thromboelastography: a reliable test?," Blood Coagulation and Fibrinolysis, vol. 12, 2001, pp. 555-561.
Viola, F. et al., "A Comparison Between Spline-Based and Phase-Domain Time-Delay Estimators," IEEE Transactions on Ultrasonics, Ferroelectrics, and Frequency Control, vol. 53, No. 3, 2006, pp. 515-517.
Viola, F. et al., "A Comparison of the Performance of Time-Delay Estimators in Medical Ultrasound," IEEE Transactions on Ultrasonics, Ferroelectrics, and Frequency Control, vol. 50, No. 4, 2003, pp. 392-401.
Viola, F. et al., "A Novel Ultrasound-Based Method to Evaluate Hemostatic Function of Whole Blood," Clinica Chimica Acta, vol. 411, Nos. 1-2, 2010, pp. 106-113.
Viola, F. et al., "A Spline-Based Algorithm for Continuous Time-Delay Estimation Using Sampled Data," IEEE Transactions on Ultrasonics, Ferroelectrics, and Frequency Control, vol. 52, No. 1, 2005, pp. 80-93.
Viola, F. et al., "Analysis of Clot Formation with Acoustic Radiation Force," SPIE Proceedings, vol. 4687, 2002, pp. 235-242.
Viola, F. et al., "Comparison of Time Delay Estimators in Medical Ultrasound," IEEE Ultrasonics Symposium, vol. 2, 2001, pp. 1485-1488.
Viola, F. et al., "Efficient and Accurate Spline-Based Time Delay Estimation," IEEE Ultrasonics Symposium, vol. 2, 2004, pp. 870-873.
Viola, F. et al., "Imaging Viscoelastic Properties of the Vitreous," IEEE Ultrasonics Symposium, vol. 2, 2001, pp. 1623-1626.
Viola, F. et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, F. et al., "Sonorheometry: A new Method for Assessing Coagulation Potential," IEEE Ultrasonics Symposium, vol. 1, 2007, pp. 1001-1004.
Viola, F. et al., "Sonorheometry: A Noncontact Method for the Dynamic Assessment of Thrombosis," Annals of Biomedical Engineering, vol. 32, No. 5, 2004, pp. 696-705.
Viola, F. et al., "Ultrasound Echo Decorrelation Due to Acoustic Radiation Force," Proceedings of the IEEE Ultrasonics Symposium, vol. 2, 2002, pp. 1903-1906.
Voleršis, A. et al., "Ultrasonic method for the whole blood coagulation analysis," Ultrasonics, vol. 40, 2002, pp. 101-107.
Walker, W.F. et al., "A Fundamental Limit on Delay Estimation Using Partially Correlated Speckle Signals," IEEE Transactions on Ultrasonics, Ferroelectrics, and Frequency Control, vol. 42, No. 2, 1995, pp. 301-308.
Walker, W.F. et al., "A Fundamental Limit on the Accuracy of Speckle Signal Alignment," Proceedings of the IEEE Ultrasonics Symposium, vol. 3, 1994, pp. 1787-1791.
Walker, W.F. et al., "A method of imagining viscoelastic parameters with acoustic radiation force," Physics in Medicine and Biology, vol. 45, No. 6, 2000, pp. 1437-1447.
Walker, W.F. et al., "Application of Acoustic Radiation Force in Ophthalmic Ultrasound," Proceedings of the IEEE Ultrasonic Symposium, vol. 2, 1997, pp. 1291-1295.
Walker, W.F. et al., "Real-Time Imaging of Tissue Vibration Using a Two-Dimensional Speckle Tracking System," IEEE Ultrasonic Symposium, 1993, pp. 873-877.
Walker, W.F., "The Significance of Correlation in Ultrasound Signal Processing," SPIE Proceedings, vol. 4325, 2001, pp. 159-171.
Westbrook, A.J. et al., "Protocol Based on Thromboelastograph (TEG) Out-Performs Physician Preference Using Laboratory Coagulation Tests to Guide Blood Replacement During and After Cardiac Surgery: A Pilot Study," Heart, Lung and Circulation, vol. 18, No. 4, 2009, pp. 277-288.

(56) References Cited

OTHER PUBLICATIONS

Whitten, C.W. et al., "Thromboelastography: Past, Present, and Future," Anesthesiology, vol. 92, No. 5, 2000, pp. 1223-1225.
Yu, A.C.H. et al., "Single-Ensemble-Based Eigen-Processing Methods for Color Flow Imaging—Part II. The Matrix Pencil Estimator," IEEE Transactions on Ultrasonics, Ferroelectrics, and Frequency Controls, vol. 55, No. 3, 2008, pp. 573-587.
Zieliński, T.P. et al., "Frequency and Damping Estimation Methods—An Overview," Metrology and Measurement Systems, vol. 18, No. 4, 2011, pp. 505-528.
International Preliminary Report on Patentability and Written Opinion, dated Oct. 8, 2013, in connection with International Application No. PCT/US2012/025270.
International Search Report, dated Sep. 30, 2013, in connection with International Application No. PCT/US2012/025270.
International Preliminary Report on Patentability and Written Opinion, dated Aug. 27, 2013, in connection with International Application No. PCT/US2012/025278.
International Search Report, dated Aug. 20, 2013, in connection with International Application No. PCT/US2012/025278.
International Preliminary Report on Patentability and Written Opinion, dated Oct. 9, 2012, in connection with International Application No. PCT/US2011/031832.
International Search Report, dated Dec. 15, 2011, in connection with International Application No. PCT/US2011/031832.
International Preliminary Report on Patentability and Written Opinion, dated Nov. 19, 2013, in connection with International Application No. PCT/US2012/038553.
International Search Report, dated Jan. 2, 2013, in connection with International Application No. PCT/US2012/038553.
International Preliminary Report on Patentability and Written Opinion, dated Mar. 20, 2012, in connection with International Application No. PCT/US2010/049342.
International Search Report, dated Nov. 16, 2010, in connection with International Application No. PCT/US2010/049342.
Merrill et al., Rheology of Human Blood, near and at Zero Flow, Biophysical Journal, 3(3):199-213 (1963).
Wang et al., Detection of the process of blood coagulation and clot formation using quantitative ultrasonic parameters, IEEE Ultrasonics Symposium Proceedings, Muenchen, Germany (Oct. 8-11, 2002), vol. 2, pp. 1653-1656.
Extended European Search Report issued in Application No. 12865373.0 dated Dec. 7, 2016.
Office Action issued for Canadian Application No. 2,823,729, dated Apr. 6, 2020.
Wilson, D, et al. "Changes in Coagulability as Measured by Thrombelastography Following Surgery for Proximal Femoral Fracture." Injury, vol. 32, No. 10, 2001, pp. 765-770., doi:10.1016/s0020-1383(01)00139-5. (Year: 2001).
Office Action issued for U.S. Appl. No. 15/641,731, dated Apr. 20, 2020.
Office Action issued for U.S. Appl. No. 15/641,731, dated Sep. 27, 2019.
Hardisty R. M. et al, "Fibrinogen as a Co-factor in the Reaction of Platelets with Kaolin," May 7, 1966, Nature Publishing Group, Edition 210, vol. 644 (http://www.nature.com/nature/journal/v210/n5036/abs/210644a0.html)/ Abstract.
Riou, et al., "Fast adaptive eigenvalue decomposition: a maximum likelihood approach," IEEE International Conference on Acoustics, Speech, and Signal Processing, vol. 5, 1997, pp. 3565-3568.
Spiel, A. O. et al.,"Validation of rotation thrombelastography in a model of systemic activation of fibrinolysis and coagulation in humans", Journal of Thrombosis and Haemostasis, 2006; 4: 411-416.
Azar et al., "Abciximab in Primary Coronary Angioplasty for Acute Myocardial Infarction Improves Short- and Medium-Term Outcomes", J. Am. Coll. Cardiol., Dec. 1998; 32(7):1996-2002. PubMed P.M.I.D.: 9857884.

Born, G.V., "Aggregation of Blood Platelets by Adenosine Diphosphate and its Reversal". Nature, Jun. 9, 1962; 194:927-9. PubMed P.M. I.D.: 13871375.
Calle et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36(2):295-305. PubMed P.M.I. D.: 20045589.
Coiffic et al., "Inhibition of Platelet Aggregation by Abciximab but not by Aspirin can be Detected by a New Point-of-Care Test, the Hemostatus". Thromb. Res., Jul. 15, 1999, 95(2):83-91. PubMed P.M.I.D.: 10418797.
Communication pursuant to Rule 114(2) EPC issued in European Patent Application No. 12865280.7, dated Dec. 13, 2016, 5 pages.
Communication pursuant to Rule 94(3)) EPC issued in European Patent Application No. 12865280.7, dated Jul. 3, 2017, 3 pages.
Communication pursuant to Article 94(3) EPC issued in European Patent Application No. 12865280.7, dated Apr. 3, 2018.
Extended Search Report issued in European Patent Application No. 12865280, dated Oct. 24, 2016, 5 pages.
Examination Report issued in European Application No. 12865280. 7, dated Mar. 7, 2017, 3 pages.
Communication pursuant to Article 94(3) EPC issued in European Patent Application No. 12865280.7, dated Oct. 8, 2018.
Communication pursuant to Article 94(3) EPC issued in European Patent Application No. 12865280.7, dated Mar. 18, 2019.
Summons to attend oral proceeding pursuant to Rule 115(1) EPC European Patent Application No. 12865280.7, dated Dec. 5, 2019.
Declaration of U.S. Pat. No. 9,272, 280, 67 pages.
Declaration of U.S. Pat. No. 9,410,971,124 pages.
Delhaye et al., Temperature corrected thromboelastometry in hypothermic trauma patients: 6AP24. European Journal of Anaesthesiology, May/ Jun. 2008, 25:84.
Dorn-Beineke et al., "Evaluation of the Automated Coagulation Analyzer Sysmex CA-7000". Thromb. Res., 2005; 116(2):171-9. PubMed P.M.I.D.:15907533.
Douning et al., "Temperature Corrected Thrombelastography in Hypothermic Patients". Anesthesia & Analgesia, Oct. 1995; 81(3):608-11.
Eikelboom et al., "Monitoring Unfractionated Heparin with the aPTT: Time for a Fresh Look". Thromb. Haemost. Nov. 2006; 96(5):547-52. Review. PubMed P.M.I.D.: 17080209.
Extended European Search Report issued in European Patent Application No. 11766842.6, dated Oct. 21, 2015, 10 pages.
Flanders et al., "Evaluation and Performance Characteristics of the STA-R Coagulation Analyzer". Clin Chem., Sep. 2002; 48(9):1622-4. PubMed P.M.I.D.: 12194955.
Ganter et al., "Kaolin-Based Activated Coagulation Time Measured by Sonoclot in Patients Undergoing Cardiopulmonary Bypass." J. Cardiothorac. Vasc. Anesth, Aug. 2007; 21(4):524-8. PubMed P.M. I.D.: 17678778.
Gorlinger et al., "Recommendations for using the ROTEM® in the management of perioperative bleeding in Cardiac Surgery" Recommendations from the ROTEM® Expert Meeting Working Group, Munich 2007, 10 pages.
Gosselin et al., "Monitoring Oral Anticoagulant Therapy with Point-of-Care Devices: Correlations and Caveats". Clin. Chem., Sep. 1997; 43(9):1785-6. PubMed P.M.I.D.: 9299978.
Harrison, P. Platelet Function Analysis. Blood Rev. Mar. 2005; 19(2):111-23. Review. PubMed P.M.I.D.: 15603914.
Hirsh et al., "Oral anticoagulants. Mechanism of Action, Clinical Effectiveness, and Optimal Therapeutic Range". Chest. Oct. 1992; 102(4 Suppl.):312S-326S. Review. PubMed P.M.I.D.: 1345417.
Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110(1):36-45. PubMed P.M.I.D.: 7609566.
Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention". Am. J. Cardiol., Aug. 15, 1999; 84(4):391-5. PubMed P.M.I.D.: 10468074.

(56) References Cited

OTHER PUBLICATIONS

Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33(3):153-8. PubMed P.M.I.D.: 11680728.
Lang et al., "Multi-center investigation on reference ranges from ROTEM thromboelasatometry", Blood coagul. Fibrinol 16:4, 2005, pp. 301-310.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Li et al., "The Xylum Clot Signature Analyzer: A Dynamic Flow System that Simulates Vascular Injury". Thromb. Res., Dec. 15, 1998; 92(6 Suppl. 2):S67-77. PubMed P.M.I.D.: 9886913.
Machado et al., "Evaluation of an Ultrasonic Method Applied to the Measurement of Blood Coagulation Time". Physiol. Meas., May 1997; 18(2):129-43. PubMed P.M.I.D.: 9183807.
Motovska et al., "Benefits and Risks of Clopidogrel Use in Patients with Coronary Artery Disease: Evidence from Randomized Studies and Registries". Clin. Ther., 2008; 30 Pt. 2:2191-202. J. Clinthera., 2008.12.001. Review. PubMed P.M.I.D.: 19281914.
Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15(6):652-9. PubMed P.M.I.D.: 18805846.
Nam et al., "Evaluation of the Roche CoaguChek XS Handheld Coagulation Analyzer in a Cardiac Outpatient Clinic". Ann. Clin. Lab. Sci., 2008 Winter; 38(1):37-40. PubMed P.M.I.D.: 18316780.
Pallister CJ, Watson MS (2010). Haematology. Scion Publishing. pp. 336-347. ISBN 1-904842-39-9.
Patent Examination Report issued in Australian Application No. 2012364908, dated Jul. 23, 2016, 4 pages.
Peeters et al., "Ultrasonic Measurements of Coagulation and Fibrinolysis". J. Clin. Pathol., May 1964; 17:320-3. PubMed P.M.I.D.: 14159472; PubMed Central P.M.C.I.D.: PMC480759.
Petition for Inter Partes Review of U.S. Pat. No. 9,272,280 B2, 28 Pages.
Petition for Inter Partes Review of U.S. Pat. No. 9,410,971 B2, 51 Pages.
Petition for Inter Partes Review of U.S. Pat. No. 9,410,971, dated Nov. 30, 2017, 74 pages.
Decision Denying Petitioner's Request for Rehearing for Inter Partes Review of U.S. Pat. No. 9,410,971, entered Nov. 3, 2017, 7 pages.
Patent Owner's Response to the Decision to Institute Inter Partes Review of U.S. Pat. No. 9,410,971, entered Dec. 1, 2017, 59 pages.
Declaration of Dr. Scott Diamond, Ph.D., dated Dec. 1, 2017.
Price et al., "Prognostic Significance of Post-Clopidogrel Platelet Reactivity Assessed by a Point-ofCcare Assay on Thrombotic Events after Drug-Eluting Stent Implantation". Eur. Heart J., Apr. 2008; 29(8):992-1000. PubMed P.M.I.D.: 18263931.
Prisco et al. "Point-of-Care Testing of Hemostasis in Cardiac Surgery". Thromb. J. May 6, 2003; 1(1):1, 10 pages. PubMed P.M.I.D.: 12904262; PubMed Central P.M.C.I.D.: PMC166118.
Rugeri et al."Diagnosis of early coagulation abnormalities in trauma patients by rotation thrombelastography", Journal of Thrombosis and Haemostasis, 5, 2007, pp. 289-295.
Rumbaut et al. "Platelet-Vessel Wall Interactions in Hemostasis and Thrombosis" (2010), San Rafael (CA): Morgan & Claypool Life Sciences, 5 pages.
Ruzicka, K., et al. Evaluation of Bedside Prothrombin Time and Activated Partial Thromboplastin Time Measurement by Coagulation Analyzer Coagucheck Plus in Various Clinical Settings. Throm. Res., 87(5)1997 pp. 431-440. See also, Hillman, R., 1988 U.S. Pat. No. 4,756,884. Capillary Fill Device.
S. Kozek-Langenecker, Intensive Care Medicine, Annual Update 2007, Monitoring of Hemostasis in Emergency Medicine, pp. 847-860, Springer New York.

Scharbert et al., "Evaluation of the Platelet Mapping Assay on Rotational Thromboelastometry ROTEM". Platelets. Mar. 2009;20(2):125-30. PubMed P.M.I.D. 19235055.
Schochl et al., "Use of rotation thromboelastometry (ROTEM) to achieve successful treatment of polytrauma with fibrinogen concentrate and prothrombin complex concentrate", Anaesthesia, 2010, 65, pp. 199-203.
Taborski et al., "Analytical Performance of the New Coagulation Monitoring System INRatio for the Determination of INR Compared with the Coagulation Monitor Coaguchek S and an Established Laboratory Method" J. Thromb.Thrombolysis. Oct. 2004; 18(2):103-7. PubMed P.M.I.D.: 15789176.
Third party observation filed in European Patent Application No. 11766842.6, dated Mar. 6, 2016, 10 pages.
Third party observation filed in U.S. Appl. No. 15/202,059, Nov. 30, 2016, 40 pages.
Tripodi et al., "International Sensitivity Index Calibration of the Near-Patient Testing Prothrombin Time Monitor, ProTime". Am. J. Clin. Pathol., Feb. 2003;119(2):241-5. PubMed P.M.I.D.: 12579994.
Versteeg et al., "New Fundamentals in Hemostasis", Physiol. Rev. Jan. 2013; 93(1):327-58. Review. PubMed P.M.I.D.: 23303912.
Wolff et al., "Aspirin for the Primary Prevention of Cardiovascular Events: an Update of the Evidence for the U.S. Preventive Services Task Force". Ann. Intern. Med., Mar. 17, 2009; 150(6):405-10. Review. PubMed P.M.I.D.: 19293073.
Examination Report issued in Australian Application No. 2012364908, dated Jun. 27, 2017, 5 pages.
Trial Board Order for Inter Partes Review of U.S. Pat. No. 9,272,280 B2, 13 pages.
Trial Board Order for Inter Partes Review of U.S. Pat. No. 9,410,971 B2, 27 pages.
Office Action received in U.S. Appl. No. 15/357,492, dated Jun. 22, 2017.
Office Action received in co-pending U.S. Appl. No. 15/202,059, dated Oct. 4, 2016.
Office Action received in co-pending U.S. Appl. No. 15/202,059, dated Jul. 13, 2017.
Advisory Action received in co-pending U.S. Appl. No. 15/202,059, dated Sep. 21, 2017.
Office Action received in co-pending U.S. Appl. No. 15/202,059, dated Jan. 12, 2018.
Office Action received in co-pending U.S. Appl. No. 15/644,124, dated Sep. 7, 2017.
Office Action received in co-pending U.S. Appl. No. 15/644,124, dated Nov. 29, 2017.
Office Action received in co-pending U.S. Appl. No. 15/644,124, dated Feb. 6, 2018.
Patent Owner's Response to the Decision to Institute Inter Partes Review of U.S. Pat. No. 9,272,280, dated Dec. 1, 2017, 39 pages.
Declaration of Patrick D. Mize, Ph.D., dated Nov. 30, 2017.
Table of Prior Art Devices.
Görlinger, K., et al., "Perioperative Coagulation Management and Control of Platelet Transfusion by Point-of-Care Platelet Function Analysis," Transfus Med Hemother 34:396-411 (2007).
Rahe-Meyer, N. et al., Multicentric comparison of single portion reagents and liquid reagents for thromboelastometry. Blood Coagul Fibrinolysis Apr. 2009;20(3):218-22. PubMed P.M.I.D.: 19657320.
Stony Brook Portable Field Viscometer (for a quick 'Pass' or 'Fail' decision).
Faulds, D. et al., "Abciximab (c7E3 Fab). A review of its pharmacology and therapeutic potential in ischaemic heart disease; Drugs 583-98 (1994)" PubMed P.M.I.D.: 7528131 ("Faulds 1994").
EP Extended Search Report, dated Oct. 24, 2016, in copending International Application No. PCT/US2012/025270.
Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18. 1994.
Wolberg AS. Plasma and cellular contributions to fibrin network formation, structure and stability. Haemophilia. May 2010 16:7-12.

(56) References Cited

OTHER PUBLICATIONS

Janus TJ, Lewis SD, Lorand L, Shafer JA. Promotion of thrombin-catalyzed activation of factor XIII by fibrinogen. Biochemistry. 1983;22(26):6269-72.
Niewiarowski S, Stewart GJ, Nath N, Sha AT, Lieberman GE. ADP, thrombin, and Bothrops atrox thrombinlike enzyme in platelet-dependent fibrin retraction. The American journal of physiology. 1975;229(3):737-45.
Janmey PA, Erdile L, Bale MD, Ferry JD. Kinetics of fibrin oligomer formation observed by electron microscopy. Biochemistry. 1983;22(18):4336-40.
Blattler W, Straub PW, Peyer A. Effect of in vivo produced fibrinogen-fibrin intermediates on viscosity of human blood. Thrombosis research. 1974;4(6):787-801.
Weisel JW. The mechanical properties of fibrin for basic scientists and clinicians. Biophysical Chemistry. 2004;112(2-3):267-276.
Cuisset T, Frere C, Poyet R, et al. Clopidogrel response: Head-to-head comparison of different platelet assays to identify clopidogrel non-responder patients after coronary stenting. Archives of Cardiovascular Diseases. 2010;103(1):39-45.
Multiplate® Analyzer Product Guide.
VerifyNow® Product Guide.
Kuntamukkula MS, McIntire L V, Moake JL, Peterson DM, Thompson WJ. Rheological studies of the contractile force within platelet-fibrin clots: effects of prostaglandin E1, dibutyryl-cAMP and dibutyryl-cGMP. Thrombosis research. 1978;13(6):957-69.
Plotkin, et al., The Journal of Trauma: Injury, Infection, and Critical Care. 2008.
Fundamentals of biomechanics Equiolobrium, Motion, and Deformation. 2nd Edition. Eds. Nihat Özkaya and Margareta Nordin. (Springer Science+Business Media, Inc., New York, NY). Chapter 9 "Mechanical Properties of Biological Tissues." pp. 196-218. 1999.
Instrument Engineers' Handbook. Fourth Edition. Ed. Bela G. Liptak (CRC Press). Process Measurement and Analysis vol. 1, Chapter 8 Analytical Instrumentation. 8.53 Rheometers, 1628-1636, 2003.
Thurston GB. Viscoelasticity of Human Blood. Biophysical Journal. 1972; 12:1205-1217.
Webster, Medical Instrumentation: Application and Design, New York: John Wiley & Sons, 1998, 6 pages.
Patent Owner's Preliminary Response to Petition Requesting Inter Partes Review of U.S. Pat. No. 9,410,971, dated Feb. 14, 2018, 33 pages.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Lang et al., "Multi-centre investigation on reference ranges of ROTEM thromboelastometry," Blood Coagulation and Fibrinolysis, 2005, 16:301-310.
Lang et al., "Possibilities and limitations of thromboeleastometry/thromboelastography," Downloaded from www.haemostaseologie-online.com on Mar. 6, 2018 | IP: 24.163.60.123.
Notice of Allowance issued for U.S. Appl. No. 15/202,059, dated May 23, 2018.
Corrected Notice of Allowance issued for U.S. Appl. No. 15/202,059, dated Jun. 22, 2018.
Examination Report issued for Australian Application No. 2017248548, dated Jul. 9, 2018.
Office Action issued for U.S. Appl. No. 15/904,984, dated Jul. 12, 2018.
Office Action issued for Canadian Application No. 2,823,729, dated Mar. 9, 2018.
Office Action issued for Canadian Application No. 2,823,729, dated Nov. 14, 2018.
Office Action issued for Canadian Application No. 2,823,729, dated Aug. 14, 2019.
Office Action issued for Chinese Application No. 2017101635956, dated Jul. 17, 2018.
Office Action issued for Chinese Application No. 2017101635956, dated Apr. 26, 2019.
Office Action issued for Chinese Application No. 2017101635956, dated Sep. 27, 2019.
Notice of Grant issued for Chinese Application No. 2017101635956, dated Jan. 13, 2020.
Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2:763-8.
Shore-Lesseron., Evidence Based Coagulation Monitors: Heparin Monitoring, Thromboelastography, and Platelet Function. Sem. Cardiothoracic Vasc. Anesthesia., Mar. 2005; 9(1):42-52.
Moake J Overview of Hemostasis. Merck Manuals 2016 http://www.merckmanuals.com/professional/hematology-and-oncology/hemostasis/overview-of-hemostasis.
Theusinger, O.M., Nürnberg, J., Asmis, L.M., Seifert, B., Spahn, D.R., Rotation thromboelastometry (ROTEM) stability and reproducibility over time. Eur. J. Cardiothorac. Surg. 2010; 37:677-83.
Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6(1):1-12.
Fundamentals of biomechanics Equiolobrium, Motion, and Deformation. 3rd Edition. Eds. Nihat Özkaya and Margareta Nordin. (Springer Science+Business Media, Inc., new York, NY). Chapter 15 "Mechanical Properties of Biological Tissues." pp. 221-236. 2012.
Conduct of Proceeding for Inter Partes Review of U.S. Pat. No. 9,272,280 B2 dated Apr. 26, 2018, 3 pages.
Petitioner's Supplemental Reply for Inter Partes Review of U.S. Pat. No. 9,272,280 B2 dated May 18, 2018, 10 pages.
Conduct of Proceeding for Inter Partes Review of U.S. Pat. No. 9,410,971 dated Apr. 26, 2018, 3 pages.
Conduct of Proceeding for Inter Partes Review of U.S. Pat. No. 9,410,971 dated May 24, 2018, 5 pages.
Trial Paper for Inter Partes Review of U.S. Pat. No. 9,272,280 B2 dated Jul. 11, 2018, 10 pages.
Trial Paper for Inter Partes Review of U.S. Pat. No. 9,410,971 dated Jul. 11, 2018, 10 pages.
Trial Paper for Inter Partes Review of U.S. Pat. No. 9,410,971 dated Aug. 28, 2018, 3 pages.
Petition for Inter Partes Review for U.S. Pat. No. 9,915,671 dated Apr. 20, 2018, 76 pages.
Patent Owner's Preliminary Response for Inter Partes Review for U.S. Pat. No. 9,915,671 dated Jul. 20, 2018, 14 pages.
Weiss HJ, Aledort LM, Kochwa S., The effect of salicylates on the hemostatic properties of platelets in man. J Clin Invest. Sep. 1968;47(9):2169-80.
Kozek-Langenecker S. Monitoring of Hemostasis in Emergency Medicine in Intensive Care, Annual Update 2007 Ed: Vincent JL.
Trial Paper for Inter Partes Review of U.S. Pat. No. 9,410,971 dated Oct. 2, 2017, 11 pages.
Trial Paper for Inter Partes Review of U.S. Pat. No. 9,410,971 dated Dec. 1, 2017, 4 pages.
Declaration of Scott Diamond for Inter Partes Review of U.S. Pat. No. 9,915,671 dated Apr. 20, 2018, 200 pages.
Final Written Decision for Inter Partes Review of U.S. Patent 9,410,9710, dated Feb. 13, 2019, 55 pages.
Declaration of John Avila for Inter Partes Review of U.S. Pat. No. 9,915,671, dated Jan. 4, 2019, 38 pages.
Decision to Institute for Inter Partes Review of U.S. Pat. No. 9,915,671, dated Oct. 5, 2018, 27 pages.
Patent Owner's Response for Inter Partes Review of U.S. Pat. No. 9,915,671, dated Jan. 4, 2019, 37 pages.
Declaration of Frank M. Laduca, Ph.D, dated Feb. 21, 2019, 117 pages.
Petition for Post-Grant Review of U.S. Pat. No. 9,977,039, dated Feb. 21, 2019, 95 pages.
Final Written Decision for Inter Partes Review of U.S. Pat. No. 9,272,280, dated Feb. 13, 2019, 25 pages.
Nielson V, A Comparison of the Thrombelastograph and ROTEM, Blood Coagulation and Fibrinolysis 18:3, 247-252, 2007.
Declaration of Frank M. Laduca, Ph.D., FAHA, dated Apr. 24, 2019, 130 pages.

(56) References Cited

OTHER PUBLICATIONS

Hanecke, P and Klouche, M, Thrombelastography Today: Practicability and Analytical Power, Transfusion Medicine and Hemotherapy. 34. 421-428 (2007) ("Hanecke").

The 510(k) Summary for ROTEM delta, FDA clearance No. K083842 ("the 510(k) Summary for ROTEM delta").

The 510(k) Substantial Equivalence Determination Decision Summary for ROTEM delta, FDA clearance No. K083842 (the "Decision Summary for ROTEM delta").

User Manual (2007) for TEG 5000 Thrombelastograph Hemostasis System with TEG Analytical Software (TAS) Version 4.2.3 including an addendum (2008) for TEG Analytical Software (TAS) Version 4.3 (the "TEG 5000 User Manual").

*Instrumentation Laboratory Co. v. HemoSonics LLP*, IPR2017-00852, Paper No. 47 (PTAB Feb. 13, 2019) ("'852 FWD").

*Instrumentation Laboratory Co. v. HemoSonics LLP*, IPR2017-00855, Paper No. 55 (PTAB Feb. 13, 2019) ("'971 FWD").

Petition for Post-Grant Review of U.S. Pat. No. 10,031,144, dated Apr. 24, 2019, 104 pages.

Patent Owner's Notice of Appeal Inter Partes Review Case No. IPR2018-00950 U.S. Pat. No. 9,915,671B2, dated Feb. 4, 2020, 68 pages.

Patent Examination Report No. 1 for Australian Application No. 2017201112 dated Apr. 5, 2018, 2 pages.

Office Action issued for Canadian Application No. 2,826,770 dated Feb. 1, 2019, 4 pages.

Communication pursuant to Article 94(3) EPC dated Nov. 18, 2019, for European Application No. 12865373.0, 7 pages.

\* cited by examiner

CHARACTERIZATION OF BLOOD HEMOSTASIS AND OXYGEN TRANSPORT PARAMETERS

CROSS REFERENCE TO RELATED APPLICATIONS

This application is a continuation application of U.S. patent application Ser. No. 13/397,481, filed Feb. 15, 2012, which is currently pending and which claims the benefit of U.S. Provisional Application No. 61/443,084, filed Feb. 15, 2011. Each of these applications is incorporated by reference herein in its entirety.

BACKGROUND OF THE INVENTION

The formation of a blood clot and its successive dissolution, referred to as the hemostatic process, is required to arrest blood loss from an injured vessel. This process is the result of a delicate functional balance between plasma coagulation factors, platelets, and fibrinolytic proteins. Each of these elements plays an important role in activating/deactivating the others, and the appropriate stimuli are necessary to prevent excessive blood loss without causing inappropriate thrombosis. Disruption of this balance plays a significant role in the onset of potentially fatal conditions, including myocardial infarction, stroke, deep vein thrombosis, pulmonary embolism, and hemorrhage.

The hemostatic process is initiated by the activation and subsequent adhesion of platelets to the site of injury within the vessel wall. Activated platelets recruit other platelets and interact with fibrinogen in the blood plasma to form a platelet-plug that serves as the initial response to stop blood loss. Hemostasis then proceeds with a cascade of proteolytic reactions of the plasma coagulation proteins that ultimately form a three-dimensional network of fibrin that strengthens the platelet-plug. The fibrin chains are cross-linked and stabilized by the plasma factor XIIIa (FXIIIa). Platelets also have a central role in regulating the process of fibrin polymerization. The final step of hemostasis (i.e., fibrinolysis or clot dissolution) involves the activation of the plasma protein plasmin, which lyses the blood clot when its useful life is over. This cell-based model of hemostasis closely reflects the in vivo physiological process.

Hemostasis, the physiological control of bleeding, is a complex process incorporating the vasculature, platelets, coagulation factors (FI-FXIII), fibrinolytic proteins, and coagulation inhibitors. Disruption of hemostasis plays a central role in the onset of myocardial infarction, stroke, pulmonary embolism, deep vein thrombosis and excessive bleeding. Consequently, in vitro diagnostics (IVD) are critically needed to quantify hemostatic dysfunction and direct appropriate treatment. This need is particularly acute during cardiac surgeries requiring cardiopulmonary bypass (CPB), where post-surgical bleeding is a common complication requiring transfusion of blood products.

Existing IVDs include endpoint biochemical assays, platelet aggregation assays, and clot viscoelastic measurement systems. Endpoint biochemical assays such as the prothrombin time (PT) and the partial thromboplastin time (PTT) are widely used to assess coagulation. However, these tests measure only a part of the hemostatic process and operate under non-physiological conditions incorporating only the function of plasma. As a result of these limitations, complications such as postoperative bleeding often occur despite normal perioperative PT and PTT measurements.

Activated clotting time (ACT) is an endpoint assay that is most often applied in support of CPB. This assay applies strong initiation of the surface activation (intrinsic) pathway to quantify heparinization. Limitations of the ACT include its disregard for platelet function, lysis, and coagulation kinetics along with the use of large aliquots of whole blood (WB) (generally 2 mL) and moving mechanical parts. For these reasons, the ACT is used for rapid assessment of heparinization and associated protamine reversal with limited utility for additional applications.

Platelets play a crucial role in the progression of coagulation and quelling arterial bleeding. Furthermore, the modern cell-based theory of hemostasis recognizes that platelets play a modulating role in coagulation. Platelet function is monitored clinically via both central lab assays and point of care (POC) tests, which use anticoagulated WB. Both approaches are limited in that they use platelet aggregation as a proxy for overall platelet function. Furthermore, disabling coagulation, these methods neglect the interaction between platelets and the coagulation cascade.

Techniques that monitor the viscoelastic properties of WB, such as thromboelastography (TEG) and rotational thromboelastometry (ROTEM), circumvent many of the limitations of endpoint biochemical assays and platelet aggregation assays by measuring the combined effects of all components of hemostasis. TEG has been shown to diagnose hyperfibrinolysis in bleeding patients, indicate transfusion requirements better than standard biochemical assays, and reduce transfusion requirements during CPB when used with transfusion algorithms. While these tests offer valuable clinical information, the devices are typically complex to operate and difficult to interpret. Moreover, the TEG applies relatively large shear strains, which transgress the nonlinear viscoelastic regime, thereby disrupting clot formation. For these reasons, the TEG sees very limited utility as a POC test.

SUMMARY OF THE INVENTION

The present invention overcomes the problems of the prior art by providing a system for measuring a parameter of a blood sample. The system may include, for example, an ultrasonic signal generator, a receiver and a processor. The ultrasonic signal generator is configured to generate and direct an ultrasonic signal to interact with the blood sample. The receiver is configured to determine at least one characteristic of the ultrasonic signal that interacted with the blood sample. The processor is configured to determine, using the characteristic, at least one hemostasis parameter and at least on oxygen transport parameter.

The oxygen transport parameter may include HCT, HGB, MCV, RBC, MCHC, MCH and combinations thereof. The processor may be further configured to generate a corrected hemostasis parameter using the oxygen transport parameter.

The hemostasis parameter may be a TC1, TC2, angle, and estimated stiffness S. Also, the hemostasis parameter may be an index for a clinical parameter, such as (1) coagulation factors (intrinsic and/or extrinsic), (2) platelet function, (3) fibrinogen and (4) fibrinolysis.

The processor may also be configured to communicate the clinical parameter to guide transfusion, such as through a graphical user interface (GUI). The clinical parameter may be (1) fresh frozen plasma, (2) platelet concentrates, (3) cryoprecipitate, (4) antifibrinolytics, and (5) packed RBCs.

The processor may also be configured to communicate the HCT or other oxygen transport parameter. It could also compare the HCT to an assumed HCT and communicate a difference therebetween. Or, it could determine when the HCT is within a range affecting the parameter and communicate a warning about the parameter.

In addition, a system for evaluating a blood sample could include a processor configured to determine a hemostasis parameter from the blood sample and to determine at least one oxygen transport parameter from the same blood sample. The system may also include an ultrasound generator and a receiver. The receiver is configured to receive reflected sound from the blood sample and to convert the received sound into electrical signals. The hemostasis parameter is measured by quantifying the displacement induced within the blood sample by application of at least one pulse of ultrasound of sufficient intensity to induce measurable displacement within the blood sample.

A method includes measuring at least one hemostasis parameter from the blood sample. Also, the method includes measuring at least one oxygen transport parameter from the same blood sample.

A system for determining properties of at least one tissue sample may include a measurement system, a processor and an integrated aspect. The measurement system is configured to determine date characterizing the tissue sample. The processor is configured to receive the data and to determine at least one hemostasis parameter and at least one oxygen transport parameter using the data. The integrated aspect is configured to facilitate determination of the at least one hemostasis parameter and at least one oxygen transport parameter. The data, for example, may be generated by an application of force to the tissue sample.

The integrated aspect may be a common sample portion. The common sample portion is characterized by the hemostasis parameter and oxygen transport parameter. A sample container may be included to contain the common sample portion. The common sample portion may be a blood sample, for example.

The integrated aspect may also be a receiver of the measurement system, wherein the receiver is configured to determine displacement of the tissue sample.

The integrated aspect may also include an ultrasonic signal generator of the measurement system. It may be configured to generate and direct an ultrasonic signal to the tissue sample to induce the displacement. The processor may be configured to determine a stiffness of the tissue sample using the displacement. The stiffness can be used to determine the hemostasis parameter.

The data may also include a speed of sound through the tissue sample. The processor is configured to use the speed of sound to determine the oxygen transport parameter. The data may also include attenuation of the ultrasonic signal through the tissue sample and use the attenuation to determine the oxygen transport parameter. The speed of sound and/or attenuation can also be used to calibrate the system.

The ultrasonic signal generator may be configured to adaptively adjust the ultrasonic signal. For example, it may generate a convoluted pulse and the process may be configured to process a corresponding correlation function. For example, the convoluted pulse may be convolved with a Barker code.

Also, the measurement system may operate in two phases. A first phase determines first phase data and a second phase determines second phase data. The first phase data is used to determine the hemostasis parameter. The second phase data is used to determine the oxygen transport parameter. The phases may occur in series.

Also, the measurement system may be configured to determine the data by querying a plurality of channels. And, the system may be configured to operate in a plurality of cycles. Each cycle includes acquisition of the data by the measurement system and processing of the data by the processor.

The processor may be further configured to adjust the hemostasis parameter using the oxygen transport parameter.

The integrated aspect may also include a common portion of the data used by the processor to determine the oxygen transport parameter and the hemostasis parameter.

The oxygen transport parameter may, for example, be one or more of HCT, HGB, MCV, RBC, MCHC and MCH.

The integrated aspect may also include an ultrasound transducer and receiver of the measurement system. The transducer and receiver may be positioned on opposite sides of the tissue sample.

Also, the processor may be configured to perform a physiological adjustment to the hemostasis parameter. For example, the physiological adjustment may be based on the oxygen transport parameter. Also, the processor may be configured to perform a physical adjustment to the hemostasis parameter. For example, the physical adjustment may be based on one of a speed or attenuation of a sound signal through the tissue sample.

The system may also include a GUI configured to display both the hemostasis parameter and the oxygen parameter simultaneously.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

FIGS. 19A-19G are schematic illustrations of an example cartridge for evaluating hemostasis;

DETAILED DESCRIPTION OF THE INVENTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

The present invention provides methods, apparatus and systems for performing what the present inventors have termed sonorheometry. Sonorheometry provides data about the mechanical properties of soft tissue. Furthermore, repeated measurements using sonorheometry enable characterization of changing properties over time. Sonorheometry is particularly well-suited to characterizing blood coagulation and clot dissolution (i.e., the hemostatic process). The present invention provides data about the mechanical properties of a developing and later dissolving clot without disrupting the underlying processes. The methods and techniques may be non-invasive or carried out in a laboratory setting after obtaining a sample from a patient, and are based on the application of acoustic radiation force to the tissue to be characterized.

An increased or decreased propensity to clot can be evaluated by observing the coagulation rate and mechanical characteristics of the developing clot at any time during formation and dissolution. This information may in turn allow clinicians to assess an individual's clotting behavior and to treat coagulation disorders appropriately. This information may also be used to evaluate whether a particular treatment and/or dosage is effective or needs to be changed, as subsequent testing according to the present methods (i.e., after a treatment has been administered) can be carried out to compare the results, thereby indicating the effect of the treatment.

I. Determination of Hemostasis Indexes

Figure 1A:
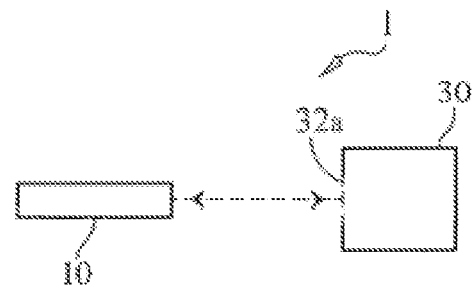
FIG. 1A is a schematic representation of the present invention useful for in vitro characterization of a soft tissue sample such as blood.

Referring now to FIG. 1A, an assembly 1 is schematically shown that is set up for testing soft tissue according to the present invention. An acoustic wave generating device 10 is positioned in alignment with container 30 to allow device 10 to irradiate a soft tissue contained within container 30. Device 10 may be mounted or fixed at a predetermined distance for the contents of the container 30 to receive focused acoustical waves from device 10. Thus, device 10 and container 30 are oriented to align the emission of acoustic waves from device 10 with a sample contained in container 30.

Figure 1B:
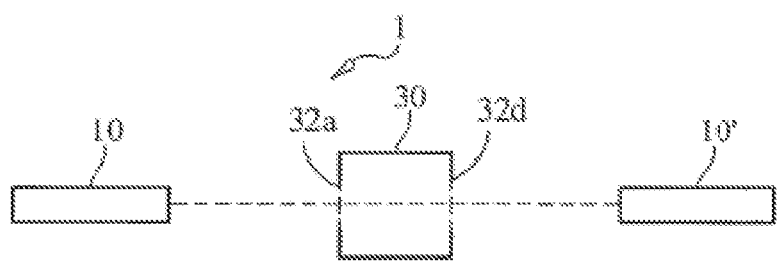
FIG. 1B is a modification of the arrangement shown in FIG. 1A in which an additional transducer is positioned on a side of the container opposite the device that is also shown in FIG. 1A.

Container 30 may be entirely acoustically transparent, or contains at least one window 32a that is acoustically transparent and that is aligned with the emission pathway of device 10. As one non-limiting example, container 30 may include a plastic cuvette having windows 32a and 32d, as shown in FIG. 1B, cut therethrough and covered with KAPTON® (polyimide) film or other at least partially acoustically permissive material.

It may be advantageous to place the acoustic window or windows of the sample container at some non-perpendicular angle relative to the direction of wave propagation so as to reduce the magnitude of received echoes from the interfaces with the window(s). Multiple measurements may be performed at the same time using an array of sample containers 30.

An array may either include multiple individual containers or a single container with multiple sample compartments. Additionally or alternatively, an array of transducers may be included in device 10, or an array of devices 10 may be used to make multiple measurements. Thus, for example, multiple transducers and/or multiple devices 10 may be provided to analyze multiple samples in parallel, wherein the multiple samples are contained in multiple individual containers or a single container with multiple sample compartments.

Assembly 1 may be submerged in a tank of water or other coupling medium to facilitate transmission of the acoustic waves. Alternatively, device 10 (or other acoustic emitter and receiver) may be placed in direct contact with the sample. Still further, device 10 may be adapted to deposit the sample directly in contact therewith, for example placing a drop (or other quantity) of blood on a transducer contained in device 10 or other application feature of device 10. In the case where a bath (of water or other coupling medium) is provided, the bath may be a constant temperature bath or other means may be provided to maintain a constant sample temperature.

In cases where no bath is used, it may be advantageous to place the sample in contact with a material of controlled temperature, so as to control the sample temperature. Another alternative is the use of device 10 invasively. For example, device 10 may be inserted intra-vascularly and delivered to the location of a stent to characterize any clotting that may be occurring as well as characterize the progression or stage of a clot that may be present.

Similar intravascular techniques can be applied for identifying and/or characterizing clot processes with regard to Deep Vein Thrombosis (DVT), as well as for other clotting events throughout the body, as long as the location is accessible by catheter or other delivery instrument, for example. Thus, not only are intravascular insertions, deliveries or locations made possible by the device, but the device may also be positioned at an intra-cavity location or other location inside of the body.

One could also apply the invention from outside the body and rather than looking at maximum displacement, look at the time constant of the displacement to characterize clot characteristics or evolution.

Device 10 includes an acoustic wave generating source capable of generating one or more pulses, at least one of which is of sufficient intensity to induce measurable physical displacement in the soft tissue contained in container 30. For example, device 10 may include one or more piezoelectric transducers capable of generating ultrasonic waves. Alternatively, device 10 may utilize an electric circuit to generate rapid heating and thereby generate acoustic energy.

Further alternatives may be employed for generating acoustic energy, including, but not limited to: an ultrasonic generator fabricated using microelectromechanical systems (MEMS); a capacitive micromachined ultrasound transducer; a laser used to heat a target material thereby generating acoustic energy, where the laser may be targeted on a permanent component of the assembly, or on a surface of the sample, for example. Still further alternatively, a transducer may be incorporated into the sample container 30 in lieu of providing it in the device 10, as in a case, for example, where a polymer transducer material such as PVDF may be glued right onto the surface of the sample container 30.

Device 10 further includes at least one sensor capable of measuring displacement or deformation induced by the acoustic waves as they are applied to the soft tissue sample and reflected by the soft tissue sample back to device 10. In this configuration, an ultrasound sensor may be used to track the motion of the sample as induced by at least one ultrasonic wave of sufficient intensity to induce displacement of the tissue.

Alternatively, tracking of the motion may be accomplished by means other than sensing reflected acoustic waves. For example, optical coherence tomography, a focused light interferometer or laser Doppler may be used to optically sense the displacement of the tissue induced by the one or more ultrasonic waves.

Device 10 may include one or more sensors for carrying out any of these optical methods or such sensors may be provided in equipment that is separate from device 10. Likewise, for acoustic sensing, the one or more sensors may be one and the same as the acoustic wave generator, or may be a separate component(s) and may take any of the forms described above with regard to the acoustic wave generating component. An ultrasonic transducer may be used to both apply ultrasonic waves to the soft tissue as well as to sense ultrasonic waves reflected back from the tissue. An adjoining processor (not shown in FIG. 1A) may be provided to control the timing of transmission of pulses and of receiving of echoes (reflected pulses) by device 10.

FIG. 1B shows an example wherein a second device 10' is positioned in alignment with device 10, but on the opposite side of container 30 compared to the location of device 10. In this example, container 30 may be entirely acoustically transparent, or contain at least two windows 32a and 32d that are acoustically transparent and that are aligned with the emission pathway of device 10 to permit emissions to pass through both windows 32a and 32d to be received by device 10'. System 1 shown in FIG. 1B, in addition to performing the measurements that the system of FIG. 1A performs, can also measure acoustic properties, including speed of sound and attenuation, which provide indirect measures of tissue microstructure and which may be used for calibration purposes.

Acoustic radiation force arises from two sources, a non-zero time-averaged sound pressure in the ultrasonic beam, and the momentum transported by the beam. The momentum transfer component of this force dominates under most conditions. This momentum transfer results from attenuation of the propagating ultrasound beam via both absorption and scattering. For the case of total absorption the applied radiation force is simply:

$$F=W/c \qquad (1)$$

where W is the acoustic power and c is the speed of sound in the medium. In the case of perfect reflection this radiation force is doubled. In both cases, radiation force acts along the direction of wave propagation.

In biological media absorption and reflection are neither total, nor isolated at interfaces. Rather, attenuation and reflection (in the form of scattering) occur throughout volumes of tissue. In these cases radiation force acts as a body force, with the force on a given volume simply equal to the sum of the force from absorption and that from scattering. If we assume that scattering in the tissue consists purely of backscatter, which is of course overly simplistic, then the radiation force applied to a given volume of tissue is:

$$F=Wa/c+2Ws/c \qquad (2)$$

where Wa is the absorbed ultrasound power and Ws is the scattered ultrasound power within the volume. If we further simplify by recognizing that only a fraction of the scattered energy is returned as backscatter, and that attenuation is dominated by absorption rather than scattering, then (2) can be simplified as:

$$F=Wa/c=(A/c)I_0(e^{-2\alpha f z_1}-e^{-2\alpha f z_2}) \qquad (3)$$

where A is the cross sectional area of the volume of interest (perpendicular to the axis of propagation), $I_0$ is the ultrasound intensity that would be observed in the absence of attenuation, $\alpha$ is the amplitude attenuation coefficient in Nepers per centimeter per MHz, f is the ultrasonic center frequency in MHz, and $z_1$ and $z_2$ are the ranges of the front and back of the volume in units of centimeters.

By utilizing two devices 10 and 10', wherein device 10 at least contains an emitter and device 10' contains at least a sensor for receiving the waves/pulses that pass through windows 32a, 32d the system can also measure the waves that pass from device 10 to device 10' and estimate acoustic properties of the sample being analyzed. Examples of acoustic properties that may be estimated include attenuation, scattering, and speed of sound during sonorheometry procedures. The data received by device 10' may be used to make predictions/estimations of the applied radiation force and compare experimentally determined displacements to predicted displacements.

Figure 1C:
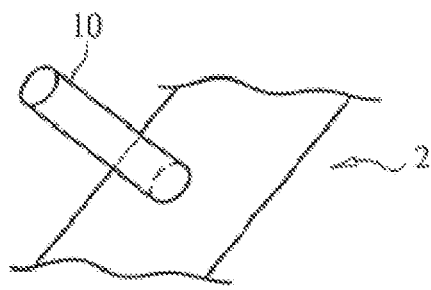
FIG. 1C schematically illustrates a non-invasive use of the present invention.

It should be noted that although FIG. 1A shows an example of apparatus for performing analysis in vitro (such as in a laboratory setting, or from a self-operated testing kit, for example) after taking a sample to be analyzed from a patient and depositing it in container 30. Alternatively, the present invention may also be practiced non-invasively, such as by applying acoustic waves from a device 10 transdermally through a patient (in vivo) to the targeted tissue to be analyzed, see FIG. 1C.

A single time frame analysis of one or more physical properties of the tissue may be made, or time series studies may be performed by applying the waves transdermally at different time periods, using the techniques described herein for the in vitro studies. Generally, the in vivo analyses would not involve administration of thrombin or other coagulant to a patient. However time studies may be done to test the effectiveness of an anti-clotting treatment regimen for example. Similarly, time studies may be done to test the effectiveness of a pro-clotting regimen given to a patient to increase the ability of the blood to clot, such as in the case of a hemophiliac, for example. Likewise, the administration of thrombin is not necessarily required for time studies in vitro, as there are other techniques that may be substituted to initiate coagulation, such as snake venom, kaolin, celite, tissue factor, the use of ground glass to initiate coagulation, etc.

Non-invasive applications of the current invention include characterizing a stage of development of a blood clot by generating a series of acoustic pulses and transdermally directing the series of pulses into the blood such that at least one of the pulses are of sufficiently high intensity to induce physical displacement of the blood, receiving at least two pulses, including at least one pulse reflected from the blood to establish a baseline and another pulse reflected from the blood to estimate at least one characteristic of the physical displacement induced by the waves.

Alternatively, the at least two pulses identified above as being used for establishing baseline and estimating a characteristic resulting from the physical displacement of the sample, do not necessarily have to be reflected from the blood/sample. For example, if the sample is contained within membranes that move with the movement of the blood/sample or in a container 30 that is sufficiently flexible (such as a membranous container, for example) to move with the movements of the blood/sample, then the at least two pulses could alternatively be those reflected from the surfaces of the flexible sample container or other membranes placed within the sample, as the movement of the sample (e.g., development of the clot) will alter the position of the surfaces or membranes.

The at least one estimate may be compared to previously generated data to gauge the stage of development of the blood clot being analyzed. The previously generated data may be reference data, such as generated across a larger number of patients and then averaged to determine normal characteristics, as well as to find average levels for characterizing different stages of clotting for example. Optionally, one or more algorithms, techniques or statistical processes may be applied to the at least one estimate to correct for attenuation, scatter and/or other variables before making comparisons to the previously generated data and/or database.

Additionally, or alternatively, the prior data or previously generated data may be data generated from one or more previous applications of the present invention to the same patient for the same tissue at prior times. This approach may be used to develop a history, to show the progression of the development of the clot for example. Of course, the in vitro apparatus described herein could be used to carry out the same tests outside of the body, such as in a laboratory or a patient's home test kit.

Still further evaluation of the effectiveness of an anti-clotting treatment may be performed, such as by evaluating the blood prior to application of the treatment by generating a series of acoustic pulses and directing the series of pulses into the blood such that at least one of the pulses is of sufficiently high intensity to induce physical displacement of the blood, receiving at least two pulses reflected from the blood to establish a baseline and to estimate at least one characteristic of the physical displacement induced by the waves, and then repeating these steps at least one time after administration of the treatment.

As noted earlier, alternative sensing or receiving steps may be taken to track the movement of the blood, such as by using any of the alternative sensing techniques described above, e.g., laser Doppler, optical coherence tomography, etc. Repeated applications of the steps at predetermined time intervals may be performed if needed to ensure a stabilization of the properties measured, as a result of the treatment. Alternatively, the analysis may indicate that a larger or smaller dose of treatment is needed, or that the treatment is ineffective for a particular patient.

Alternatively, evaluation of the effectiveness of an anti-clotting treatment may be performed by carrying out the analysis steps a number of times after treatment, at predetermined time periods after the administration of the treatment, for example. The results generated from each iteration can then be compared and analyzed to note any changes in the at least one physical characteristic that is being measured/estimated.

Maintenance monitoring can be carried out by the same techniques noted, wherein a patient can be periodically tested to ensure that a clot has not progressed further and/or is dissolving.

Figure 2:
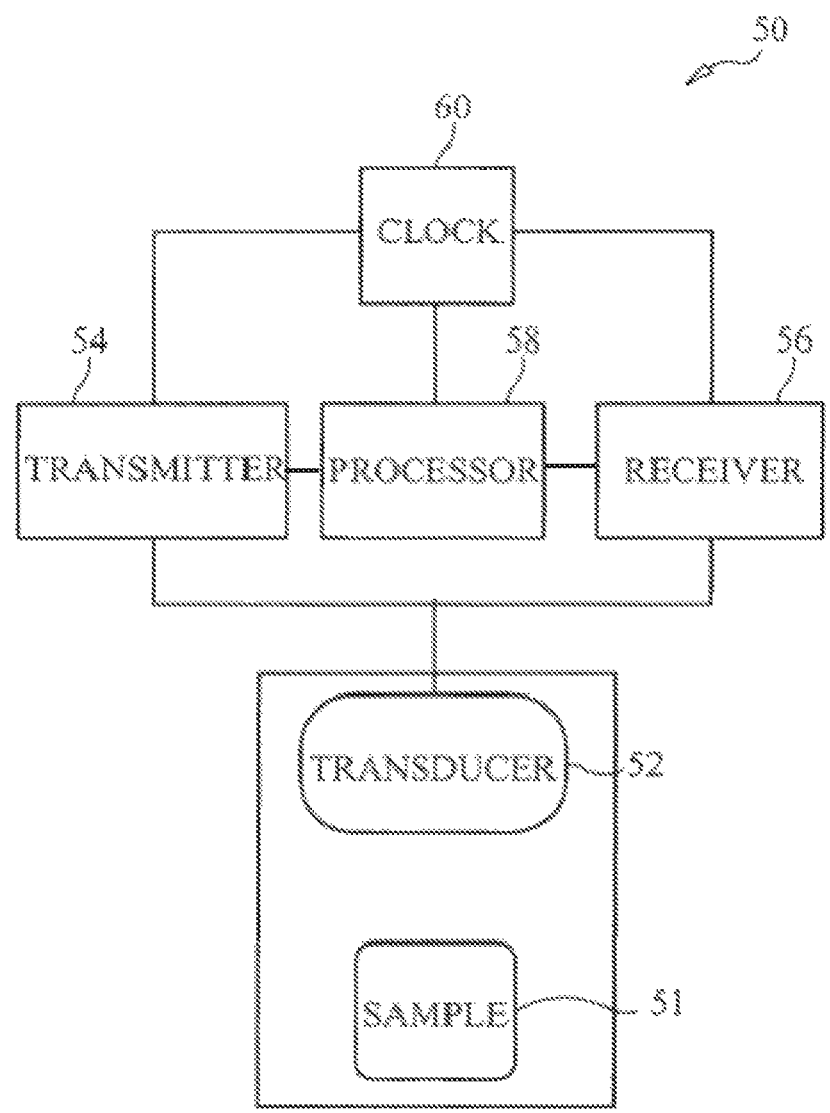
FIG. 2 is a schematic representation of a system for characterization of at least one physical property of soft tissue.

FIG. 2 shows a schematic representation of an example of a system 50 for characterization of changes in physical properties of soft tissue over time. In this example, a transducer 52, such as may be contained in a device 10 as described above, or directly mounted, fixed to or integral with a container holding a sample 51, for example, is connected to a transmitter 54 as well as receiver 56, both of which are controlled by processor 58 and timed by clock 60.

Clock 60 is provided to control the timing of application of radiation to the sample as generated by transmitter and converted to the acoustic energy at transducer 52, as well as the timing of receiving and interpreting the reflected waves (echoes), by conversion through transducer 52 and receipt of the converted signals at receiver 56, all of which is controlled by one or more processors/microprocessors 58.

Displacements of the soft tissue may be induced by delivering one or more acoustic pulses according to a predetermined frequency through device 10.

The displacements may be estimated by applying one or more signal processing algorithms (e.g., minimum sum squared difference motion tracking algorithm, etc.) to the acquired echoes of every nth delivered pulse where "n" is a predefined integer. Alternatively, the signal processing algorithms may be applied to every pulse received. Similarly, algorithms may be applied at every nth time interval for optical waves received.

Parameter measurement may be initiated at a predetermined time after one or more coagulation reagents are added to the sample, and such measurements may be repeatedly performed, e.g., once after each passage of a pre-designated time period or according to pre-defined time intervals for measurement. At each acquired time lapse, a time-displacement curve may be generated from which the viscoelastic parameters of the sample can be determined.

Figure 3:
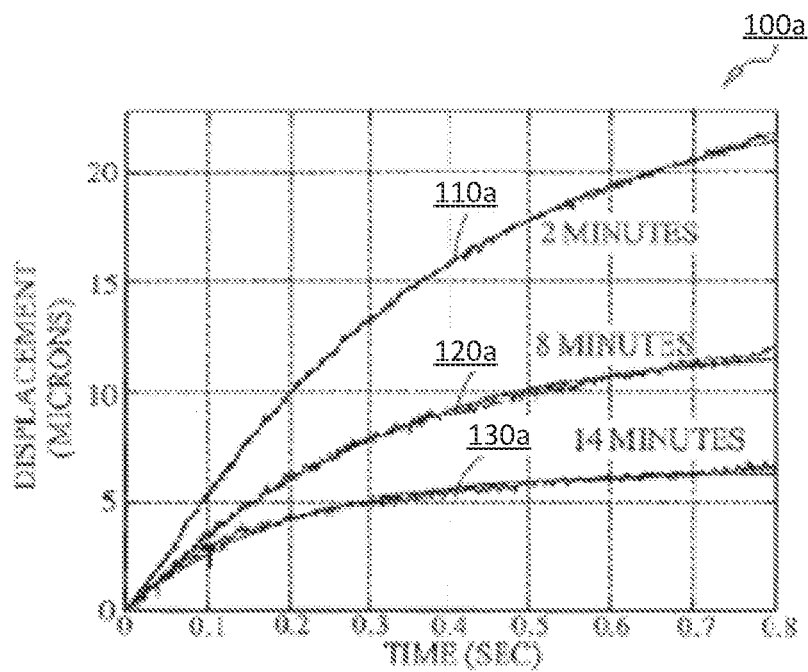
FIG. 3 shows a series of time-displacement curves comparing values found by fitting a model to values obtained using an embodiment of the present apparatus.
Figure 4:
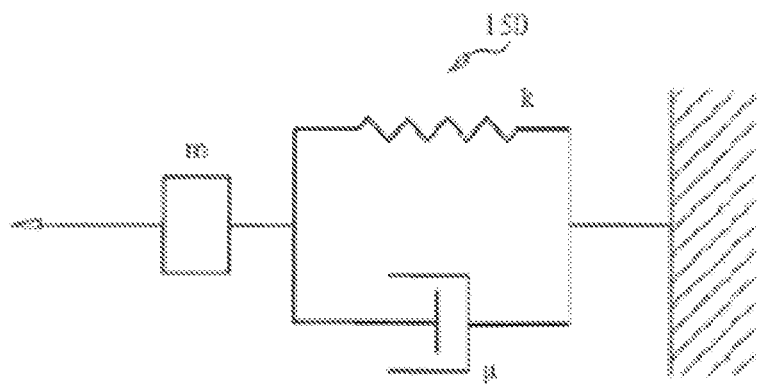
FIG. 4 is a symbolic representation of a modified Voigt model used as a model to characterize the behavior plotted in FIG. 3.

FIG. 3 is a graph 100a showing a set of time-displacement curves 110a, 120a, 130a obtained during coagulation of a blood sample using the techniques described. Curves 110a, 120a and 130a are superimposed on accompanying model predictions, where the mechanical properties of the forming thrombus are modeled by a modified Voigt model 150 as shown in FIG. 4. Experimental results and theoretical predictions show excellent agreement. The basis of the model from which the mechanical parameters are derived is the Voigt model in series with an inertial component. It should be noted that this is not an independent model. Rather, it is a parametric fit. The model is applied to determine the parameter values that give the best fit.

The modified version 150 of the Voigt model may be used to model the viscoelastic response of blood to acoustic radiation force from which mechanical parameters of the blood may be estimated. Model 150 includes an inertial component "m" in series with the traditional Voigt model, which includes a spring k in parallel with a dashpot as shown in FIG. 4. The governing differential equation for the model is:

$$F(t) = kx(t) + \mu dx(t)/dt + md^2x(t)/dt^2 \quad (4)$$

where F(t) is the applied force as a function of time, x(t) is the induced displacement as a function of time, k is the elastic constant, $\mu$ is the viscous constant, and m is the inertial component.

System 50 applies radiation force by transmitting a series of pulses to the same location in the blood sample. Assuming that the pulse-to-pulse interval is much shorter than the time constant of the blood's mechanical response, the forcing function may be modeled as a temporal step function as follows:

$$F(t) = Au(t) \quad (5)$$

where A is the force amplitude. Substituting equation (5) into equation (4) and solving for the displacement yields:

$$x(t) = \quad (6)$$

$$\frac{\zeta = \sqrt{\zeta^2 - 1}}{2\sqrt{\zeta^2 - 1}} s \cdot e^{\left(-\zeta + \sqrt{\zeta^2 - 1}\right)\omega k} + \frac{\zeta - \sqrt{\zeta^2 - 1}}{2\sqrt{\zeta^2 - 1}} s \cdot e^{\left(-\zeta - \sqrt{\zeta^2 - 1}\right)\omega k} + s$$

where $\zeta$ is the damping ratio, $\omega$ is the natural frequency (in radians per second) and s is the static sensitivity. These parameters are defined as:

$$\zeta = \frac{\mu}{2\sqrt{k \cdot m}} \quad (7)$$

$$\omega = \sqrt{\frac{k}{m}} \quad (8)$$

$$s = \frac{A}{k} \quad (9)$$

In the examples described herein, the force scaling constant A was not measured. Thus the time-displacement data in this situation can only be used to solve for relative parameters. To address this limitation, the equations (7), (8) and (9) are redefined according to the following equations (10), (11) and (12) using relative measures of elasticity $k_r$, viscosity $\mu_r$, and mass $m_r$:

$$\zeta = \frac{\mu_r}{2\sqrt{k_r \cdot m_r}} \quad (10)$$

$$\omega = \sqrt{\frac{k_r}{m_r}} \quad (11)$$

$$s = \frac{1}{k_r} \quad (12)$$

where $k_r = k/A$, $\mu_r = \mu/A$ and $m_r = m/A$.

Although the viscosity, elasticity and inertia are measured as force-dependent parameters, the natural frequency and the damping ratio still remain force-free or force-independent parameters. It is further possible to define a third force-independent parameter, i.e., the time constant $\tau$ as:

$$\tau = \frac{\mu_r}{k_r} \quad (13)$$

The fact that the actual data shown in FIG. 3 waivers or oscillates somewhat about the model data curves suggest that a different model might be used to even more closely model the behavior. In one possible modification, a dashpot would be placed in series with the model shown in FIG. 4. However, the model of FIG. 4 accurately described the response of the blood during formation of a clot with correlation between the data and the model of FIG. 3 being greater that 99% in most of the cases analyzed.

Alternatively, among the parameters obtained by the curve fitting, it is possible to use the estimated displacement magnitude at 1 second as a qualitative measure of the mechanical properties (i.e., stiffness) of the sample. When blood is in viscous fluid state, the displacement at 1 second is high. As the blood coagulates this displacement decreases relative to the generation of the fibrin mesh and activity of platelets. The value increases again during the process of fibrinolysis.

The displacement values obtained at 1 second for each data acquisition are compiled to form a curve showing relative stiffness as a function of time. This curve characterizes hemostasis and can be further processed to estimate direct indices of hemostatic function (See, e.g., FIG. 9). Other curves, using other reagents, may also be employed to facilitate estimation of, or separately determine, the hemostatic indices.

Indices of hemostasis are calculated by fitting a sigmoidal curve to the stiffness-time curve and evaluating the first derivative of the curve as described in Mauldin F W, Viola F et al. *Adaptive force sonorheometry for assessment of whole blood coagulation*. Clinical Chimica Acta 2010; 411: 638-644. For example, the times to clot TC1 and TC2 are calculated based on a threshold value of the derivative curve (20% of the minimum value), and are indicative of the beginning and ending phase of fibrin polymerization. The clotting slope CFR is the maximum of the derivative curve and is indicative of the rate of fibrin polymerization. Additionally or alternatively to calculation of CFR as described, an angle θ can be defined as the slope of the line between $TC_1$ and $TC_2$. The stiffness S is estimated from the stiffness curve 3 minutes after TC2. S depends upon platelet function and the final stiffness of the fibrin network. Identical methods and indices are calculated for the fibrinolytic process. In particular the times $TL_1$ and $TL_2$ can be defined to represent the initial and final phases of the fibrinolytic process and the consequent dissolution of the fibrin network (time to lysis).

A summary of the parameters generated for each test well is presented in the table below:

TABLE I

| Parameter | Information provided | Dependent upon |
| --- | --- | --- |
| $TC_1$, $TC_2$ | Measure initial and final fibrin formation | Function of fibrinogen and other coagulation factors |
| S | Fibrin and platelet activity | Function of fibrin network and platelet aggregation |
| CFR, θ | Rate of fibrin polymerization | Function of fibrinogen and other coagulation factors |
| $TL_1$, $TL_2$ | Clot dissolving process | Function of fibrinolytic proteins of the plasma |

In order to isolate the four main components of hemostasis, four sonorheometry measurements are performed in parallel using a combination of agonists and antagonists reagents. In a possible embodiment, test well 1 might have kaolin powder to activate coagulation through the intrinsic pathway. Test well 2 might have a combination of kaolin and abciximab (ReoPro) to inhibit platelet aggregation. Test well 3 might have abciximab and thrombin to activate coagulation through the common pathway. Test well 4 might have tissue factor to activate coagulation through the extrinsic pathway. The measurements in each well are combined to form indices of hemostasis as shown in the table below:

TABLE II

| Output | Method |
| --- | --- |
| Coagulation factors Index (Intrinsic Pathway) | Time to clot $TC_1$ in well #1 |
| Coagulation factors Index (Extrinsic Pathway) | Time to clot $TC_1$ in well #4 |
| Platelets Index | Stiffness S differential between well #1 and well #2 |
| Fibrinogen Index | Stiffness S in well #3 |
| Fibrinolysis Index | Time to lysis $TL_1$ in well #4 |

Example

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Blood samples were obtained from a peripheral vein of the arm of a patient into six 1.8 ml Vacutainers (Becton Dickinson, Franklin Lakes, N.J.) containing 3.2% (0.105M) sodium citrate to prevent coagulation within the tubes. The first tube was discarded, while the remaining tubes were placed on a rocker table and analyzed sequentially starting thirty minutes after the draw. For all the experiments described here, samples were obtained from a total of eight volunteers (four male and four female) with age range of twenty-three to thirty years (mean and standard deviation of 25.75±3.3 years) and with no history of thrombotic or hemorrhagic disorders. Ultrasound pulses having 10 Mhz center frequency were applied, pulse repetition frequency (PRF) was adaptively adjusted with the range of about 25 Hz to about 12.8 kHz. Automated measurements having a one second acquisition time were performed every six seconds.

In a typical experiment, 1 ml of citrated blood was pipetted into a 4 ml clear polystyrene cuvette along with 0.5 mg of kaolin activator to start coagulation through activation of the intrinsic pathway and 62 µl of 0.2M $CaCl_2$ to reverse the anticoagulant effect of the sodium citrate. Other reagents were also added as required by the specific study performed. Phosphate Buffer Saline (PBS) solution was added to maintain identical blood dilution. Sonorheometry data acquisition was initiated one minute after all the reagents were pipetted into the sample, and measurements were performed every six seconds.

Gly-Pro-Arg-Pro (GPRP) was obtained from Calbiochem (EMD Chemicals Inc., Gibbstown, N.J.) with 99.1% purity as determined by HPLC. GPRP was dissolved in PBS into 100 mM stock. Kaolin was obtained in powder form (Sigma Aldrich, St. Louis, Mo.) and suspended in sterile sodium chloride solution (Becton Dickinson, Franklin Lakes, N.J.). Monoclonal antibody abciximab (ReoPro, Eli Lilly and Company, Indianapolis, Ind.) was obtained in a concentration of 2 mg/ml. The original solution was diluted by a factor of five by adding 200 µL of PBS into 50 µl of the original ReoPro solution. The serine protease abbokinase (urokinase-type Plasminogen Activator, or uPA, Hyphen Biomed, Neuville-sur-Oise, France) was obtained in a concentration of 1 unit/W.

Pulse-to-pulse time delays were estimated using a spline-based estimator as described in Viola F, Walker W F. *A Spline Based Algorithm for Continuous Time Delay Estimation Using Sampled Data*. IEEE Trans Ultrason Ferroelect Freq Cont 2005; 52:80-93 and assembled to generate time-displacement curves, similar to those depicted in FIG. 3. The value of the induced displacement at 1 second was extrapolated from each curve, and the extrapolated displacement values were then normalized by their corresponding PRF and combined to form a stiffness vs. time curve similar to that shown in FIG. 9.

Results

Assessment of Coagulation Plasma Factors and Fibrin Polymerization

Figure 10:
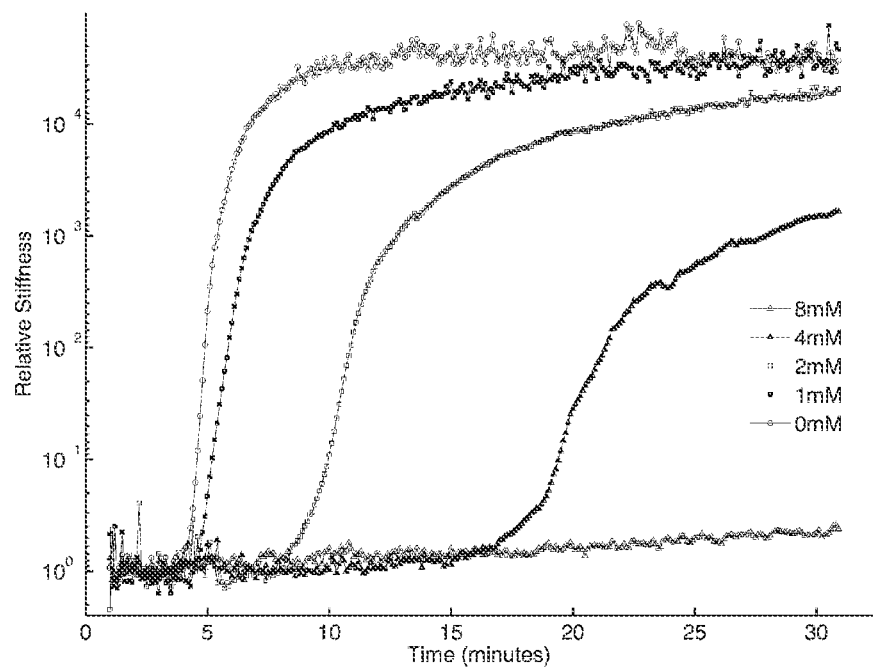
FIG. 10 is a plot of a curve showing sonoheometry measured clot stiffness at a range of GPRP concentration.
Figure 11:
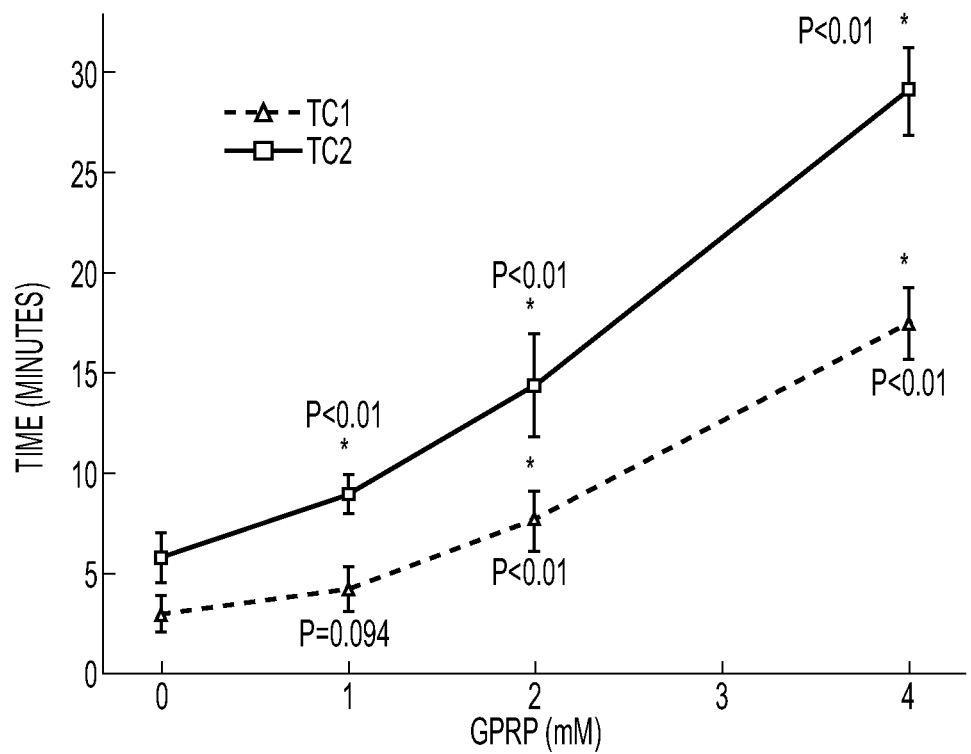
FIG. 11 is a plot of a curve showing initial (TC1) and final (TC2) clotting times increasing with concentration of GPRP.
Figure 12:
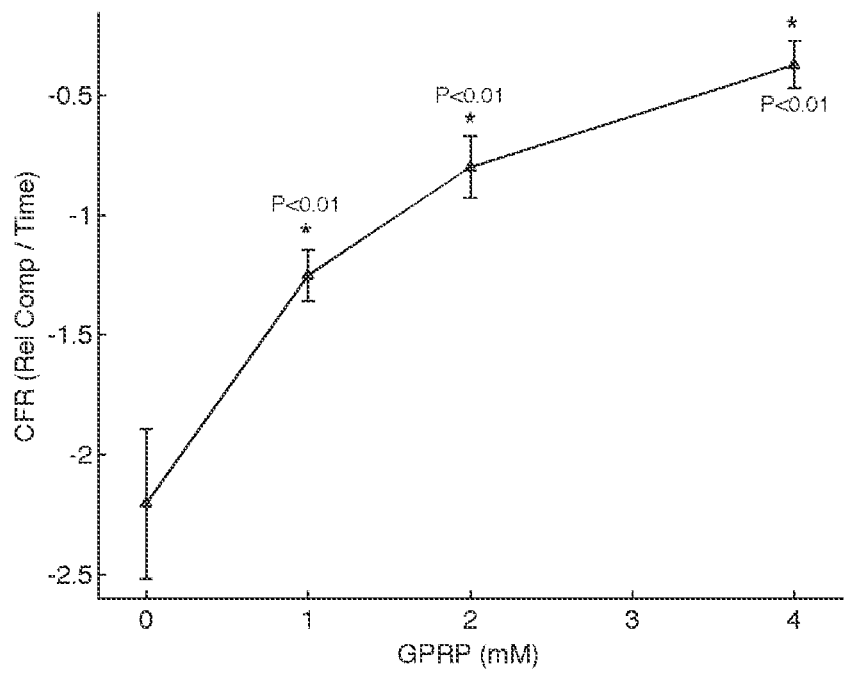
FIG. 12 is a plot of showing clot formation rate with varying GPRP concentration.
Figure 13:
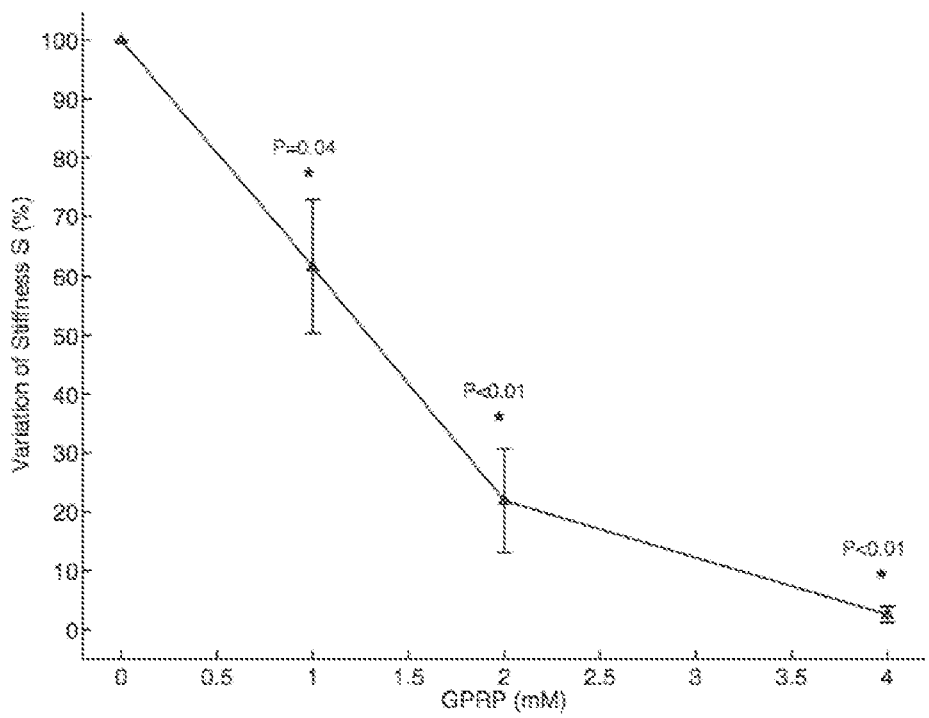
FIG. 13 is a plot showing stiffness.

These experiments were performed to characterize the function of the plasma coagulation factors and the consequent generation of a viscoelastic fibrin structure using sonorheometry. Fibrin is the building block of blood clots. Blood samples from 5 volunteers were obtained and the Gly-Pro-Arg-Pro (GPRP) peptide was added in titrated quantities to achieve final concentrations of 0, 1, 2, 4, and 8 mM. GPRP is a strong inhibitor of fibrin polymerization that blocks the sites located in the © chains at the two D end domains of the fibrinogen molecule, as described in further detail by Laudano et al., *Studies on synthetic peptides that bind to fibrinogen and prevent fibrin polymerization. Structural requirements, number of binding sites, and species differences*. Biochem 1980; 19:1013-1019. Increasing concentrations of GPRP produced distinctive changes in mechanical properties, as shown in the sonorheometry stiffness curves in FIG. 10, which correspond to GPRP concentrations of 0, 1, 2, 4, and 8 mM, respectively. Both initial and final clotting times $TC_1$ and $TC_2$ increase with the concentration of GPRP, as shown in FIG. 11. These results suggest that $TC_1$ and $TC_2$ are representative of the beginning and ending phases of fibrin polymerization caused by the coagulation factors in the plasma. Significant changes were also observed for both the clot formation rate CFR (FIG. 12) and the stiffness S (FIG. 13) with increases in the concentration of GPRP. As expected, the process of fibrin polymerization was a key component in determining the dynamics of clot formation and clot stiffness. Increasing levels of GPRP decreased both the rate of fibrin polymerization and the final stiffness of the formed clot.

Assessment of Platelet Function

Platelets play various important roles during hemostasis. These complex functions include: adhesion to the site of injury, activation and shape change, secretion of internal granules to recruit additional platelets, aggregation with surrounding platelets via fibrinogen links, interaction with fibrin mesh, and clot retraction in order to reduce the volume of the clot, see also Carr, "In Vitro Assessment of Platelet Function", Trans. Med. Review 1997; 11:106-115 and Packham, "Role of platelets in thrombosis and hemostasis", Can. J. Physiol. Pharmacol. 1994; 72:278-284. Of particular importance is the mechanism of aggregation, which ultimately determines the ability to form a platelet plug that can stop bleeding. Aggregation is mediated by fibrinogen that binds to the glycoprotein (GP) IIb/IIIa, forming bridges between adjacent activated platelets. Experiments were performed to investigate the contribution of platelets on sonorheometry measurements. Titrated quantities of monoclonal antibody abciximab were added to blood samples from five individuals to achieve final concentrations of 0, 2, 4, 6, 8, and 12 µg/ml. Abciximab is a potent inhibitor of platelet aggregation that prevents platelets from binding to fibrinogen by blocking the IIb/IIIa receptor on the platelet's surface, see The EPIC Investigators, "Use of monoclonal antibody directed against the platelet glycoprotein IIb/IIIa receptor in high-risk coronary angioplasty", N. Engl. J. Med. 1994; 330:956-961 and Collier et al., "A murine monoclonal antibody that completely blocks the binding of fibrinogen to platelets produces a thrombastenic-like state in normal platelets and binds to glycoproteins IIb and/or Ma", J. Clin. Invest. 1983; 72:325-338.

Figure 14:
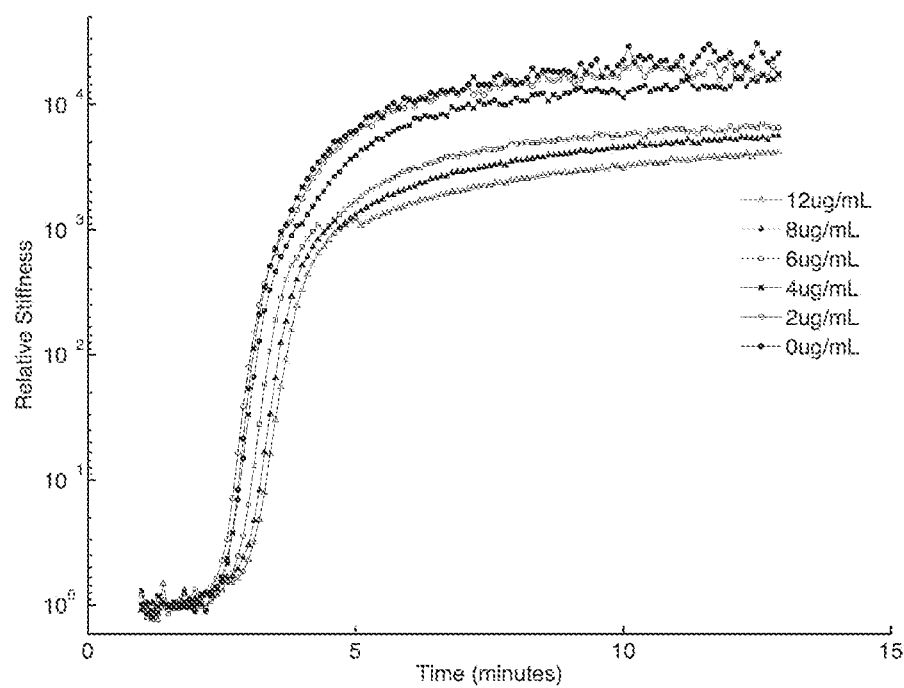
FIG. 14 is a plot showing the effect of concentrations of abciximab.
Figure 15:
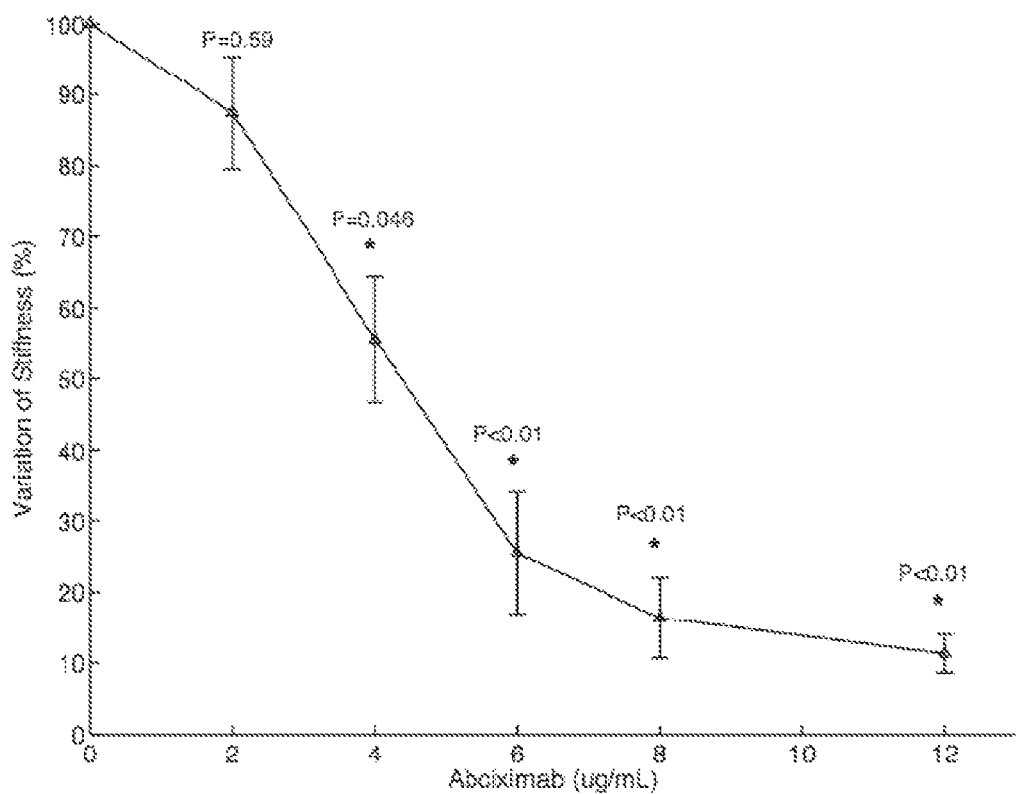
FIG. 15 is a plot showing percentage changes of SMAX as a function of abciximab concentration

The resulting sonorheometry curves demonstrate that increasing inhibition of platelet aggregation reduces the stiffness $S_{MAX}$ yielding a softer clot, as shown by curves in FIG. 14, which correspond to concentrations of abciximab in the samples of 0, 2, 4, 6, 8, and 12 µg/ml, respectively. The other parameters describing the dynamics of clot formation and dissolution did not change significantly, but fell within the intrinsic variability. Final clot stiffness varied by over one order of magnitude across the concentrations used for this experiment. FIG. 15 shows percentage changes in $S_{MAX}$ as a function of abciximab concentration.

The results of the experiments and plots shown in FIGS. 14 and 15 suggest that the final stiffness of the clot resulted from the interaction of aggregated platelets and fibrin network. The stiffness parameter SMAX is thus indicative of the combined mechanical functions of the fibrin network and the platelet aggregation/contractile function. The ability of sonorheometry to characterize platelet aggregation is thus useful, for example, to determine the efficacy of therapies based on Plavix® or non-steroidal anti-inflammatory drugs (NSAIDs) and to discriminate responders from non-responders to these drugs.

Assessment of Fibrinolytic Proteins

Experiments were performed to assess fibrinolysis using sonorheometry. For this set of experiments, titrated amounts of urokinase type plasminogen activator were added to the samples. Urokinase type plasminogen activator is a serine protease that promotes dissolution of the fibrin network that forms the blood clot, see Lijnen et al., "The mechanism of plasminogen activation and fibrin dissolution by single chain urokinase-type plasminogen activator in a plasma milieu in vitro", Blood 1989; 73:1864-1872. Total amounts of urokinase were 0, 100, 150, and 200 Units per ml of blood, respectively. Urokinase shows significant effects on the measurements performed by sonorheometry, as indicated by the relative stiffness curves in FIG. 16 that correspond to total amounts of urokinase of 0, 100, 150 and 200 Units per ml of blood sample, respectively. The blood samples returned to a viscous fluid significantly faster with increasing concentrations of urokinase, as expected. Both clot lysis times $TL_1$ and $TL_2$ decreased as a function of urokinase concentration, as illustrated in FIG. 17.

Figure 16:
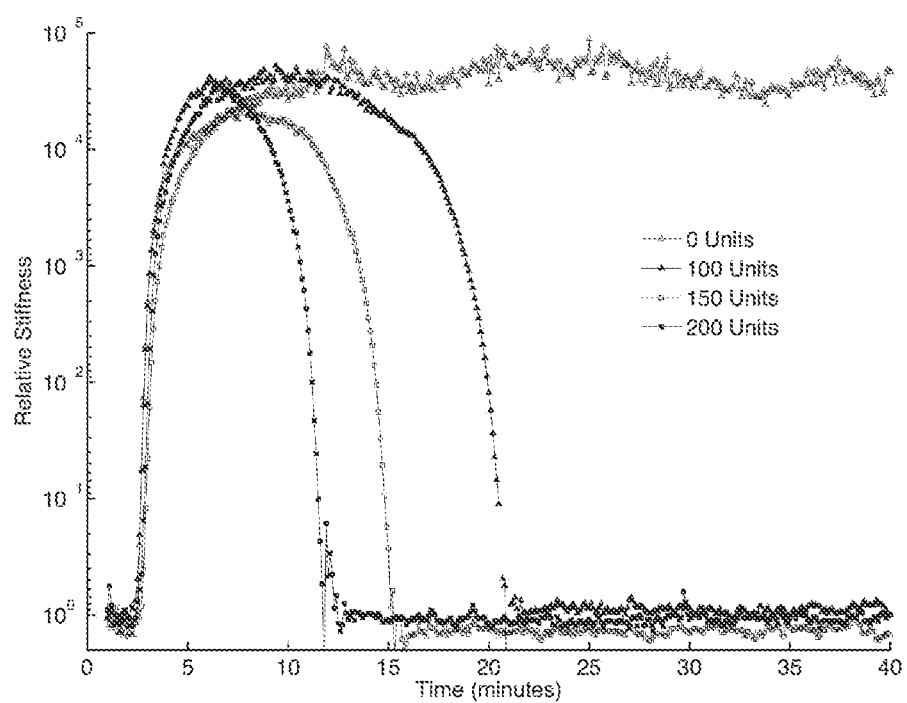
FIG. 16 is a plot showing relative stiffness as a function of urokinase concentration.
Figure 17:
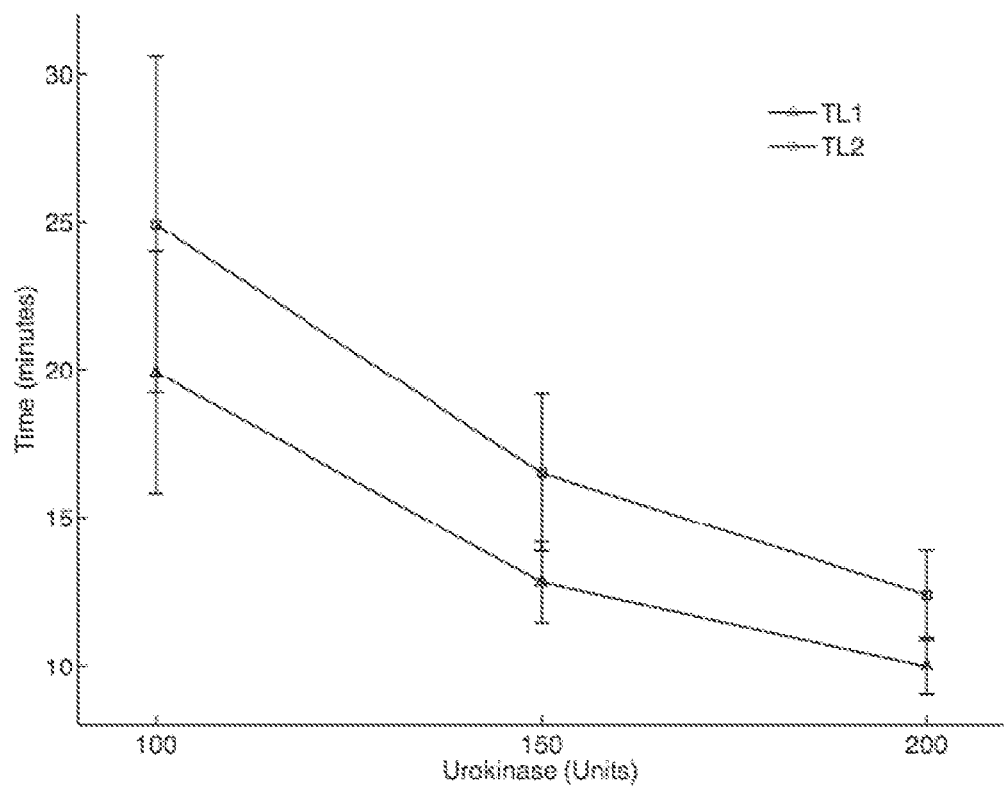
FIG. 17 is a plot showing effect of urokinase on clot lysis times.

FIGS. 16 and 17 show that the increased fibrinolytic activity caused by urokinase rapidly dissolved the blood clot and restored the original mechanical conditions prior to clot formation. The results in FIGS. 16 and 17 suggest that the parameters $TL_1$ and $TL_2$ can be used to characterize dysfunctions of the fibrinolytic system, such as in the case of hyperfibrinolysis.

Reproducibility Error of Repeated Sonorheometry Measurements

The intrinsic variability of sonorheometry was tested using whole blood samples from five volunteers. For each subject, ten samples were obtained into 1.8 ml Vacutainers (with 3.2% sodium citrate) and analyzed sequentially using kaolin activation. The estimated coefficients of variation were below 6% (averages over the five subjects) for all of the parameters described above, except $LT_1$ and $LT_2$ (the coefficient of variation for $LT_1$ and $LT_2$ were not estimated since clot lysis was not observed within the experiment time of fifteen minutes).

II. Determination of HCT and Associated Parameters

Despite the success of the above-described embodiments, the inventors have learned that measurement of whole blood parameters for characterizing clotting can be dependent upon or affected by the hematocrit (HCT) of the measured sample. Other embodiments of the present invention account for the impact of HCT by having integrated therein the capability to additionally quantify HCT and related parameters for use in correcting or adjusting clotting parameters measured by the above-listed embodiments.

An integrated ultrasonic system of the present invention can provide measurements of HCT, hemoglobin concentration (HGB), mean corpuscular volume (MCV), red cell count (RBC), total protein concentration (TPC), mean cellular hemoglobin (MCH), and mean cellular hemoglobin concentration (MCHC) and use those measurements for correcting or adjusting clotting parameters. These parameters are referred to collectively herein as oxygen transport parameters which are any parameters that characterize a fluid's ability to transport oxygen throughout an organism.

Ultrasound measurements of HCT and related parameters may include backscatter—measuring energy reflected from a blood sample, attenuation coefficient—measuring energy attenuation per unit length through a blood sample, speed of sound—measuring the speed of sound through a blood sample, frequency analysis—measuring the response of the blood chamber to ultrasound at more than one frequency.

The HCT and related parameter aspect of the embodiment sends one or more ultrasonic signals to a blood sample; senses and analyze the echoed sound; calculates backscatter coefficients, speed of sound, and/or attenuation coefficient for frequencies of interest; determines one or more of HCT, MCV, HGB, TPC using the correlations that relate speed of sound, attenuation coefficient, frequency and/or backscatter coefficients to said blood properties. From these results, the values of RBC, MCH, and MCHC may be calculated, in some cases depending upon availability of another parameter, using the definitions RBC=HCT/MCV, MCH=HGB/RBC, and MCHC=MCH/MCV.

The equipment preferably includes, or duplicatively uses from the prior embodiments, an electronics subsystem and a hardware subsystem. The electronics generate the signal burst and record and analyze the resulting echoes. The hardware contains the sample and maintains alignment of the various components.

Preferably, the HCT measurement aspect of the apparatus includes, or duplicatively uses from the prior embodiments, a sample collection mechanism, sample chamber, transducer, transducer coupling to the sample, and automated signal processing. Hematocrit is defined as the volume fraction of red blood cells in a sample of blood. The speed of sound in blood is a direct function of the hematocrit (HCT) and a direct function of the amount of hemoglobin in the blood (HGB). This relationship arises because red blood cells and hemoglobin have different material compositions from the surrounding plasma and therefore different speeds of sound. The speed of sound of whole blood is approximately the bulk average of the speeds of sounds of its components. In other words, the higher the concentration of red blood cells, the more the speed of sound of the blood will approximate that of red blood cells instead of plasma. Because red blood cells make up nearly 50% of the blood volume, HCT and HGB are by far the strongest drivers the speed of sound. Variations of other blood components (white blood cells, platelets, extra-cellular proteins) may change the speed of sound slightly and limit the accuracy of the measurements, but their influence is small enough that it has not been identified in experiments to date.

Since the majority of the hemoglobin is in the red blood cells under normal physiological conditions, the HGB and HCT results typically provide equivalent information to the physician. They both indicate the oxygen-carrying capacity of the blood.

$$Cf = g(HCT, T) \quad (14)$$

$$Cf = f(HGB, T) \quad (15)$$

Where Cf is the speed of sound in blood, HGB is concentration of hemoglobin, HCT is hematocrit, T is temperature, and f and g are functions that can be determined empirically.

Because speed of sound is a function of HGB and HCT, one can measure speed of sound and apply it as an indication of the HGB and/or HCT by inverting the calculation.

Similarly, the attenuation coefficient in blood is a direct function of the HGB and HCT of the blood because ultrasound attenuates to different degrees in red blood cells than it does in pure hemoglobin or in plasma. This attenuation is caused in part by the viscous losses in the various substances that make up whole blood. The attenuation is also caused in part by the ultrasound scattering off material boundaries such as the membranes of red blood cells. For this reason, the attenuation is also a function of the MCV of the blood, although the relationship is weak enough that in some cases it may be neglected.

$$\alpha = f(HCT, MCV, T, F) \approx f(HCT, T, F) \quad (16)$$

where $\alpha$ is attenuation coefficient, HCT is hematocrit, MCV is mean cellular volume, T is temperature, F is frequency, and f is a function that can be determined empirically.

For embodiments in which the relationship between attenuation coefficient and MCV can be neglected without sacrificing excessive accuracy, redundant measurements can be made. Attenuation coefficient and speed of sound can both be used to independently calculate hematocrit and hemoglobin concentration. Then, the two calculations can be compared for error detection and/or averaged to improve accuracy. Alternatively, the two measurements can be used together to eliminate another common variable such as the distance the sound travels in blood or temperature.

Backscatter is the acoustic energy reflected from blood. Since this reflection originates almost entirely from scattering off the red blood cells, the backscattered energy is a complex function of the MCV and HCT of the blood sample. However, the function is only monotonic and well behaved for HCT levels below 15%. Preferably, to use backscattered energy to accurately determine MCV and HCT of a sample, the blood sample first can be diluted to bring the HCT into the linear region below 15% then the device preferably compensates for the dilution in its calculations.

$$Bks = f(HCT, MCV, T, F) \quad (17)$$

where Bks is backscattered energy, HCT is hematocrit, MCV is mean cellular volume, T is temperature, F is frequency, and f is a function that can be determined empirically. It should be noted that scattering is a "noisy" parameter and may be difficult to measure while speed of sound is a clean measure. Attenuation occurs between the two.

By measuring the ultrasonic backscatter coefficient and using a correlation to HCT, one can determine the HCT of the diluted sample, and thus the hematocrit of the original sample. The backscatter method can also be used in an un-diluted sample though the relationship is more complicated. One motivation for measuring backscatter on an undiluted sample is to determine the blood parameters non-invasively by sending and receiving ultrasound into the body.

In one embodiment, the method includes subjecting a whole blood sample to one or more ultrasonic pulses, then measuring the ultrasonic characteristics listed above: (a) backscatter from the blood sample, (b) attenuation of the ultrasonic pulse through the blood sample, or (c) the speed of sound through the blood sample. The measurement of (a), (b) or (c) can be used alone or in combination to determine one or more of the related clinical parameters: HCT, HGB, MCV, RBC, MCH, MCHC, TPC.

The preferable way to calculate speed of sound is by measuring the time of flight of short ultrasonic pulses over a known distance.

$$Cf = d/t \quad (18)$$

where Cf is the speed of sound, d is the distance the sound travels through the sample, and t is the measured time it takes for the sound to travel that distance.

The time between transmission and reception is usually considerably longer than the transit time through the sample because it includes delays in the electronics and delays as the ultrasonic wave passes through materials not being studied such as the container walls. Preferably, the transit time through the sample is not measured directly but instead is determined as the difference between two other measurements: the total transit time (which includes both time in the blood and undesired delays) minus the transit time through only undesired delays.

$$t_{blood} = t_{total} - t_{delays} \quad (19)$$

where $t_{blood}$ is the transit time the ultrasound takes to travel through the sample, $t_{total}$ is the measured time from send to receive including undesired delays, and $t_{delays}$ is the measured time of all delays except for the transit through the sample.

Figure 6:
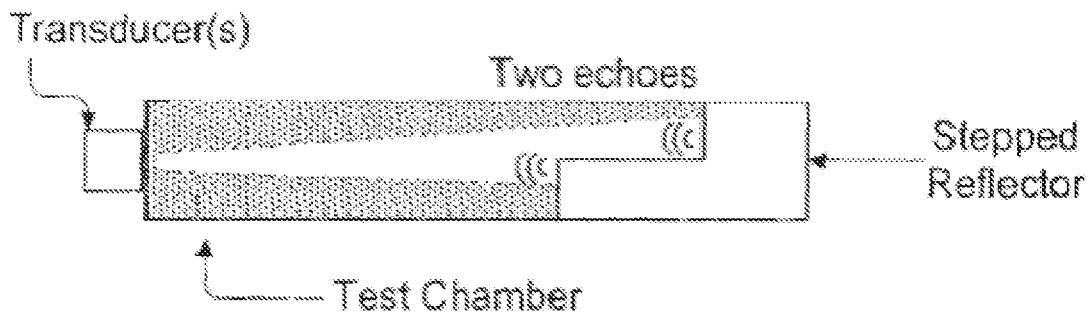
FIG. 6 is a schematic of a two-reflector system for determining HCT and similar blood parameters.

One preferable way to measure this time difference is to measure the round trip times of flight from two or more reflectors separated by a known distance along the axis of flight (see FIG. 6). The ultrasound is broadcast in one beam. A portion of the ultrasound echoes from the closer reflector while the rest of the beam continues traveling to echo off the second reflector. The difference between these round trip times, divided by two times the distance between reflectors, is the speed of sound in the sample.

Figure 8:
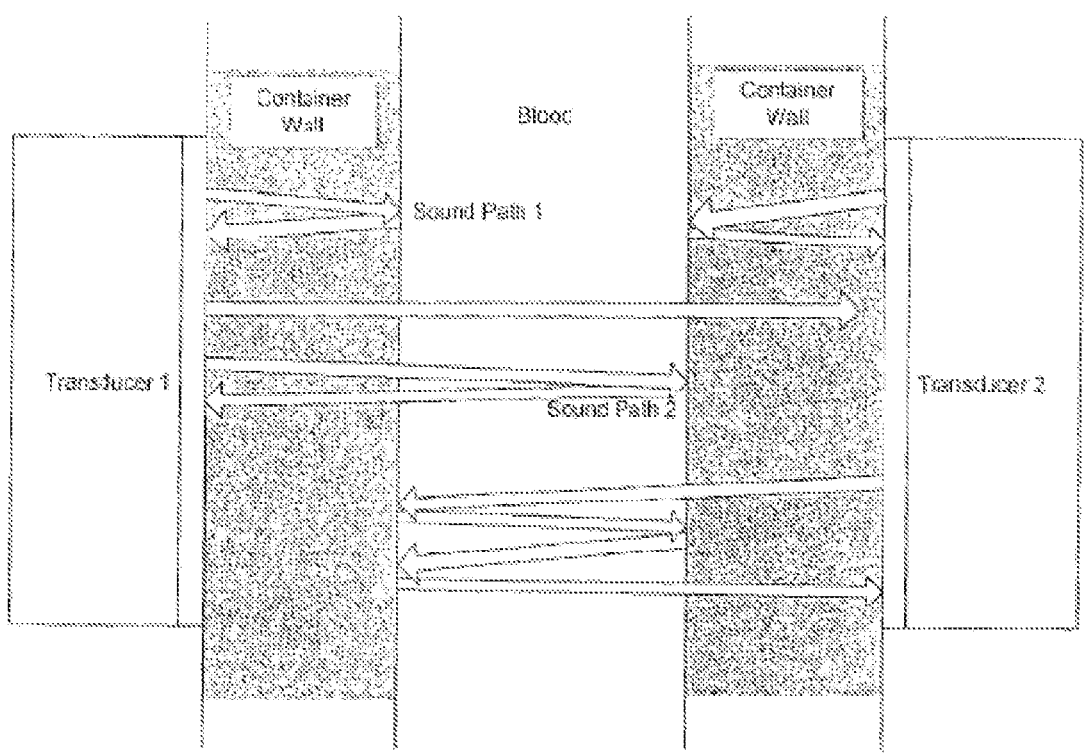
FIG. 8 is a schematic of a two-transducer system for determining HCT and similar parameters.

Another preferred embodiment uses a chamber of a precisely known size through which transducers send pulses in pitch-catch mode (see FIG. 8). Using pulse-echo measurements from the edges of the chamber allows subtraction of all time delays except the time the sound spent traveling through blood.

In another preferable embodiment, the blood is in a flexible chamber, and time-of-flight measurements are made both before and after deforming the chamber by a known or measurable distance. In another embodiment, the blood is in a flexible container that fills the space between two precisely located walls. The container material is well controlled such that its time delay is well known and can be subtracted. Preferably, the speed of sound through this flexible wall is roughly matched to the speed of sound through blood, so that the error caused by inaccuracies in estimating the thickness of the wall will negligibly affect the transit time.

Temperature affects speed of sound, attenuation coefficient, and backscatter so the results are preferably adjusted to account for temperature, such as by using the embodiments described above. Furthermore, depending on the materials selected, it may need to account for temperature affects on the sizes and shapes of its component parts.

The technique used to measure the attenuation coefficient in blood is similar to the technique used to measure speed of sound. The RMS amplitude of the reflections is measured. If a known reflector, the absolute amplitude of the echo will be measured. The ratio of the amplitudes from two paths through blood of different lengths is expressed in decibels and divided by the difference of the path lengths.

$$A = 20 \, \text{Log}(V2/V1)/(D2-D1) \quad (20)$$

where A is the attenuation coefficient in dB/in, V2 and V1 are the amplitudes of the two received signals, and D2 and D1 are distances the two signals traveled through the sample.

The speed of sound data and the attenuation coefficient data are usually collected at the same time for each sample. Furthermore, the calculations can be compensated for the temperature of the blood and frequency of the signals.

The backscatter measurement is performed by analyzing the ultrasonic echo from a diluted blood sample and measuring the RMS voltage of a specified time window within the returned signal. The transducer preferably generates a burst containing 2-10 cycles of the center frequency of the interrogating transducer. Energy is reflected back from blood-chamber interface, followed immediately by the energy scattered back by the components of the blood sample. By time gating the RMS measurement to measure the energy scattered by only the sample, and averaging over 50 sampled signals or more, the average backscattered power is measured.

The clinical parameters (HCT, HGB, MCV, RBC, MCHC, MCH or TPC) may also be determined by exciting the chamber with continuous waves. The frequency of this continuous wave is varied slowly to analyze the response of the blood at each frequency. At the resonant frequency, a standing wave is set up which indicates that the wavelength is directly related to the chamber's dimensions. Determining the resonant frequencies allows one to calculate the wavelength and correlate that to hematocrit. Furthermore, the bandwidth (i.e., fill width at half-maximum) of the resonant frequency peaks is effectively another indication of attenuation. The wider the frequency peak, the higher the attenuation coefficient. Other related ultrasonic measurements that provide similar information include the phase shift or amplitude of the signal.

Acoustic impedance is also an indicator of hematocrit and/or hemoglobin because the acoustic impedance of hemoglobin and other blood constituents is higher than the acoustic impedance of pure plasma. Therefore, higher concentrations of hemoglobin and red blood cells will increase the acoustic impedance of the overall substance from that of pure plasma. Acoustic impedance can be calculated by measuring how much ultrasound is reflected from an interface. If the acoustic impedance of the blood matches the acoustic impedance of the container wall, then no ultrasonic energy will be reflected from the interface. The more the mismatch of acoustic impedances, the more energy will be reflected from the interface. The apparatus preferably lyses the red blood cells before implementing this method to ensure that the hemoglobin and other blood constituents are evenly distributed throughout the blood and along the material interface being used to measure acoustic impedance.

Another ultrasonic measurement that indicates the physiological parameters is refraction angle. The refraction angle of the ultrasonic wave at a material interface is an indicator of speed of sound as shown by Snell's Law. Therefore, refraction angle will be directly affected by the physiological hematocrit and/or hemoglobin. One preferred way to implement the refraction measurement is to send ultrasound through a triangular blood container that acts as a "prism." The ultrasonic wave enters the blood perpendicular to the container surface. But, because of the triangular shape of the container, the ultrasound strikes the far wall of the chamber at a known angle of incidence. According to Snell's law, the wave will then travel through the container wall at a angle that depends on the speed of sound in the blood. Measuring that angle (preferably using a steered array transducer) allows the apparatus to back-calculate the speed of sound in the blood use an empirical correlation to calculate the hematocrit and/or hemoglobin.

$$\text{Snell's Law: } \sin(\Theta 1)/C1 = \sin(\Theta 2)/C2 \quad (21)$$

where $\Theta 1$ is the angle of incidence, C1 is the speed of sound in material 1, $\Theta 2$ is the angle of refraction, and C2 is the speed of sound in material 2

Figure 5:
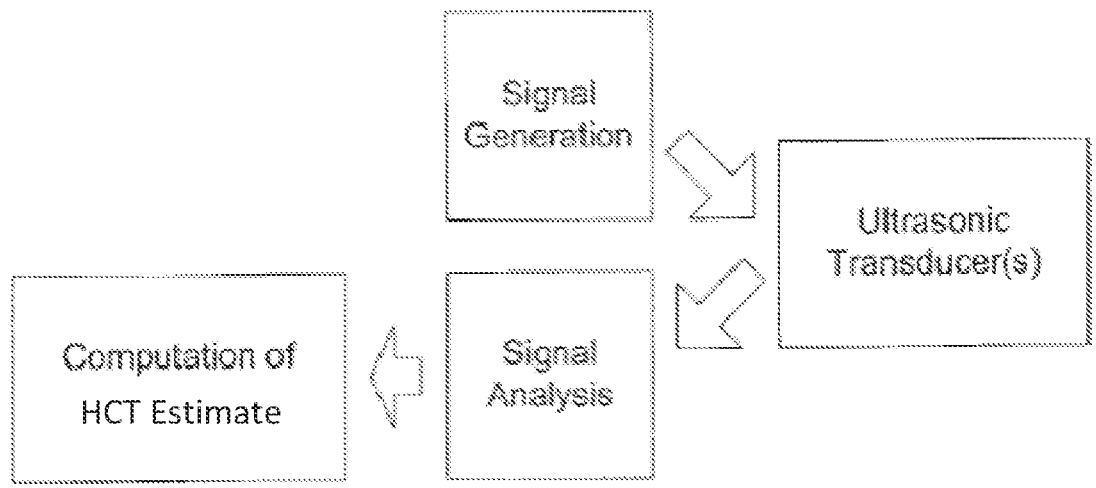
FIG. 5 is a schematic of electronics for a system for determining HCT and similar blood parameters.

The electronics preferably include means for signal generation, signal capture, and analysis. Preferably, the electronics are responsible for four functions (shown in FIG. 5): generating a precisely controlled signal, sending and receiving the ultrasonic waves, analyzing the received waves, and computing the clinically-relevant results. These functions are divided into the input stage and the receiving stage. Each stage may exist as a separate device, or preferably, some or all of the stages may be integrated together as a single component.

The sending stage preferably includes a programmable signal generator, signal conditioning components (to amplify, filter, and/or reduce noise), and a power amplifier. The signal generator functions to generate one or more acoustic signals. The signals may be a gated sinusoid, square pulse, spike with exponential delay or other function. The signal normally would have a center frequency matched to the center frequency of the transducer in use to maximize the amount of energy delivered to the sample. For frequency sweeps, the frequency range is preferably chosen to lie within the usable bandwidth of the transducer.

The pulse generator will preferably generate an electronic pulse to operate the transducers in pitch-catch or pulse-echo mode. The frequency of the signal may be from 1 to 50 Mhz, preferably from 5 to 20 Mhz, depending on the type of measurement being made. Higher frequencies could be chosen if the sound is only traveling a short distance through blood in order to increase time resolution or to achieve wavelengths proximate in length to a red blood cell diameter. Lower frequencies could be chosen for long paths to minimize attenuation. The burst length may, for example, be 0-5 cycles, most particularly preferably 1-2 cycles for speed of sound and attenuation coefficient measurements. The amplitude of the signal generator is preferably maintained at a setting sufficient to provide high-signal-to-noise ratio.

The signal from the input stage is passed to the transducer. The transducer(s) are preferably high efficiency, single element transducers. A variety of commercially available transducers are suitable for use in the apparatus. Each transducer may be selected to match the chamber geometry based on the center frequency, bandwidth, focusing, sensitivity, and beam pattern. For backscatter measurements, the range of frequencies is selected to include values both above and below the 15 MHz threshold for Rayleigh scattering. Preferred interrogating frequencies include 6.5, 10, 20, 30, and 40 MHz. In general, higher frequencies are preferable if the sound is only traveling a short distance through blood in order to increase time resolution and narrow the acoustic beam. Lower frequencies are preferable for long paths to minimize attenuation.

For all configurations and measurements, the, transducer element diameter is preferably selected to ensure that the beam angles are appropriate for the shape of the chamber. The beam widths should be narrow enough to minimize the chance of undesired sound paths interfering with the measurement. Furthermore, the element diameter affects the distance the transducer can be from the sample (far field distance). Focused transducers may help reduce beam width and far-field distance. Some preferred transducer diameters include 3 mm, 6 mm, and 12 mm. The transducers may be used in pulse echo mode and/or in pitch catch mode depending on how they are arranged relative to the chamber. Measuring the time difference between paths or between these two operating modes can eliminate unknowns such as the delays in the electronics or sample holder. An annular array of transducers could be used to enable a deeper depth of field.

Figure 7:
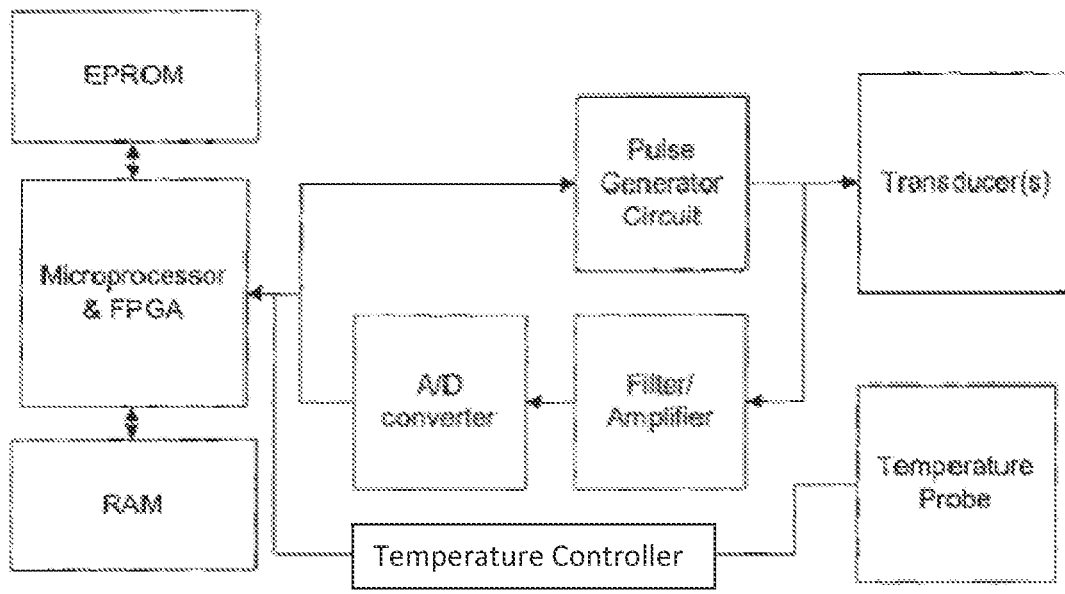
FIG. 7 is a schematic of components of a system for determining HCT and similar blood parameters.

The signal returned from the sample causes the transducer to generate an electrical signal that is passed along to the receiving stage. The receiving stage preferably includes signal conditioning, an amplifier, a digitizer, and a means for collecting and analyzing data, such as a microprocessor or microcontroller and RAM, magnetic storage or CD (see FIG. 7). In this configuration, signal measurements and calculations including transit times and amplitude are calculated based on the digitized signal by the microprocessor.

Another preferable receiving stage configuration includes signal conditioning, an amplifier, an analog peak detect circuit and a timing circuit. The peak detect circuit is used to measure the signal peak amplitude and the timing circuit is used to determine the time from signal transmission to receipt.

The amplifier is used to bring the signal amplitude up to a level that can be readily captured by a digitizer and/or analyzed by analog electronics. Therefore, the amplifier should be chosen to have the needed gain. The amplifier should also be chosen to have the appropriate bandwidth for the planned measurements. The amplifier(s) may also include one or more filters built-in. The filters are used to eliminate noise that lies outside the frequency band being measured. Suitable filters include active and passive filters, RC filters.

The HCT detection aspect also preferably includes appropriate device control, signal processing and detection logic. Device control may be through an on-board processor, programmable logic controller or through discrete logic blocks. The signal processing algorithms preferably include one or more of the following: analog and digital noise filtering, averaging, gating and automatic gain control. Detection logic may include zero-crossing detection, which automatically measures the exact time a signal crosses zero in order to calculate the transit time of a signal, and amplitude or power measurement. A time delay estimation method, similar to that used for motion estimation under radiation force, could also be used.

Hardware preferably includes the sample chamber and transducer. The sample chamber or holder is designed to contain the blood sample, allow for stirring of the sample (in the case of backscatter measurements), and maintain alignment and distance between the transducer and the sample. Stirring could be performed by using high intensity pulses to generate acoustic radiation force induced streaming. In some embodiments of the apparatus, the chamber is actually a segment of a tube through which the blood flows continuously (ex-vivo). In other embodiments the chamber is made of flexible materials such as rubber so the blood sample's size or shape can be controlled or adjusted. Alternatively, the blood chamber may comprise the patient's body itself in the case of an in-vivo or non-invasive measurement.

The collection means includes allowances for making live blood draws. The collection method may be an off the shelf syringe, off the shelf lance, or custom device which acts as a collection device and a sample chamber combined. Furthermore, the chamber may be a tube through which the blood flows.

The sample chamber is preferably disposable and compact. Preferred sample chamber materials include glass, polystyrene, poly amide, polyvinylchloride, silicone, polypropylene, latex or polyethylene. The chamber and/or added reflectors (if used) are preferably manufactured to precisely known dimensions so that the sound path length is preferably known to +/−0.2%, more preferably to +/−1-0.05%, which ranges include +/−0.1 5, 0.125, 0.1, 0.09, 0.075, and 0.065%. A precisely-known path length is preferred to more accurately calculate speed of sound from measuring the time of flight. If the chamber cannot be accurately manufactured, then the path length is preferably measured either by the apparatus itself or by an independent device. The results from said independent device would preferably be fed into the apparatus automatically by a means such as barcodes.

The sample chamber and/or apparatus parts in acoustic contact with the blood and/or sample chamber preferably has a speed of sound matched to the speed of sound in blood between 1000 m/s and 2500 m/s, which range includes 1200, 1400, 1600, 1800, 2000, 2200, and 2400 m/s. Preferable materials include plastic, rubber, aluminum, and combinations thereof.

The sample chamber preferably holds 0.05 to 10 mL of blood, which range includes 0.075, 0.1, 0.3, 0.5, 0.7, 0.9, 1, 2, 3, 4, 5, 6, 7, 8, and 9 mL of blood.

The temperature of the sample may be measured directly or indirectly. Indirect means may include waiting for the sample to equilibrate with its environment and measuring the ambient or container temperature in lieu of the blood temperature. If the temperature of the blood is changing rapidly (because it has been freshly drawn for example) repeated ultrasonic measurements allow the apparatus to infer a trend and predict what the final readings would be once the sample has reached thermal equilibrium with its surroundings. Since speed of sound in any apparatus or container changes with respect to temperature, the temperature of the container walls can be inferred by measuring the speed of sound through the walls. The temperature may also be controlled (such as by a temperature controller shown in FIG. 7) so that no temperature variations affect the measurement.

The sample chamber and collection means can also be combined into a single component, wherein the blood sample is collected in the collection means, which then acts as the sample chamber upon which the ultrasound method is used. Further, the collection means and sample chamber may comprise a tubular arrangement such that the blood is collected from the patient using a venipuncture needle or other needle device, whereupon the blood flows through a length of tubing. The length of tubing can act as the sample chamber, particularly for the attenuation coefficient and speed of sound measurement methods performed on a sample flowing through the length of tubing. Backscatter based methods are less desirable using a flowing sample due to movement of the red blood cells through the tube. In any event, a calibration can be obtained using samples of independently measured hematocrit, permitting the measurement of the HCT, MCV and/or RBC of the sample, even when flowing through the sample chamber.

One preferred sample chamber embodiment includes a single or dual element transducer that projects beam(s) through the blood sample, returning reflections from a stepped reflector at the other end of the sample chamber (see FIG. 6). The difference in round trip time from these steps can be used to calculate the speed of sound in the test sample.

The stepped reflector design is preferred in that it has no moving parts, and it is not susceptible to variable time delays outside of the sample chamber, such as transducer couplant delay.

Another preferred sample chamber includes a small chamber with rigid parallel walls and a depth such that only a few drops of blood can fill the chamber. Sound is transmitted through the chamber along a path perpendicular to the walls as in FIG. 8.

Another preferred sample chamber consists of a rubber bladder. This is configured such that when it is placed in the electronics unit and filled with blood, it expands to fill the space between a single fixed transducer and a reflector or between two fixed transducers in the electronics unit.

The reflector could be inside the chamber or outside. Most preferably, the chamber shape itself would act as the reflector for ease of manufacturing. The material of the reflector is not particularly limited. The path length difference is likewise not particularly limited, and could preferably range from 1 mm to 10 cm, which range includes 2, 3, 4, 5, 6, 7, 8 and 9 mm, and 1, 2, 3, 4, 5, 6, 7, 8, and 9 cm. Longer paths are preferred for making a more accurate measurement, but shorter paths require less blood. Moving reflectors are possible. In all configurations, vertical ultrasound paths are preferred so that if the red blood cells settle, their average concentration in the beam remains constant.

In the case of a horizontal beam, the cells could settle preferentially into or out of the beam causing an erroneous reading. Or, different portions of the beam could pass through different concentrations of cells causing a distorted answer. In the same way, a vertical sound path ensures that even if thermal stratification occurs, the ultrasound will travel through all the temperature layers of the blood instead of preferentially measuring through a warmer or colder region. The transducers may use liquid or grease as an acoustical couplant to a solid blood container, may be coupled directly to the sample container (dry coupled), or may transmit sound directly into liquid or gas instead of a solid. The transducers may be held in a fixture to ensure reliable acoustical coupling to the sample. In one preferred embodiment, the transducers are disposable and built into the sample chamber. When disposable transducers are integrated into a disposable chamber, the chamber is preferably connected to the test device electrically instead of acoustically.

The transducers are preferably narrow beam width and more preferably focused to avoid coherent noise caused by stray reflections depending on the geometry of the sample chamber. Preferably, transducers having center frequencies of approximately 1 MHz to 50 MHz, more preferably 5 to 20 MHz may be used. 10 MHz transducers are most preferred, however. The higher frequency transducers accommodate a shorter path length and more precise timing. A pair of transducers are most preferably used, one on each side of the collected sample as in FIG. 8.

Three types of test chamber are preferable for this device and they all use a drop or several drops of blood. The fact that they use a few drops of blood limits the size of the chamber accordingly. The first will be a small capillary tube, preferably capped at one end. This type of tube is similar or identical to that currently used in medical settings as part of a micro-hematocrit test. The second preferred embodiment is a sample card, which collects a drop of blood in a small rectangular hole to through which ultrasonic measurements can be made. The third preferred embodiment is a sample card, which collects a drop of blood in a flexible thin walled chamber that fills the space between two precisely-located walls within the meter. Also, a cartridge could be used with pre-defined wells configured for sample filling using suction, such as the preferred cartridge disclosed in U.S. patent application Ser. No. 13/397,398 filed on Feb. 15, 2012 and entitled DEVICES, SYSTEMS AND METHODS FOR EVALUATION OF HEMOSTASIS which is incorporated by reference herein in its entirety. This application also discloses preferred hardware and processes for determining hemostasis parameters using multiple samples with different reagents.

FIGS. 19A-19G illustrate an example cartridge 100 for use in evaluation of hemostasis in a subject. The cartridge 100 includes a front surface 101 and a rear surface 126. FIG. 1A shows a front view of the cartridge 100 and the corresponding front surface 101. The cartridge includes an inlet 102, also referred to herein as an inlet port or entry port, such as a nipple, thought which a biological sample from the subject can be introduced into the cartridge. Optionally, a blood sample from the subject is introduced into the cartridge at the inlet 102. Another biological sample that may be introduced for analysis is plasma. The inlet 102 is in fluid communication with a channel 202, which is shown in FIG. 2, and which directs the biological sample to other portions of the cartridge as described herein.

The cartridge further includes a port 106 for applying a vacuum to the cartridge. When a vacuum is applied at the port 106, the biological fluid introduced at the inlet 102 into the channel 202 the fluid is propelled along the channel 202 towards the port 106.

Figure 19:
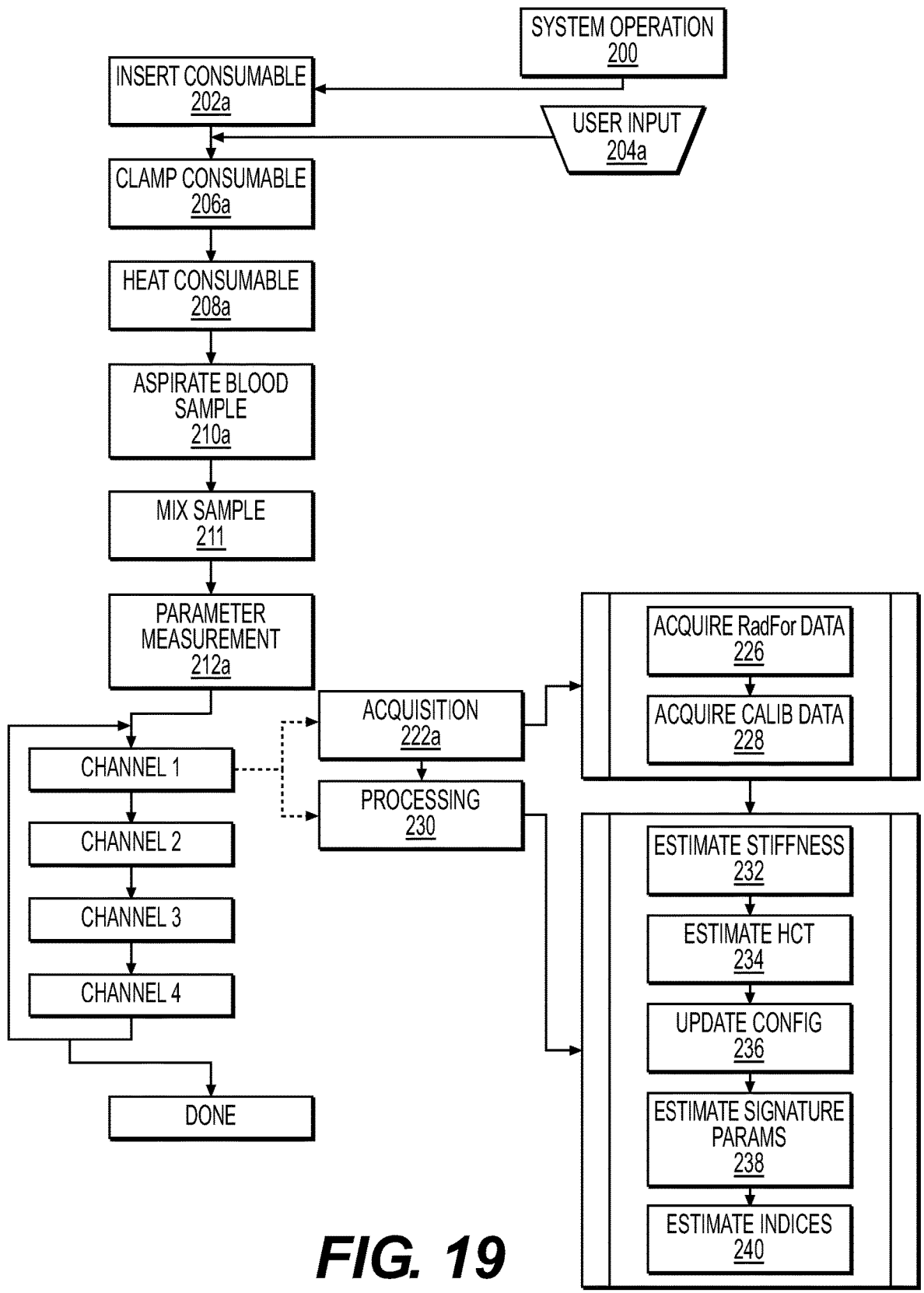
FIG. 19 is a flowchart of an integrated system for determining hemostasis and HCT parameters.
Figure 19A:
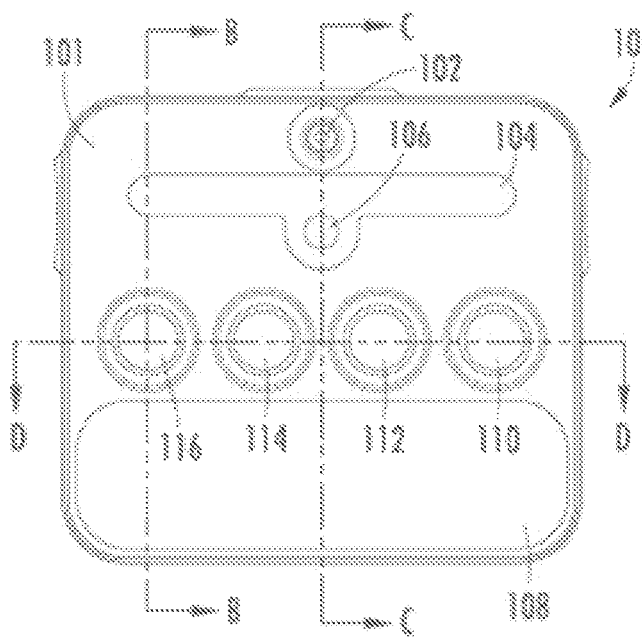
Figure 19D:
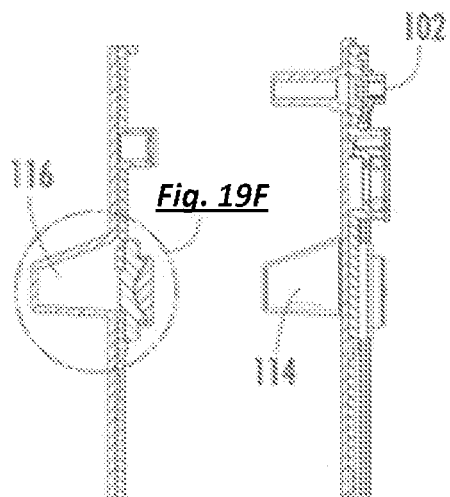
Figure 19D:
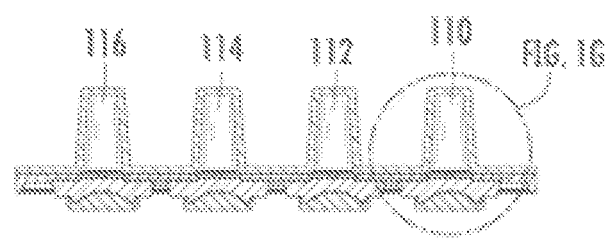
Figure 19E:
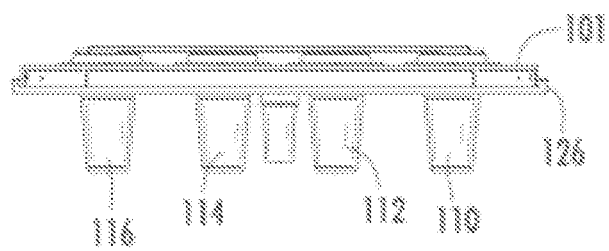
Figure 19F:
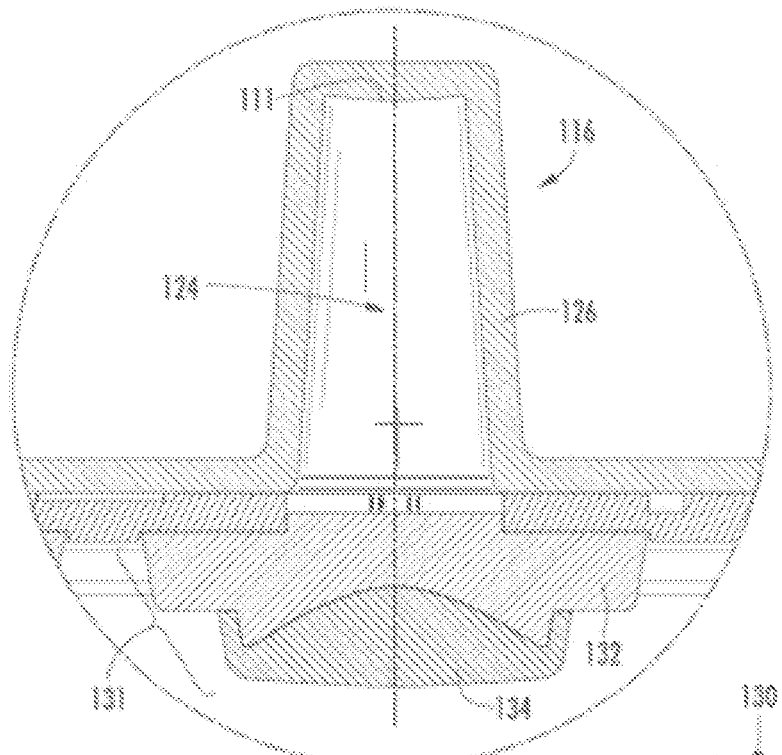
Figure 19G:
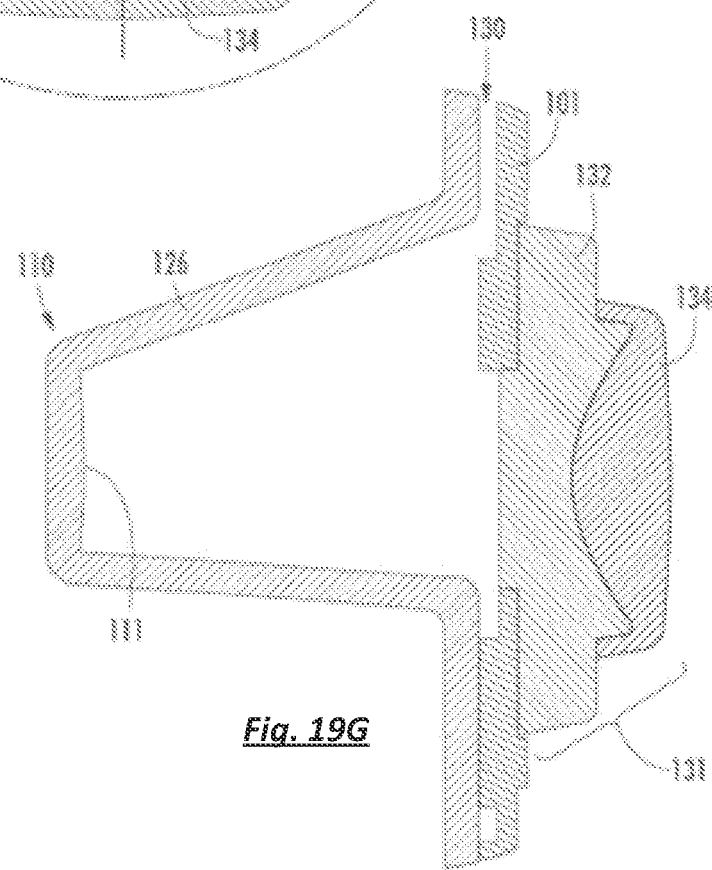
Figure 19H:
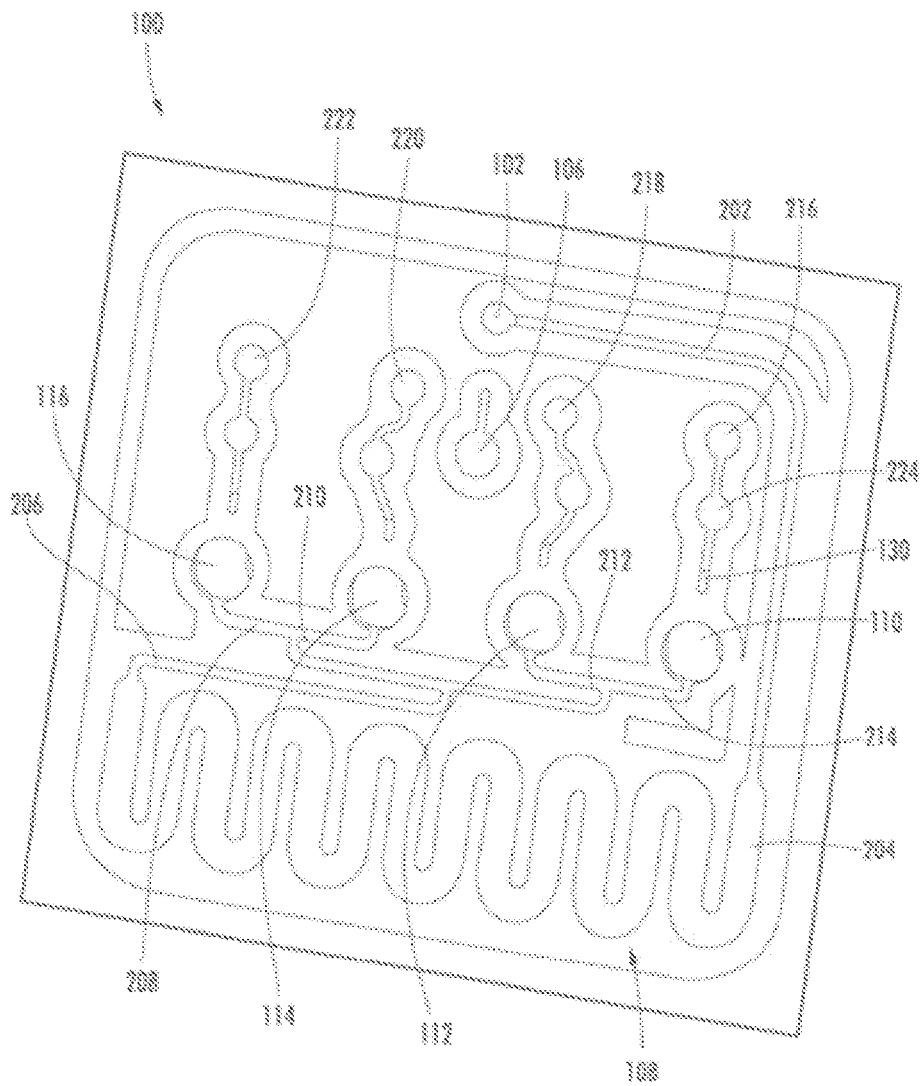
FIG. 19H is a schematic illustration of biological fluid pathways of the example cartridge of FIGS. 19A-19G.

As shown in FIG. 19H, in moving between the inlet 102 and the port 106, the biological fluid, or a portion thereof, moves along the channel 202, into the channel 204, the channel 206, and along the channels 208, 210, 212 and 214. Each of channels 208, 210, 212 and 214 are in fluid communication with a test chamber, also referred to herein, for example, as a, chamber, well or test well or the like. For example, as illustrated in FIG. 2, channel 208 is in fluid communication with a test chamber 116, channel 210 is in fluid communication with a test chamber 114, channel 212 is in fluid communication with a test chamber 112, and channel 214 is in fluid communication with a test chamber 110.

Referring again to FIG. 19, each test chamber comprises an open space 124 defined by a portion of the rear surface 126. FIG. 19B shows a cross-sectional illustration through test chamber 116 taken across the line B-B of FIG. 19A. FIG. 19C shows a cross-sectional illustration taken across the line C-C of FIG. 19A. FIG. 19F shows an expanded view of the circled portion of FIG. 19B. Moreover, FIG. 19D shows a cross-sectional illustration across the line D-D of FIG. 19A, which illustrates the open space of each of the four test chambers.

Each test chamber is configured to accept a quantity of the biological fluid into the open space. In reference to test chamber 116, illustrated in detail in FIG. 19F, a portion of the biological fluid introduced at the inlet 102 moves through the channels 202, 204 and 214 and into the open space 124 of the test chamber 116.

The biological fluid can also exit each respective test chamber and continue along an exit channel 130 towards the port 106. Thus, fluid introduced at the inlet 102 flows under vacuum through the device channels and into the test chambers. From each test chamber (110, 112, 114, 116), the biological fluid continues to flow along exit channels towards the vacuum.

Proximate the port 106 each exit channel may direct the flowing biological fluid into a hydrophobic filter at location 222, 220, 218 and 216 respectively. The filters or filter prevents movement of the biological fluid out of the cartridge 100 at the port 106. Because the volume of the channels and the test chamber are fixed, the vacuum can pull the biological fluid into the cartridge until the channels and each test chamber is filled with the biological fluid.

Figure 19I:
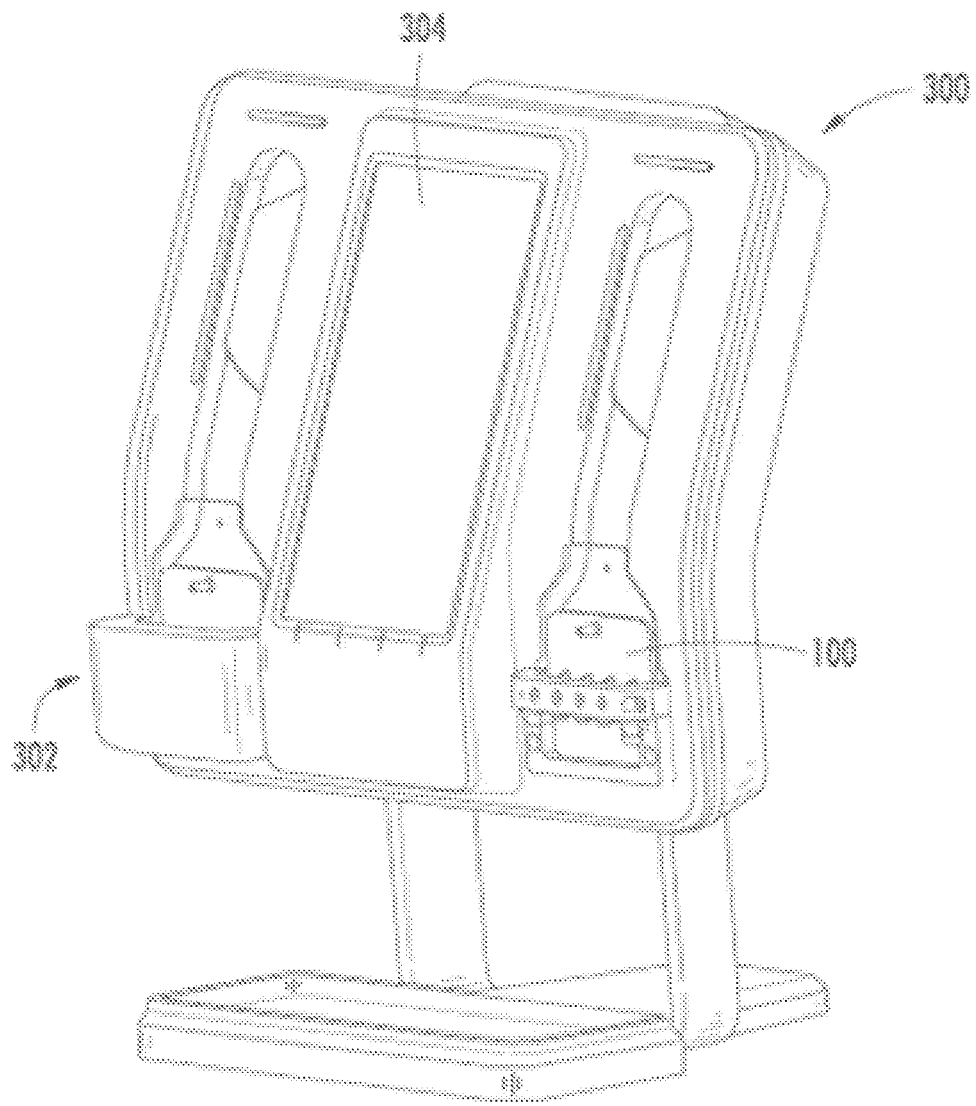
FIG. 19I is a schematic illustration of an example processing system for use with the example cartridge of FIGS. 19A-19G.

Pressure can be controlled within the cartridge 100 to, for example, manage flow rate within the consumable 100 and to mitigate reliability issues related to possible user misuse. To measure the properties of a target biological sample, such as a blood sample, a user of the hemostasis system optionally attaches a blood-filled syringe to the cartridge 100 unit. There exists the possibility that the user of the hemostasis system 300 (see FIG. 19I) could attempt to inject the contents of the applied syringe into the cartridge 100 manually, instead of allowing the device to automatically aspirate the sample. This action may lead to measurement or system error. A pressure management device in the consumable flow path is used to prevent this user action.

Inadequate mixing of the biological sample with the reagents described herein may result in variation of hemostasis measurements. Rapidly aspirating the blood sample is optionally used to provide increased mixing of the reagents with the biological sample, such as a blood sample. This is optionally achieved by creating a pressure differential between the cartridge and the aspirating mechanism of the hemostasis system.

Figure 19J:
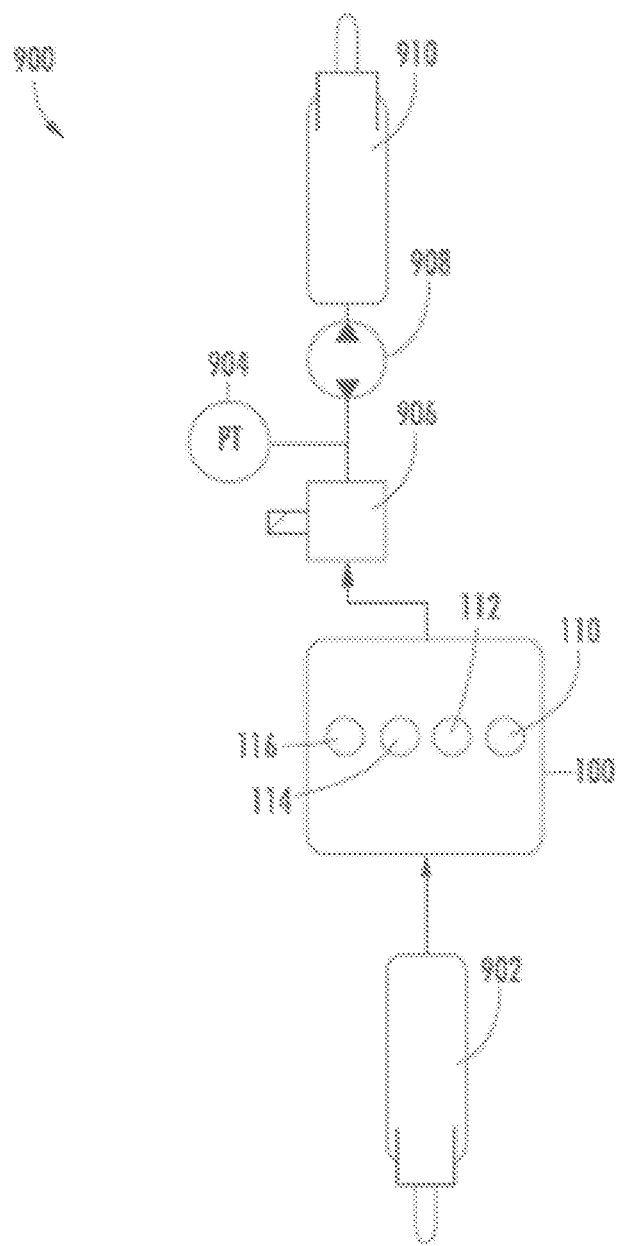
FIGS. 19J-19L are schematic illustrations of portions of a system for evaluating hemostasis including pressure control mechanisms.
Figure 19K:
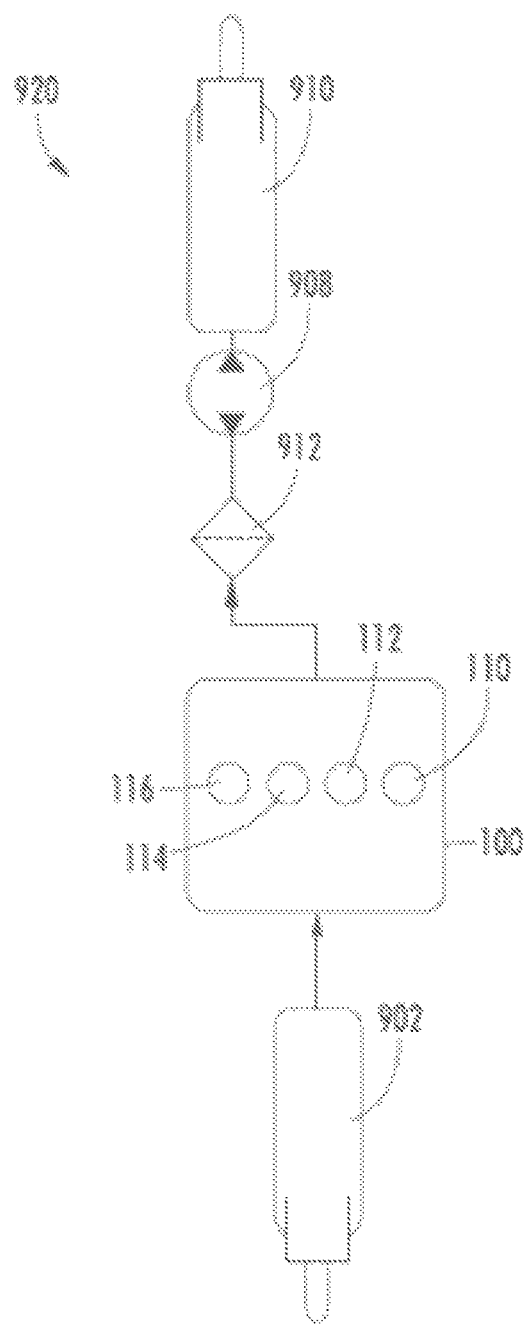
Figure 19L:
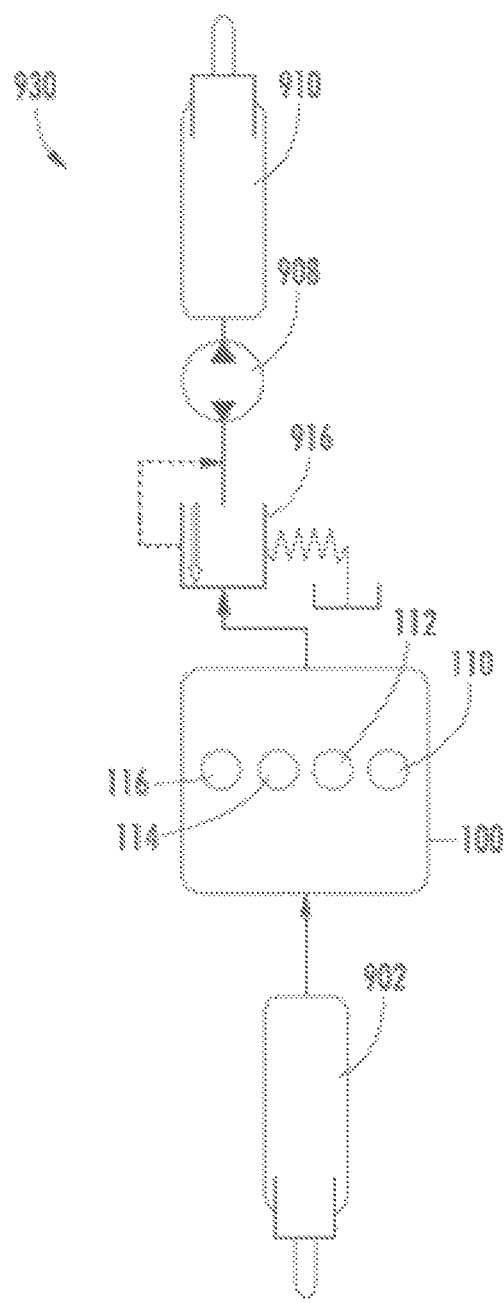

In this regard, FIGS. 19J-19L illustrate three example configurations that can be used to control the pressure differential between the cartridge and the aspirating mechanism and can therefore be used to achieve desired levels of mixing and reduce user errors.

FIG. 19J schematically illustrates an example system 900 for controlling pressure in a cartridge 100. The cartridge includes four test chambers (110, 112, 114 and 116). Each test chamber optionally includes a reagent and operation of the system causes a biological sample to enter one or more test chamber. The example system 900 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A pressure transducer 904 is in communication with the pump that measures the gauge pressure drawn by the pump 908. A solenoid actuated valve 906 operates to block flow downstream of the pump allowing gauge pressure to build. The solenoid may be selectively actuated to rapidly expose the pressure gradient to the cartridge. The sample is allowed to progress through the cartridge and is optionally collected in a sample container 910.

FIG. 19K schematically illustrates another example system 920 for controlling pressure in a cartridge 100. The cartridge includes four test chambers (110, 112, 114 and 116). Each test chamber optionally includes a reagent and operation of the system causes a biological sample to enter one or more test chamber. The example system 920 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A pressure activated membrane 912 is positioned either upstream or downstream of the cartridge 100 from the pump 908. The membrane 912 is configured to rupture at a predetermined cartridge gauge pressure thereby controlling the pressure at which the sample is drawn through the cartridge. The sample is allowed to progress through the cartridge and is optionally collected in a sample container 910.

FIG. 19L schematically illustrates another example system 930 for controlling pressure in a cartridge 100. The cartridge includes four test chambers (110, 112, 114 and 116). Each test chamber optionally includes a reagent and operation of the system causes a biological sample to enter one or more test chamber. The example system 930 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A closed loop actuated valve 916 contains an internal pressure control mechanism and is used to block flow downstream from the pump allowing gauge pressure to build until a valve pressure setpoint. Once gauge pressure setpoint is reached the valve 916 deploys thereby exposing the cartridge to a desired pressure gradient. The sample is allowed to progress through the cartridge and is optionally collected in a sample container 910.

Figure 19M:
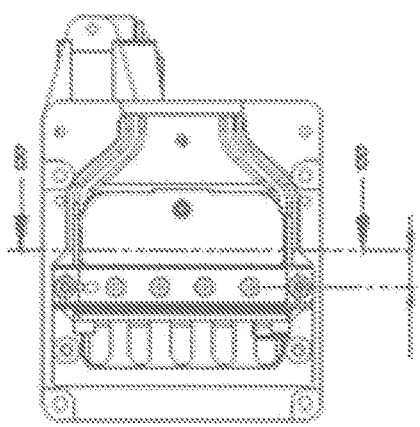
FIGS. 19M-19P are schematic illustrations of an example cartridge for evaluating hemostasis.
Figure 19N:
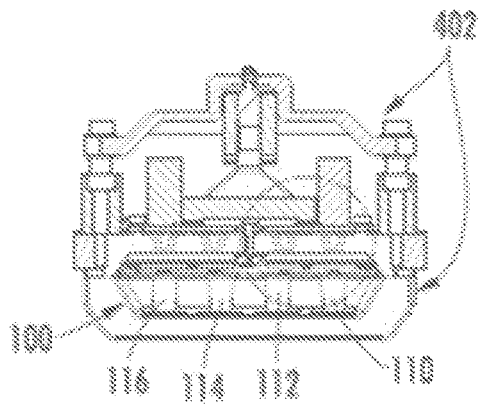
Figure 19O:
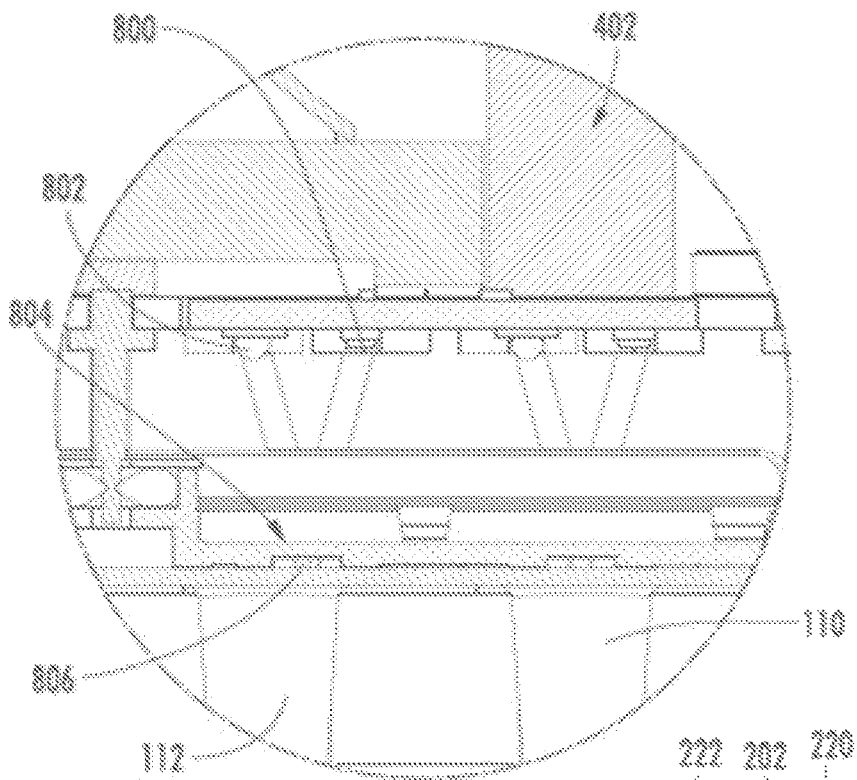
Figure 19P:
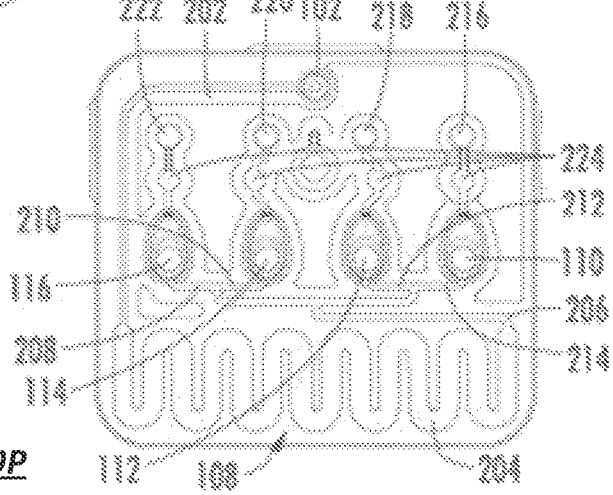

The level of sample in each chamber can also be monitored. For example, as shown in FIG. 19M-19P, the level of fluid in each chamber can be monitored optically. FIG. 19M is a schematic illustration of an example consumable cartridge placed in an example hemostasis evaluation system. FIG. 19N is a schematic illustration of a cross section taken across line B-B of FIG. 19M. FIG. 19O is an expanded schematic illustration of the circled portion of FIG. 19N. FIG. 19P is a schematic illustration of an example consumable cartridge.

Whether a desired level has been reached in a given chamber can be indicated by a LED or other visual indicator. Employing a single light beam from an LED emitter 802 reflecting off the chamber at a blood detection target reservoir 224, which is then detected by a detector 800 can be optionally used to optically monitor chamber fluid level.

For example, blood entering a test chamber reduces reflection of light originating from an emitter 802 located alongside the detector 800, and pointed at the test chamber. A dual beam approach can be used whereby two sources of different wavelengths were reflected off the test chamber. Blood has a deep red color that can be differentiated by comparing the red wavelength reflection to that of another colour.

The difference in intensity of the reflected red light alone is sufficient to determine when blood has entered a chamber. The red light intensity reflected from the test chamber containing blood was about one-half that of the well containing air, and about two-thirds of that from the well containing water.

To control the temperature of the biological sample entering the test chambers the cartridge 100 can comprise a heat exchanger in communication with the channel 204. The heat exchanger can be used to maintain, elevate or lower the temperature of the biological fluid before analysis in each test chamber. Optionally, the temperature of biological fluid for analysis in each test chamber is the same such that common portion of the channel system, as shown in FIG. 2, is subject to temperature manipulation by the heat exchanger. Optionally, in non-pictured embodiments, the temperature of biological fluid entering each test chamber can be separately controlled.

For example, to heat the biological fluid, it can be passed through the channel 204 through a polystyrene labyrinth held against a copper block. The copper block can be thin (for example under 2 mm) and sized just larger than the labyrinth to minimize the thermal mass. A thermistor can be embedded in the block so that a control circuit could maintain a steady set temperature in the block. A heater is used that optionally comprises two Watlow® (St. Louis, Mo.) serpentine foil heating elements bonded to a flexible kapton plastic substrate, and the interface between the block and the heater can be a thin layer of silicone heatsink compound.

Various flow rates, for example, up to and including 5.99 ml/min or 6.0 ml/min can be used, and power input to the heater can be varied optionally between 8 and 16 Watts. Blood or other biological fluid can be heated in the cartridge from ambient temperature (approximately 20° C.) to 37° C. at a nominal flow rate of 6 ml/min, which is fast enough to fill the cartridge in 20 seconds. The surface area of the labyrinth used was less than 8 $cm^2$.

Physiologically, the process of coagulation is highly dependent on the temperature at which it takes place. Under normal conditions, coagulation occurs at body temperature (37° C.), which is optimal for the proper enzymatic action of the clotting factors in the cascade.

Blood can be warmed from its incoming temperature, ranging between 18° C. and 37° C., to an arbitrary or desired temperature, such as body temperature, of 37° C. by passing through a serpentine channel in close proximity to a heater block. To accomplish the heating in a short time over a short path the block can be warmed to almost 60° C. when the incoming blood is at the lower end of its temperature range. The temperature of the blood can also be measured and the heater block can optionally be adjusted to a temperature, ranging from 40° C. to 58° C.

Figure 19Q:
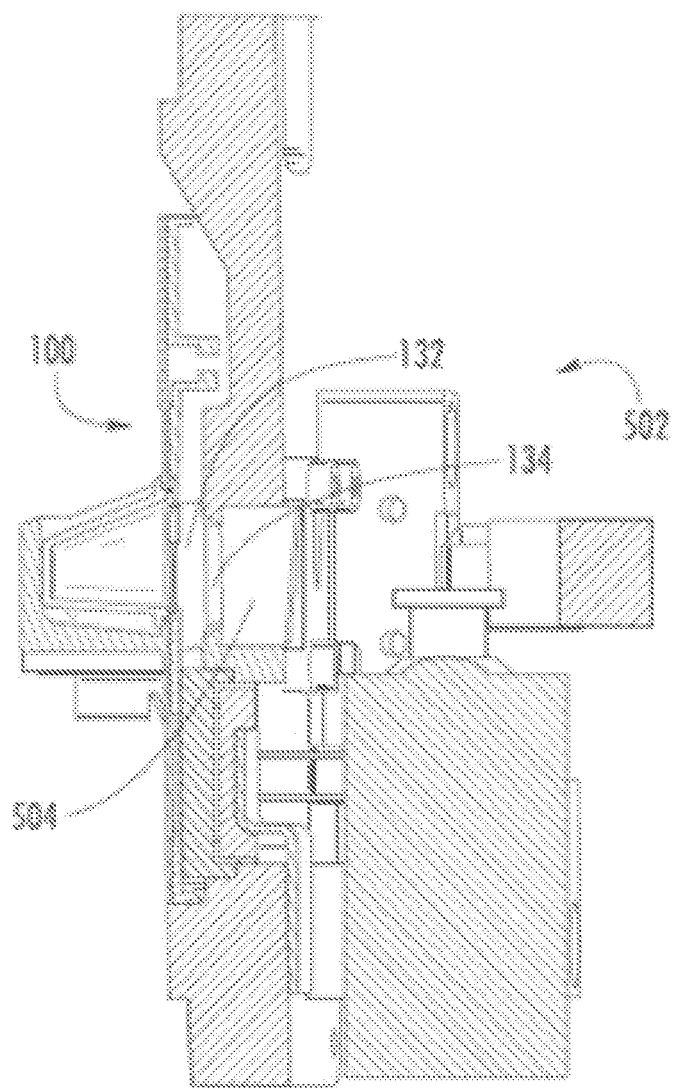
FIG. 19Q is a schematic illustration of a portion of a system for evaluating hemostasis.

To measure the temperature a sensor can be incorporated in the system 300 (FIG. 19Q) or in the cartridge. Optionally, a thermistor or thermocouple placed in physical contact with the cartridge or blood and an IR thermometer is pointed at the cartridge or blood. In either case the cartridge may incorporate a small well through which the incoming blood passes, rather than having direct contact with the blood. When the cartridge's material (polystyrene) is thin and the blood is kept moving through the well, then the larger heat capacity of the blood ensures the well's wall temperature is close to that of the blood. Optionally, a window allowing the passage of IR is used. The window can comprise a thin layer (e.g. 20 um or less) of polyethylene or polystyrene.

Temperature changes can occur in the body due to fever or in hospital settings such as the emergency room (ER) or operating room (OR). Trauma patients arriving at the ER are treated with large volumes of intravenous saline, which lowers body temperature to as much as 17° C. In the OR, patients undergoing cardiac bypass surgeries (CPB) have their entire blood volume pass through a lung-heart machine, which also lowers blood temperature and can adversely affect coagulation. Also, if there is a lag of time between the time of blood draw and the measurement, the temperature of blood is given time to change.

Styron® 666 (Styron Inc. Berwyn, Pa.) polystyrene and the microfluidic heat exchanger channel 204 allows a blood sample to be warmed by a copper block outside of the cartridge that is kept at a constant 37° C. When a sample enters the cartridge at temperatures substantially lower than 37° C., it is optionally desirable to use a cartridge modified to allow for more rapid heating of the biological sample. For example, in a model that simulates the temperature changes over time of blood entering the polystyrene cartridge at 17° C., Styron® 666 was found to reduce ability to heat blood and the blood exiting the heat exchanger did not reach 37° C. These shortcomings of Styron® 666 are due to its relatively low thermal conductivity. When more rapid or efficient heating of the biological sample is desired that is possible through Styron® 666, the cartridge can include materials with higher thermal conductivity than Styron® 666. For example, a thermally conductive polymer (E1201®) from Cool Polymers Inc. (North Kingstown, R.I.) with improved thermal conductivity properties can be used. This polymer can form a portion of the cartridge between the heating block and the channel 204. By using this polymer in a portion of the cartridge between the heating block and sample, the sample can be more efficiently heated. For example, FIG. 11 shows that in a cartridge comprising this material blood entering the heat exchanger at 17° C. reaches 37° C. within 15 seconds.

Cartridges optionally include both materials, E12010 and Styron® 666, in order to improve the heat transfer to the sample with E1201® on the heated side while maintaining flow visibility on the other side of the consumable with the Styron® 666. Another alternative is to use E1201® as an insert that fits over the copper heater and into a chassis made out of Styron® 666. This is optionally accomplished by overmolding the separate pieces into one single piece or affixing the E1201® to the Styron® chassis by means such as laser, ultrasonic or RF welding. Changing the geometry of the E1201® insert to fit into the larger chassis as a puzzle piece can further improve assembly of the separate parts and help seal the microfluidic flow chambers. It may also be desirable to cool the biological fluid in the cartridge. In these example, and similar to when heating is desired, the cartridge can include materials with higher thermal conductivity than Styron® 666. For example, the thermally conductive polymer (E1201®), described above, with improved thermal conductivity properties can be used. This polymer can form a portion of the cartridge between a cooling device, such as a peltier cooling device, and the channel 204. Using this polymer in a portion of the cartridge between the cooling device and sample, the sample can be efficiently cooled.

Each test chamber can comprise one or more reagents useful in the analysis of one or more indices of hemostasis. Optionally, the reagents are lyophilized. Optionally, one or more lyophilized bead type reagent is used. For example, the lyophilized bead can be a LyoSphere® produced by BioLyph (Minnetonka, Minn.). A self-contained lyophilized bead is a format that allows for immunochemical and clinical chemistry reagents requiring two or three components that are incompatible as liquids because of their pH level or reaction to one another to coexist compatibly. Because such lyophilized beads are stable and nonreactive, chemicals can be packaged together in the same test chamber.

To produce lyophilized reagents, a lyophilizer device can be used. For example, the reagent for a given test chamber can be frozen to solidify all of its water molecules. Once frozen, the product is placed in a vacuum and gradually heated without melting the product. This process, called sublimation, transforms the ice directly into water vapor, without first passing through the liquid state. The water vapor given off by the product in the sublimation phase condenses as ice on a collection trap, known as a condenser, within the lyophilizer's vacuum chamber. Optionally, the lyophilized product contains 3% or less of its original moisture content. The lyophilized product, which may be a pellet, can then be positioned in each test chamber. Once placed in a test chamber, the test chamber can be sealed to prevent unwanted rehydration of the product.

To locate the lyophilized reagents in the test chambers, the components can first be lyophilized and then the resulting lyophilized product can be placed in the test chambers. Using UV cure epoxy glue or a welding process (such as ultrasound or RF welding), the lens assembly is sealed over each of the test chambers. The assembled cartridge can be sealed in a vapor proof barrier (e.g. a bag) and the vapor barrier can be sealed to preserve the dehydrated nature of the product in the test chambers. When ready for use, the cartridge can be removed from the bag or vapor barrier and placed into an analysis system 300, which is described in further detail below.

Anti-static treatment of plastic cartridges is optionally used with the lyophilized reagents. Lyophilized reagents are inherently devoid of water, granting them significant electrical insulation.

Materials that are electrical insulators more readily build up static charge than materials that act as electrical conductors. This can create problems with process control when assembling the cartridges and loading the reagents. Since the cartridges are optionally made from an electrically insulating material (polystyrene, for example), it is not likely to dissipate a static charge build up within the lyophilized reagents. As a result, lyophilized reagents can statically adhere to the interior walls of the consumable. In order to prevent this from occurring, three techniques are optionally implemented to remove static build-up.

Air ionization is a method that passes directed, ionized air over a target material to neutralize residual static charge on the material surface. Directing ionized air at one or more cartridge test chamber and/or the reagents during the assembly process improves manufacturability by reducing the adherence of the reagent bead to the cartridge test chambers.

A second method implements cartridge construction using a plastic material that exhibits significantly more conductivity than standard injection molding materials. RTP PermaStat® (Winona, Mass.) plastics are an example of such materials. The use of this material for the cartridge reduces the adhesion of the lyophilized reagents to the cartridge test chamber walls.

Third anti-static, liquid sprays are used to temporarily create a dust-free coating on optical lenses and equipment. These sprays reduce static charge on the target surface and are useful for static reduction during the cartridge assembly process.

When the lyophilized reagents are exposed to the fluid sample, they can generate foam that floats at the surface of the sample in the test chambers. As illustrated in FIGS. 10A and B, the consumable cartridge 1002 optionally comprises a fluidic circuit 202 that delivers the sample from an external vessel, such as a syringe or vacutainer, into one or more test chambers (110, 112, 114, 116) were measurements are performed.

FIG. 10A shows an example fluidic circuit that can be implemented in a consumable cartridge 1002. This circuit includes an entry port 102, a channel 202, at least one test chamber (110, 112, 114, 116), a filter 1004 and an exit port 1006. The biological sample can be delivered within the chamber by applying a vacuum at the exit port, with the filter allowing air to escape but stopping the fluid. A variety of different reagents can be placed within the test chamber, for example, as described throughout. In order to generate accurate measurements, the reagents are mixed within the sample before testing is initiated. For example, ultrasound emitted into the test chambers can be used to mix the reagents with the sample as described below.

Figure 19R:
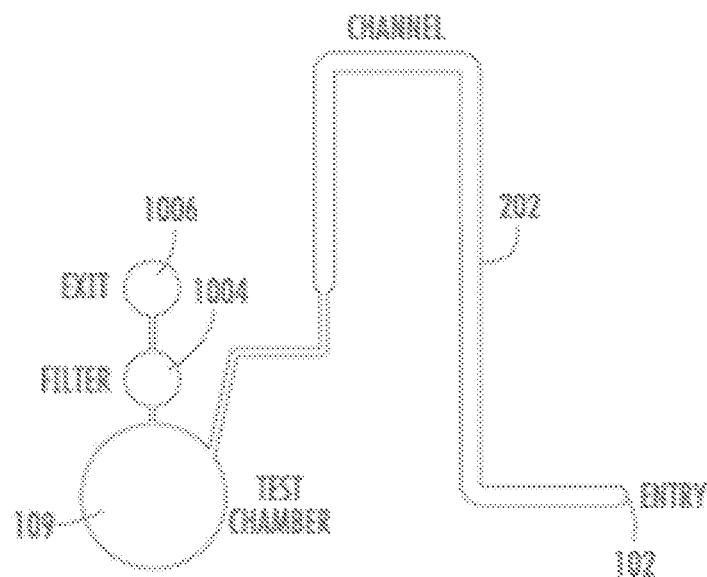
FIGS. 19R and 19S are schematic illustrations of an example sample flow pattern for use with the described devices and systems and of an example cartridge for evaluating hemostasis.
Figure 19S:
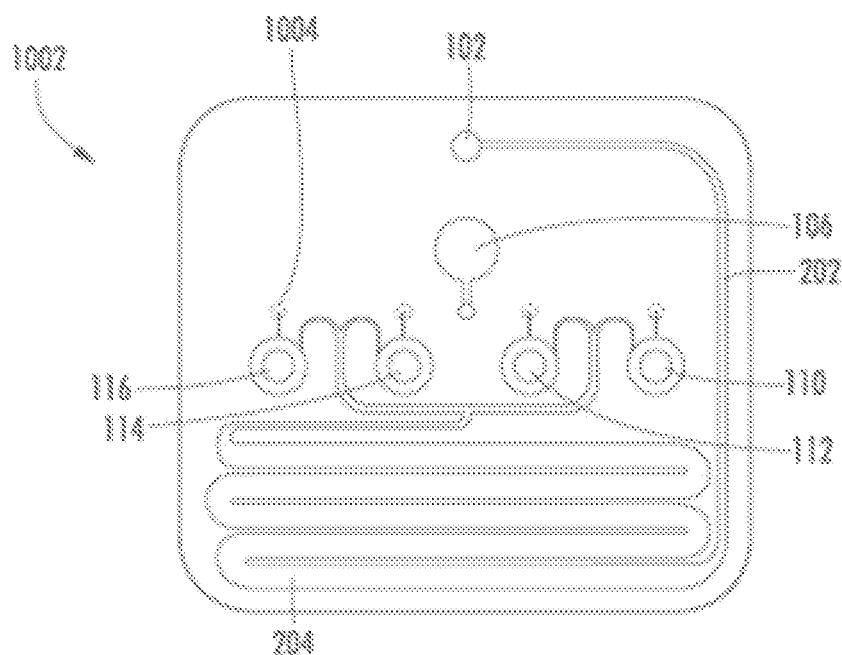

As shown in FIGS. 19R and 19S, to improve mixing of the foam, a biological fluid sample can flow through the channel 202, which enters the test chamber at the side on a tangent to the chamber. Furthermore, the change in channel diameter from large to small increases the flow velocity (conservation of flow rate) at the entrance to the test chamber. This high flow velocity, in collaboration with gravity, helps generate a re-circulating rotational flow pattern that improves mixing and reagent dispersion with the sample. As the flow enters from the side, it causes any formed foam to be pulled into the flow stream and pushed below the surface.

FIG. 19S shows a flow pattern implemented in a consumable cartridge designed for injection molding. The fluidic circuit has been repeated four times in order to deliver the sample and mix reagents in four different test chambers. The circuit presented in FIG. 19S also includes a serpentine heat exchanger to adjust the temperature of the incoming sample to a desired level.

Reagents are mixed with the sample before testing is initiated. Mixing of the reagents can be accomplished using passive and/or active mechanisms. Passive methods include, for example, the use of serpentine channels and embedded barriers to create flow turbulence. Active methods include, for example, magnetic beads, pressure perturbation, and artificial cilia. The consumable cartridge contains a lens that focuses ultrasound energy within the sample that can be used to generate streaming and mixing. The lens, also referred to herein as a lens assembly, or sound focusing assembly, is designed using a soft material, such as a thermoplastic elastomer 134, in conjunction with a rigid substrate 132, such as polystyrene. This combination provides a dry ultrasound coupling that does not require the use of any fluid or gel couplant. Note that the same lens and ultrasound driver used for hemostasis measurement can be used in this matter to provide mixing Increasing acoustic energy for mixing can be delivered by, for example, increasing pulse length, pulse amplitude or pulse repetition frequency.

Mixing can also be provided by a variable magnetic field applied by a series of coils placed outside a test chamber or each test chamber. A small magnetic bead or magnetic stirrer can be placed within a test chamber and when the fluid sample enter the chamber, the current across the coils can be modulated in order to generate a variable magnetic field. This generates motion of the magnetic bead or magnetic stirrer which in turns generates mixing of the sample with the reagent.

The exposure of blood to surface proteins, such as in the case of collagen or von Willebrand factor (vWF) on damaged blood vessel walls is an essential part of the coagulation process. These proteins not only contribute to the clotting cascade but also modulate several steps leading to clot formation and hemostasis.

Although exposure to these proteins is essential to the coagulation cascade, standard point-of-care (POC) coagulation assays and devices fail to take this interaction into account. Optionally, the test well(s) and/or channel(s) of a consumable cartridge, such as those described herein, are coated with such surface proteins for the measurement of coagulation within a POC medical device.

The use of surface protein coatings includes collagen, vWF, fibronectin and any other molecule that modulates coagulation such as fibrinogen and thrombin. A layer of protein on a substrate (glass, polystyrene, polypropylene) creates binding sites that allow the mediation of receptor-ligand interactions between the substrate and other biological materials such as blood in a manner that improves the assessment of coagulation or provides new testing information.

The interior surfaces of a consumable cartridge can be coated using for example: (1) a layer of such proteins by covalent binding using linker molecules, (2) covalent binding using photochemistries or (3) simple protein adsorption. Linker molecules such as streptavidin or avidin and biotin can be used for this purpose. With linker molecules, the surface of any interior portion of the cartage that will be exposed to the biological sample is biotinylated (coated with a layer of biotin) using commercially available biotin that is conjugated to a reactive group that non-specifically and covalently binds with the substrate. A solution with a high concentration of streptavidin or avidin, which have high affinity for biotin, is added to create a layer of streptavidin/avidin bound biotin. Addition of biotinylated protein (collagen, vWF, fibronectin, thrombin, fibrinogen) then creates a layer of protein bound to the test well surface that specifically affects coagulation through interactions with plasma proteins and platelets.

Protein adsorption can be accomplished by filling the wells with a highly concentrated protein solution. Adsorption to the plastic surface takes place almost immediately depending on temperature, ph, surface charges, surface morphology and chemical composition. The solution can then be removed and the surface air dried. Brushing a highly concentrated protein solution on the surface of the wells or dipping the wells into such a solution will accomplish the same purpose.

The concentration of molecules in the solutions used for coating, whether using linker proteins or adsorption, can be changed to modulate the amount of protein that binds the substrate and, thus, modulate the effects on the coagulation cascade in a way that is relevant to physiology and hemostasis.

The transducers in this preferred embodiment are preferably in the 10 to 100 MHz range, more preferably 20 MHz. Though the measurement can be made with only one transducer, a pair is most preferably used, one on each side of the collected sample. Locating the pair in this fashion allows both pitch-catch and pulse-echo signals to be measured as shown in FIG. 8. The fixture holding these transducers preferably ensures reliable acoustic coupling between the sample chamber and the transducers.

The signal generator generates a simple electronic signal of sufficient duration and amplitude to operate the transducers. The frequency of the signal is appropriate for the selected transducer, and is preferably from 1 to 3 cycles in length. The amplitude of signal should be as high as possible without exceeding the transducers' ratings. Another amplifier circuit may be needed to maximize the signal-to-noise ratio. With the appropriate electronics (discussed above) this hardware can also determine the relevant clinical parameters using other measurements such as measuring the frequency response of the chamber to determine how much it resonates at each frequency.

Device control may be through an on-board processor, or through a programmable logic controller that may be shared with the other embodiments for determining clotting parameters. The signal processing algorithms preferably include one or more of the following: noise filtering, averaging, and automatic gain control. Detection logic preferably includes zero-crossing detection. Zero-crossing detection is a method for accurately measuring the time at which a signal like a wave burst arrives. In this method, the wave is timed by detecting precisely when the signal crosses zero. Because most typical bursts last several cycles and therefore cross zero multiple times, a single crossing is preferably used consistently in a given application of the method. For example, one embodiment is to use the 2nd (or 3rd or 5th) zero crossing of every burst as the consistent timing point.

A spline based method or principal component method may also be used as detection logic.

Another preferred embodiment (B) provides a handheld device suitable for use with a drop of blood and uses disposable transducers. Like embodiment (A), this embodiment, described below, includes a handheld device and will measure hematocrit, the hemoglobin content, and/or the other red blood cell indices. Unlike embodiment (A), though, embodiment (B) preferably includes disposable transducers, which are preferably integrated into the sample chamber.

The test chamber of this embodiment may be in either format described in Embodiment (A) with the exception that the test chambers in Embodiment (B) preferably include one or two disposable transducers built into the test chamber. This chamber with would then use an electrical connection to the test device instead of acoustic coupling. These disposable transducers may be preferably manufactured using micromachined capacitive elements (MEMS) to minimize cost.

The disposable transducers are preferably in the 10 to 100 MHz range, more preferably 20 MHz. A pair of these transducers is preferably used, one on each side of the collected sample. These disposable transducers may or may not be in contact with the drawn blood sample.

Another preferred embodiment (C), described below, provides a handheld device suitable for use with a tube of blood and using permanent transducers. This embodiment varies from (A) and (B) in that a larger volume of blood is used. In this embodiment, the user draws a tube of blood from the patient via venipuncture. The sample is placed into the device and the device displays the hematocrit, the hemoglobin content, and/or the mean cell volume. The device is preferably handheld, battery powered, and portable. The sample chamber is preferably disposable.

The test chamber may be a medical tube configured for the introduction of reagents. The tube is inserted into the invention and the transducers couple directly to its outside surface. Two modes of signal propagation are preferable. In the first, the signals are transmitted perpendicularly to the tube axis and transmit through the tube for pitch-catch measurements and reflect off the walls for pulse-echo measurements as shown in FIG. 8. In the second mode, the signal travels along the axis of the tube or perpendicularly but reflect from a disposable, two-step reflector of known size that has previously been inserted into the tube as shown in FIG. 6.

In another preferred embodiment, the measurement is made in-vivo, without drawing any blood from the patient. The device is held against the patient's skin and sends ultrasound into the patient. The backscatter, speed of sound, attenuation, and other ultrasonic measurements are calculated from the received signals and used to infer the blood properties. An array transducer is preferable so that the device can dynamically steer the sound beam and alter the focus length to search for a large artery or vein. If an array transducer is chosen, an appropriate signal generator to control the array and allow the beam-steering is preferred.

III. Use of HCT for Improved Hemostasis Characterization

In another embodiment, the HCT and associated parameters are used in conjunction with conventional measures of hemostasis. Variations of HCT level, such as in the case of hemodilution, affect the results of conventional coagulation tests such as the PT, PTT and ACT.

Figure 18:
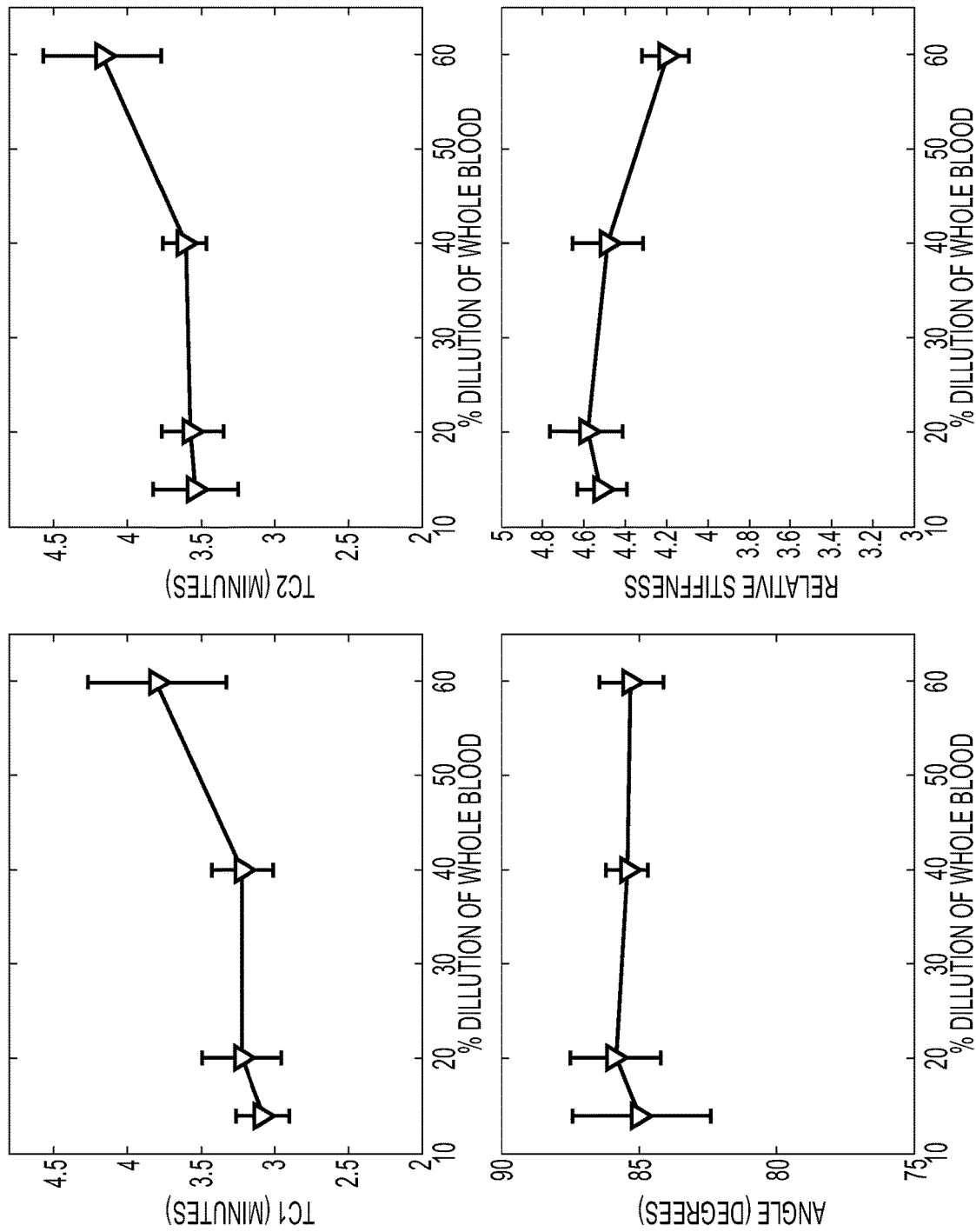
FIG. 18 is a plot of the effect of hemodilution on sonorheometry parameters.

FIG. 18 shows how sonorheometry parameters TC1, TC2, angle, and estimated stiffness S vary as a function of hemodilution, which causes the HCT to change. The data shown in this figure was obtained from whole blood samples from 5 healthy individuals. Increasing amounts of normal saline were added to the whole blood samples to reduce the HCT. Since sonorheometry uses ultrasound signals to perform measurements of hemostasis and the same ultrasound signals can be used to estimated HCT, the parameters output by sonorheometry can be corrected to adjust for the HCT effects shown in FIG. 18.

In another embodiment, sonorheometry can be further modified to output and display HCT level in addition to the hemostatic indexes presented in Table II. Transfusion protocols often use the HCT value as a trigger to transfuse packed red blood cells (RBCs) units. Therefore, in a single device sonorheometry can output a index for (1) coagulation factors (intrinsic and/or extrinsic), (2) platelet function, (3) fibrinogen, (4) fibrinolysis, and (5) HCT so that it can provide guidance for the transfusion of: (1) fresh frozen plasma, (2) platelet concentrates, (3) cryoprecipitate, (4) antifibrinolytics, and (5) packed RBCs, respectively.

In a further embodiment, HCT measurements can be used to improve or correct coagulation parameters to be closer to those obtained for plasma measurements such as described by Amukele T K et al. *Comparison of Plasma With Whole Blood Prothrombin Time and Fibrinogen on the Same Instrument.* American Journal of Pathology 2010. For example, the prothrombin time (PT), international normalized ratio (INR) and fibrinogen viscoelastic assays can vary due to the impact of HCT when in certain ranges.

In one embodiment, the present invention accounts for the impact of HCT by comparing the HCT to an assumed value (if any) or by determining a range in a clotting parameter in which the measured parameter is particularly sensitive to HCT and communicating this to the healthcare personnel.

Also, the present system or process can use empirically determined relationships characterizing the variation of hemostasis parameters with changes in HCT and other oxygen transport parameters to correct or adjust the estimated hemostasis parameter. For example, the system could apply linear regression to empirical data to determine a corrected hemostasis parameter. Also, the system could use a higher order curve, such as a parabola, to determine a corrected hemostasis parameter.

Physiological adjustments as defined herein use the relationships within living or biological systems to correct or adjust measurements. For example, the above-described use of a known physiological relationship between HCT and hemostatic parameters is a physiological adjustment.

Physical adjustments as defined herein use pure physical principals independent of living systems to correct or adjust measurements. For example, the use of speed of sound to calibrate the applied radiation force is a physical adjustment.

IV. Integrated System for Determination of Hemostasis and Oxygen Transport Parameters Integration of the determination of oxygen transport parameters and hemostasis parameters is facilitated by several improvements over the prior art. The term "integrated" as used herein refers to a system or process that uses common or shared hardware or a common sample. Also, data from the same transmission could be used as a form of integration.

Thus, the system may determine hemostatic and oxygen transport parameters using the same blood sample and/or the same transducer or transducers, or at least common hardware and/or sample portions. Integration therefore reduces the time, cost and complexity of determining these important clinical hemostatic and oxygen transport parameters.

The system or device achieves this by being able to operate in two modes without entirely or at all changing the sensor or sample configuration. Prior art systems, on the other hand, for example may use a twisting weight supported by a wire to determine clot stiffness. Such systems are incapable of transmitting or measuring sound through a blood sample. Conversely, prior art systems for measuring the speed of sound through blood are incapable of determining hemostatic parameters. They cannot, for example, induce displacements of clots or measure the induced displacement.

Figure 26:
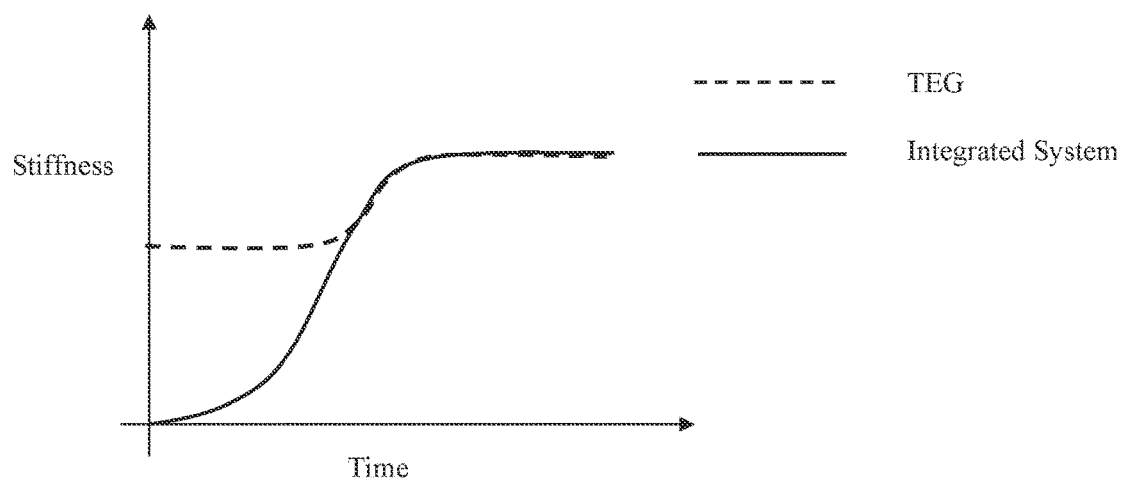
FIG. 26 is a plot comparing a prior art TEG system's sensitivity to the present system.

Also, prior art systems do not have the capabilities of the present system or device to determine hemostatic parameters. The present system or device may also have the ability to dynamically adapt to the properties of the sample through a large stiffness range. FIG. 26 schematically illustrates the impact of the improved dynamic range on clot stiffness measurements compared to a conventional device.

Another advantage is that the system may also be configured to adapt to or adjust to the characteristics of the clot. The adaptation capability can apply a "light touch" to the clot by changing the emitted sound signal to adjust to the properties of the clot. This avoids tearing of the clot. The prior art pendulum systems are relatively insensitive to softer clots and/or can tear or damage a clot during testing, distorting the measurements.

In addition, the ability of the integrated system to adapt reduces electronic noise for greater sensitivity to small echoes. The present system or device has a relatively high sensitivity throughout the large stiffness range.

Also, the system is capable of an increased rate of pulses, resulting in greater forces, further expanding the dynamic range. The pulse frequency range may, for example, be from 1 Hz to 50 kHz. Overall, the system or device may be capable of measuring tissue stiffness in a range of five or more ($10^5$ or greater from softest to hardest) orders of magnitude.

Another advantage of the system or device is its low number of moving parts compared to prior art mechanical systems that employ weights or cantilevers. These attributes offer another advantage by facilitating miniaturization of the system or device. Also, because the sensing system requires no moving parts, the sensing system performs better when subjected to environment vibrations.

An exemplary process or system 200 for integrated determination of one or more hemostasis parameters and one or more oxygen transport parameters is shown in FIG. 19. A consumable cartridge or other container 30 is inserted 202a by the user into the hemostasis system assembly 1. A syringe containing a blood sample 51 is then manually attached to the consumable.

User input is provided 204a to the hemostasis system assembly 1. For example, the user may confirm that the consumable 30 is in place by pressing a "start" button. Other input may be provided that facilitates or improves determining of the parameters. For example, the input may include identification of the patient associated with the sample.

The device 1 clamps 206a the consumable by applying pressure to the consumable. This pressure may form an acoustic coupling between the consumable and an acoustic wave generating transducer or device 10. The consumable 30 may include aspects of the acoustic wave generating device 10, such as consumable lenses.

The consumable 30 is heated 208a to a temperature that facilitates blood coagulation. A two-way pumping mechanism of the assembly 1 draws or aspirates 210a blood from the sample 51 into the consumable 30.

The blood sample 51 is acoustically mixed 211 with a reagent in a well of the consumable.

Parameters are measured 212a by repeatedly cycling through data acquisition processes in each transducer channel (e.g., 4 transducer channels) while blood coagulates in the consumable 30.

Data is acquired 222a and processed 224a from each channel of the transducer 10. Each channel may have dedicated acquisition 222a and processing 224a before the system 1 moves on to the next channel.

Acquisition 222a may include two steps, radiation force (RadFor) data acquisition 226 and calibration data acquisition 228.

Figure 20:
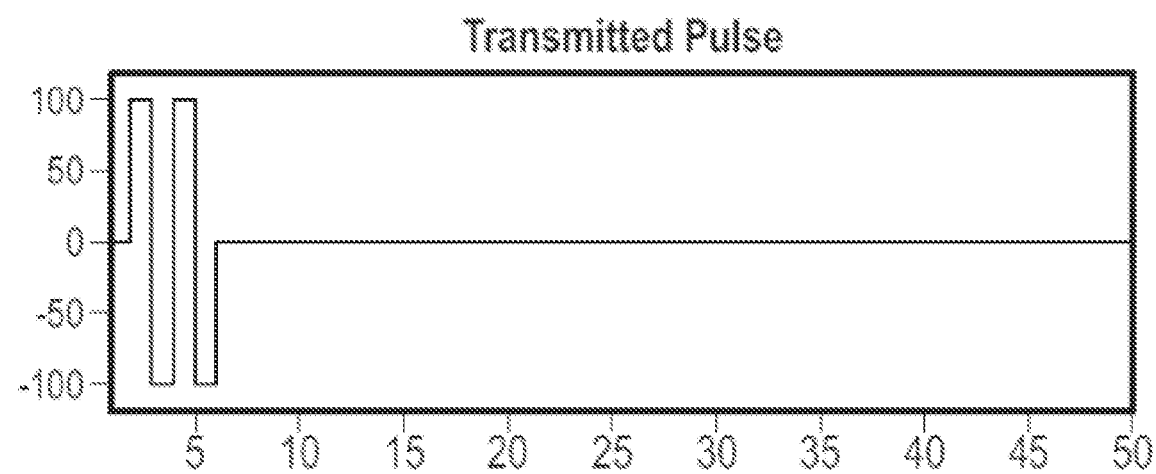
FIGS. 20 and 21 are a short ultrasonic pulse with a correlation function such as may be used in the system of FIG. 19.

As shown in FIG. 20, radiation force data acquisition 226 includes transmission of an ensemble of relatively high intensity acoustic pulses into the blood sample. The system 1 then receives acoustic echo data back from each individual pulse or from a selected subset of the transmitted pulses. Each ensemble of acoustic pulses may be adaptively controlled.

Calibration data acquisition 228 includes transmission of a single acoustic pulse that targets the back of the consumable 30. From this pulse the system 1 derives values for the speed of sound in the blood sample and the acoustic attenuation. More details about radiation force data acquisition 226 and calibration data acquisition 228 are described below.

Acquired data is processed 230 by application of several sub-processes, including estimating stiffness 232, estimating HCT (or other oxygen transport parameter) 234, updating the configuration 236, estimating signature parameters 238 and estimating indices 240.

Estimating stiffness 232 includes accepting raw data acquired from the radiation force acquisition 226 and processsing it to yield a single stiffness estimate based on the transmitted radiation force ensemble parameters and the calibration parameters.

Estimating HCT 234 includes deriving a speed of sound and acoustic attenuation from the calibration data acquisition 228 by applying a mathematical model. For example, the estimation sub-process could use a linear mathematical model correlating the speed of sound to hematocrit.

Update the configuration 236 is part of the adaptive acoustic system and includes accepting the maximum displacements acquired during radiation force acquisition 226 and the transmitted ensemble configuration to determine the configuration that will be used for the next ensemble of pulses. The adaptive process is described in more detail below.

Estimating signature parameters 238 includes accepting the single stiffness value from the estimating stiffness 232 sub-process into a matrix containing all of the measured stiffness values for that channel. This sub-process combines all of the stiffness data acquired thus far and fits a non-linear curve to the data. The signature parameters are determined from the non-linear curve. The signature parameters, for example, are the baseline stiffness, time to clot, rate of clot formation, time to lyse, post-lysis stiffness.

Estimating indices 240 includes computing hemostatic indices based on the signature parameters.

The acquisition 222a and processing 224a steps are cycled continuously for each of the four channels until the blood coagulation process is complete.

In a more detailed description of the radiation force acquisition process, each of a plurality of channels is configured to transmit Tx and receive Rx sonic energy to determine a point on a time displacement curve. The four channels generate four transmissions Tx0, Tx1, Tx2, Tx3 and receive four signals Rx0, Rx1, Rx2, Rx3.

Figure 24:
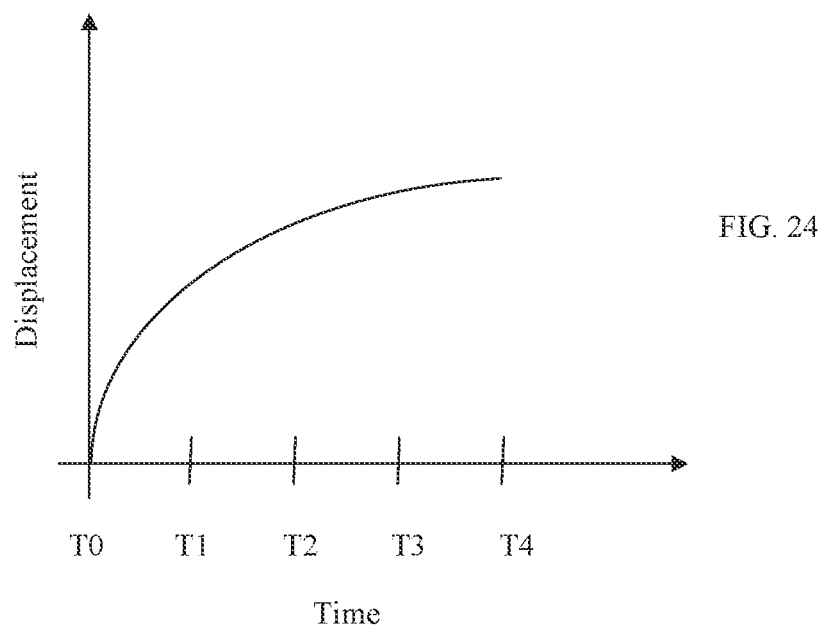
FIG. 24 is a plot of displacement over time of a clot measured by the system of FIG. 19.

The acquired data is then filtered to determine a time-displacement curve at four equal periods, as shown in FIG. 24. Filtration, for example, may be by a principal components filter, such as is described in U.S. Patent Application Publication No. 2009/0304246 to Walker et al. entitled REDUCTION OF ECHO DECORRELATION FACILITATING MOTION ESTIMATION which is incorporated by reference herein in its entirety.

The filtered points are then curve fit using a model, such as a viscoelastic model described above, to estimate a displacement at a time of interest. For example, displacements could be determined at a one second time interval.

Figure 9:
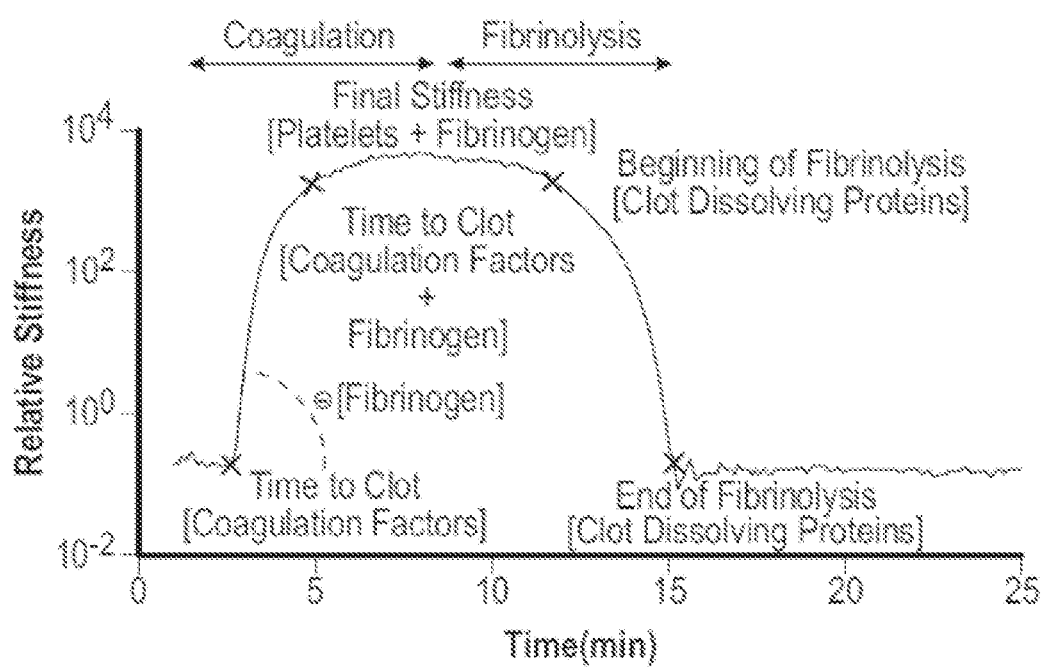
FIG. 9 is a plot of a curve showing evolving clot stiffness over time during hemostasis.

These curves are then used to determine a stiffness value throughout the hemostasis cycle, as shown for example by FIG. 9. Stiffness could be calculated at various intervals depending upon available or desired use of computational power. For example, a 6 second interval yields fairly robust curves while conserving processing power.

Since the amount of force applied is a function of pulse repetition frequency (PRF), the applied force can be adjusted by changing the PRF. The sensitivity could also be adjusted by changing the time at which the displacement is projected, such as to ½ second from 1 second.

Figure 27:
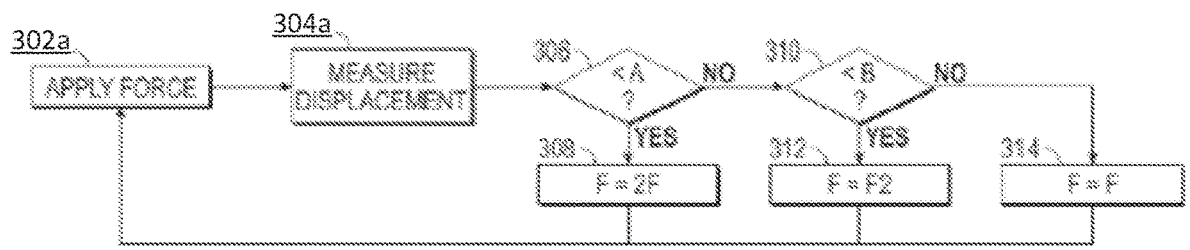
FIGS. 27 and 28 are flowcharts of application of adaptive force to a tissue sample.
Figure 28:
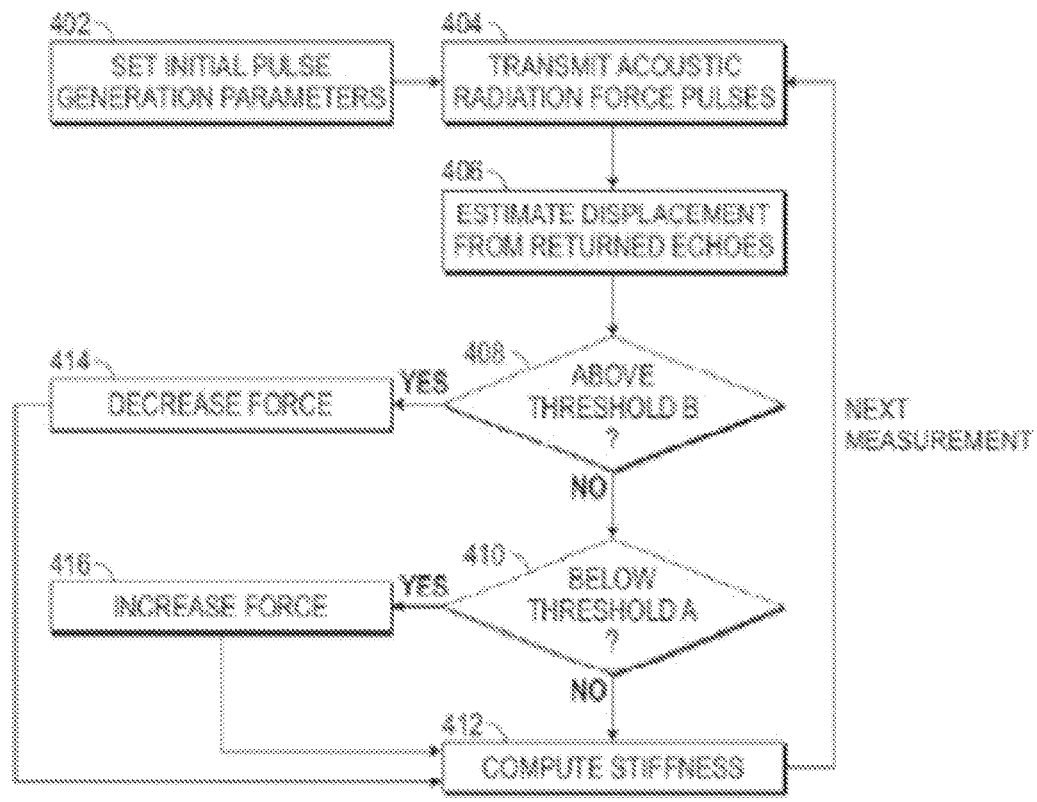

Dynamic adaptability of the present system or device is shown in PCT Patent Application Publication No. WO 2011/035162 to Walker et al. entitled ULTRASOUND-BASED METHOD AND RELATED SYSTEM TO EVALUATE HEMOSTATIC FUNCTION OF WHOLE BLOOD which is incorporated by reference herein in its entirety. FIGS. 27 and 28 show a principle and process of applying adaptive force to a sample for high dynamic range measurement performed at low strain levels according to an embodiment of the present invention.

FIG. 27 is a flow chart illustrating an example of the principle of applying adaptive force to a sample for high dynamic range measurement performed at low strain levels according to an embodiment of the present invention. In this embodiment, a minimum displacement threshold level "a" and a maximum displacement threshold level "b" are preset prior to application of force. At event 302a, force F is applied to the target being measured according to an embodiment of the present invention. At event 304a a displacement of the target that resulted from application of the force F to the target in event 302a is measured. At event 306, the measured displacement is compared to the minimum displacement threshold level "a".

If the measured displacement is less than "a", then the force F is increased at event 308 (e.g., doubled, in the embodiment shown in FIG. 2) and this greater force is then applied at event 302a to take the next measurement at event 304a.

If, on the other hand, the measured displacement not less than "a", then a comparison is made at event 310 as to whether the measured displacement is greater than maximum displacement threshold level "b".

If the measured displacement is greater than "b", then the force is reduced at event 312 (e.g., halved, in the embodiment shown in FIG. 2) and this lesser force is then applied at event 302a to take the next measurement at event 304a. If, on the other hand, the measured displacement not greater than "b", then the force is maintained at its current level at event 314 and the same force is applied at event 302a for taking the next measurement.

In the system or device, an increase of the force F may be accomplished by increasing the PRF. Conversely, a decrease of the force F may be achieved by decreasing the PRF.

Using the principle described with regard to FIG. 27, the present invention can carry out sonorheometry at low strains with a dynamic range of stiffness measurements of approximately five orders of magnitude. Of course, the present invention is not limited to increasing by doubling or decreasing by half, as any arbitrary multipliers can be implemented to carry out the described principle. Possibilities include greater than one for increasing, and less than one, but greater than zero, for decreasing. Likewise, as noted above, increasing and decreasing functions need not be limited to changing the PRF. They can alternatively be carried out by changing the pulse intensity integral (PII) or by changing both PRF and PII.

FIG. 28 is a flow chart illustrating use of adaptive radiation force sonorheometry to adaptively adjust the applied radiation force in order to maintain low strains and improve dynamic ranges (thereby increasing the signal to noise ratio) of stiffness measurement according to an embodiment of the present invention. At event 402, initial parameters are set for PRF and PII, thus defining the initial pulse generation parameters.

The initial PRF is set at a value with the range of from about 4 Hz to about 12 kHz, or less than or equal to 100 Hz, although the present invention is not limited to these settings. Pulses with as little as one cycle up to pulses with sixteen or more cycles can be used. Amplitude may be varied such as increasing (up to doubling, or more) or decreasing (down to halving, or less). In cases where an emission transducer of relatively low efficiency is used, PRF and PII may be set relatively higher. For applications to plasma, which has a lower viscosity than whole blood, relatively lower PII and PRF may be set. Also, when examining plasma, it may be necessary to add an acoustic scattering agent, such as polystyrene microspheres.

At event 404, acoustic radiation force pulses are transmitted to the target according to the PRF and PII that were initially set in event 402. At event 406 a displacement of the target is estimated or measured by sonorheometry, using echoes returned from the target. At event 408, the estimated displacement value is compared with the maximum displacement threshold value "b". If the estimated displacement value is greater than "b", then the force to be applied to the target in the next iteration is set to be decreased by decreasing the PRF and/or decreasing the PII at event 414 and a relative stiffness value (or absolute stiffness value in embodiments where the constants a and c are measured) is computed at event 412, using the estimated displacement value. Next, event 404 is carried out again by transmitting decreased force generated using the parameters from event 414.

If, on the other hand, the estimated or measured displacement value is not greater than "b" at event 408, then at event 410 the estimated displacement value is compared with the minimum displacement threshold value "a". If the estimated displacement value is less than "a", then the force to be applied to the target in the next iteration is set to be increased by increasing the PRF and/or increasing the PII at event 416 and a relative stiffness value (or absolute stiffness value in embodiments where the constants a and c are measured) is computed at event 412, using the estimated displacement value. Next, event 404 is carried out again by transmitting increased force generated using the parameters from event 414. Iterations can be carried out until all physiological observations that the observer is interested in have been made, e.g., until an experiment is ended, until a patient is released to another care center, until a clot completely dissolves, etc.

As another option, the systems of FIGS. 27 and 28 may include a curve comparison step in place of, or in addition to, or as part of, steps 306, 310, 408 or 410. This curve displacement step compares the measured time-displacement curve to an expected model curve. The fit of the measured curve to the expected model curve is quantified. If it is below the threshold the force is reduced. Without being wed to theory, the assumption is that the poor fit is because large displacements are causing signal decorrelation.

Sensitivity is related to the amount of force applied to the sample, which results in higher displacements.

Advantageously, as shown above, short pulses also do not smear as much due to the lack of overlap in the return signal. However, the overall amplitude of the response may be somewhat small. The return signal amplitude could be increased through an increase in the amplitude of the transmitted pulse. However, power limitations can curtail the size of the amplitude, especially in systems where the peak-to-peak power potential is limited to 200V because of the electronic components used. Longer pulses may result in a stronger "push" also, but can result in smear due to overlap in the return signal.

However, further advantageously, the present system and device may include processes for ameliorating the smear effects. For example, coded excitation could be used to improve force measurement and imaging.

Radiation force based sensing is limited by the available signal to noise. For sonorheometry, the fundamental signal is radiation force induced displacement. The noise is the error in estimation of that displacement. The signal (displacement) is determined, at a given material stiffness, by the applied radiation force:

$$F = W/c$$

Wherein W is the acoustic power and c is the speed of sound. Increasing force yields increasing displacement, improving the accuracy of the displacement estimates. While the speed of sound, like stiffness, is largely an intrinsic property, the applied acoustic power can be controlled by the system.

The applied acoustic power emitted by a pulsed system is a function of the pulse repetition frequency (PRF) and the acoustic Pulse Intensity Integral per pulse:

$$W = PRF * PII$$

The PRF can be greatly increased to increase force applied to the sample. Power increases, however, may be limited. Application of a high PRF may cause echoes from earlier pulses to overlap in time with the desired echoes from the most recently transmitted pulse. This makes it difficult to cleanly estimate displacement. Further, if the PRF is too high then it becomes challenging to transfer the digitized echo data from one transmission before echo data is digitized from the following transmission. For these reasons it is desirable to increase the power per transmitted pulse (Pulse Intensity Integral).

The PII in each transmitted pulse is proportional to the integral of the square of the acoustic pressure in that pulse. A first strategy is to increase the amplitude of the acoustic pulse. This can be accomplished by increasing the drive voltage of the transmit circuit. However, the circuitry of the emitter is usually limited to +/−100V to avoid damage.

The length of the emitted pulse could also be increased. One would maintain the same center frequency but increase the number of cycles in the transmission. This approach however will reduce the signal bandwidth and the axial resolution of the system. These changes may reduce the available window for measuring displacement by overlapping the desired region with signals from the undesired region. Further, the accuracy of displacement estimates is reduced as described by the Cramer-Rao Lower Bound.

The radiation force sensing could be improved if pulse length could be increased without degrading the axial resolution or bandwidth, such as by using coded excitation. For example, Barker Codes could be used. Barker codes are simple binary codes that have the property of having very short correlation lengths when convolved with the proper matched code. These codes preserve bandwidth and spatial resolution while still lengthening the transmitted pulse.

Figure 21:
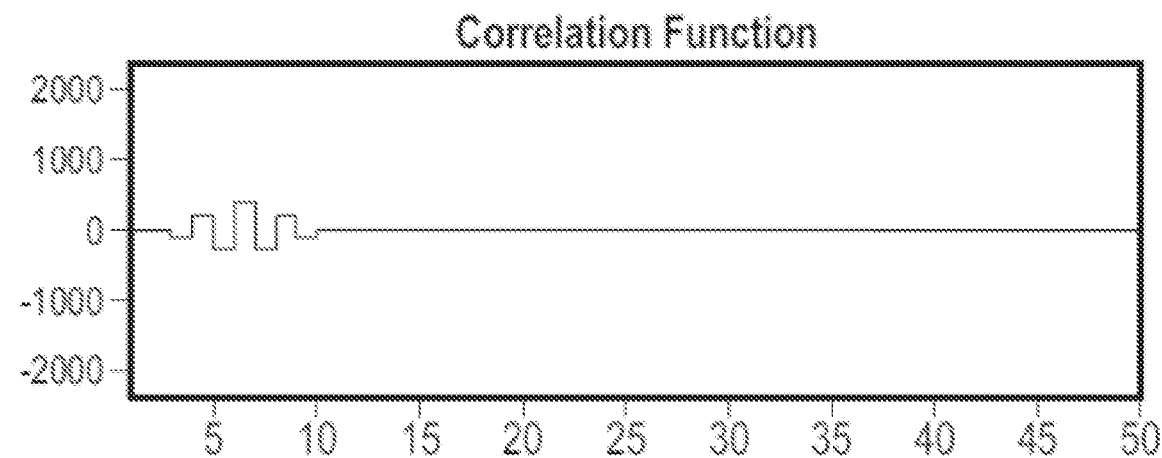

For example, a two-cycle transmit pulse is shown in FIG. 20. The associated correlation function shown in FIG. 21 is quite short, indicating that good spatial resolution in maintained. It is also quite low in amplitude however, indicating fairly low transmit energy.

Figure 22:
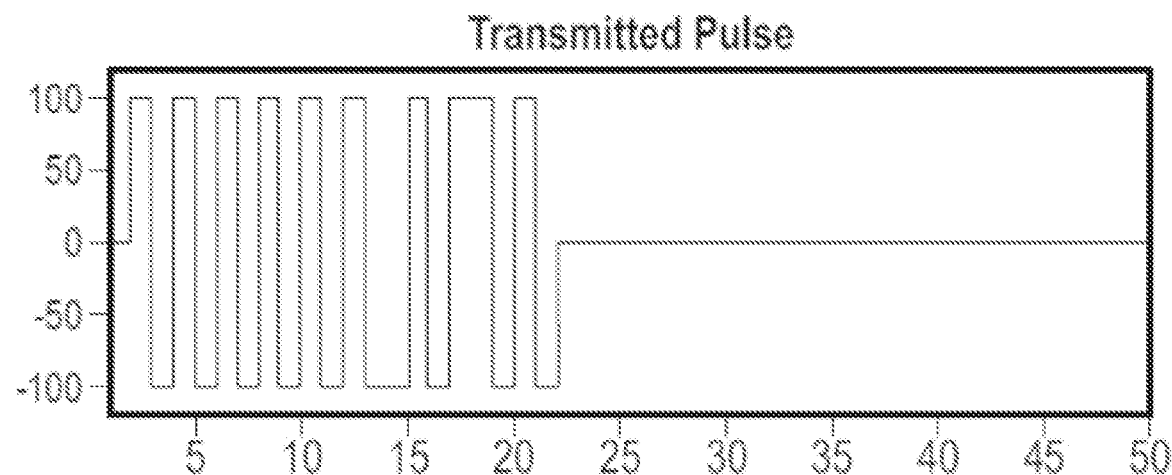
FIGS. 22 and 23 are a longer ultrasonic pulse with a correlation function such as may be used in the system of FIG. 19.
Figure 23:
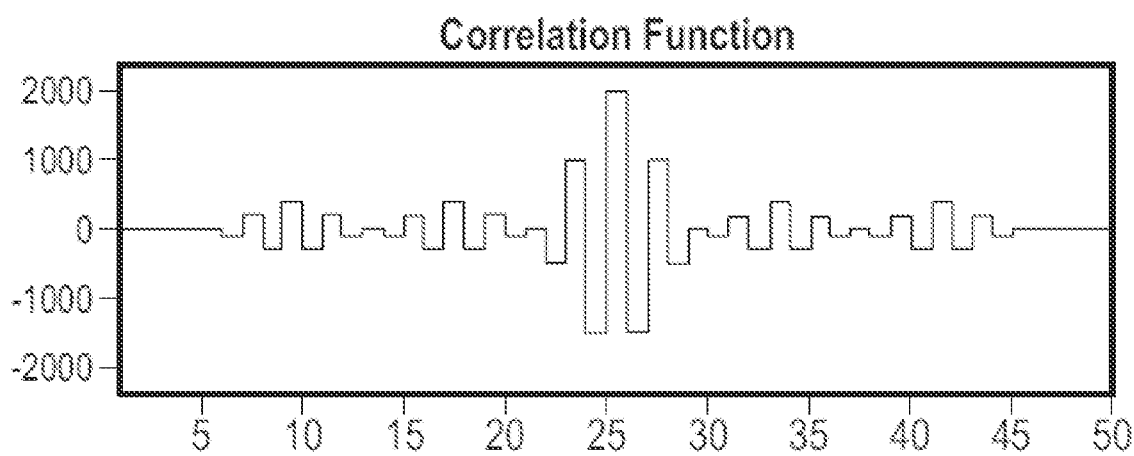

As shown in FIG. 22, the original two cycle transmit pulse is replaced by a version of that pulse convolved with a 5 sample Barker code (+ + + − +). The transmitted pulse is now five times longer, generating a significantly higher (5×) peak in the autocorrelation function. The transmission is much more energetic. The correlation function itself however remains quite short in duration, as shown in FIG. 23, indicating that axial resolution is largely preserved. Modest ringing is introduced, but this is a reasonable tradeoff for the large increase in displacement that will be achieved.

As can be seen above by the adaptive process, improving dynamic range may be a matter of incrementally improving the electronic signal-to-noise, increasing the applied force at one end (high stiffness) and reducing the applied force at the other end (low stiffness). At the low end may be a 2 cycle transmission at 4 Hz PRF. At the high end, a 13 point barker code with 2 cycle impulse response for a 26 cycle transmit at 32 KHz PRF may be employed. The high to low force variation is by a factor of 212,992.

Prospectively, the inventors believe a system could be built with two transmit waveforms voltages could be employed, such as +/−100 V and +/−25 V. Since the force depends upon the square of the voltage, the range would increase by a factor of 8 to 1,703,936.

Also, the inventors have observed the impact of the range of sensitivity to motion. At the high end, displacements as small as 0.1 micron may be estimated. At the low end, displacements may be as high as 75 microns (half a wavelength). This yields a 750× displacement range. Spline-based algorithm displacement estimators may yield a 750 micron measurement. A conservative motion estimation is therefore 1,277,952,000 and even as high as 12,779,520,000. Thus the dynamic range with "simple" signal processing is just over 9 orders of magnitude. With more sophisticated signal processing just over 10 orders of magnitude may be achieved.

Thus, even 5 orders of magnitude can be exceeded in the present system or device through various improvements. First, the use of two different transmit levels gives us almost one order of magnitude. Second, using barker codes gives us more than one order of magnitude. Also, a broad range of transmit pulse repetition frequencies is being used. Also displacement estimation noise is kept at a low baseline which, although not easy, is achievable. Generally, 5 orders of magnitude is enough to capture the stiffness range of blood in most instances.

The present system or device can also improve sensitivity through the use of multiple samples. For example, four wells with different reagents could be used to determine measurements within overlapping time periods.

Figure 25:
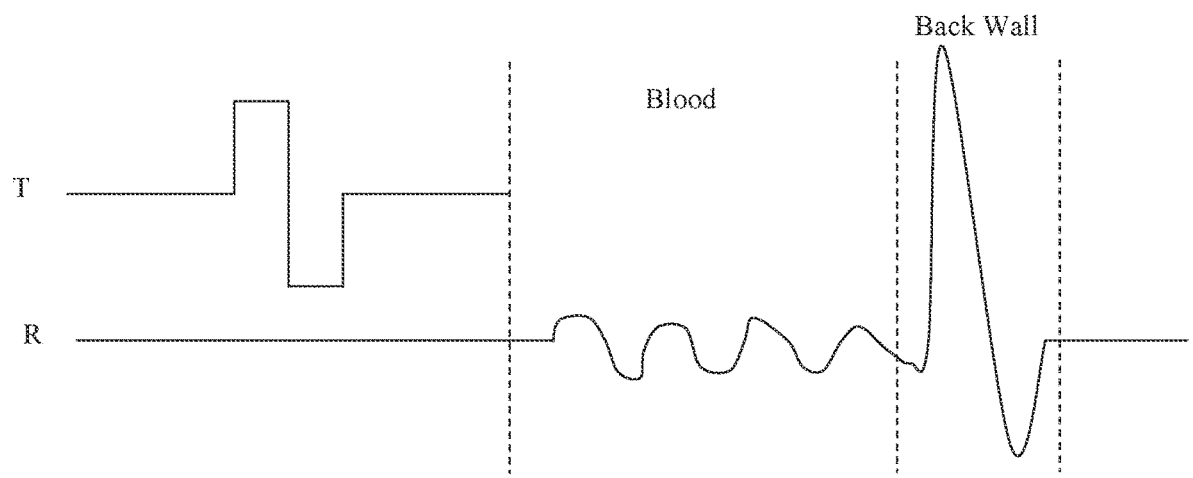
FIG. 25 is a plot of a short pulse and response during calibration of the system of FIG. 19.

Use of the calibration acquisition process facilitates collection of oxygen transport parameters such as HCT. As shown in FIG. 25, shorter pulses are generated during calibration resulting in a delayed response compared to the echoes returned by the blood. This may be due to the further distance of the back wall of the sample container, for example. The system or device is configured to measure, including amplitude and time, from both the blood and the back wall of the container. HCT can be determined using a linear model wherein:

$$HCT = \alpha + \beta_{AMP} + \gamma_{TIME}$$

Alpha ($\alpha$) is a fixed constant. Beta ($\beta_{AMP}$) is related to the amplitude and gamma ($\gamma_{TIME}$) is related to the time duration of the return signal based on its arrival time.

Figure 29:
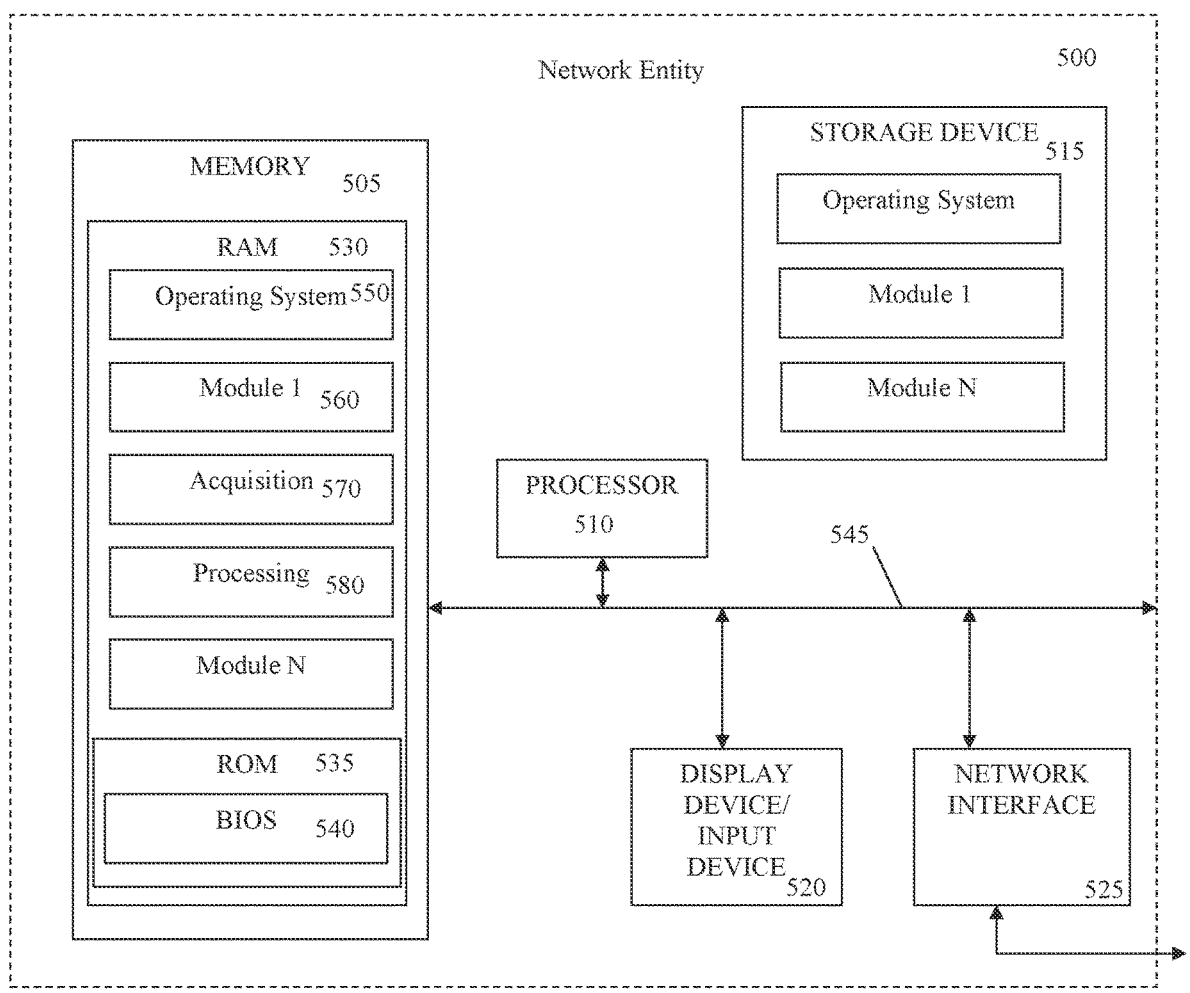
FIG. 29 is a network entity for characterizing soft tissue parameters.

Referring now to FIG. 29, a schematic diagram of a central server 500, or similar network entity, configured to implement a system or process disclosed herein is provided. As used herein, the designation "central" merely serves to describe the common functionality the server provides for multiple clients or other computing devices and does not require or infer any centralized positioning of the server relative to other computing devices.

As may be understood from FIG. 19, in this embodiment, the central server 500 may include a processor 510 that communicates with other elements within the central server 500 via a system interface or bus 545. Also included in the central server 500 may be a display device/input device 520 for receiving and displaying data. This display device/input device 520 may be, for example, a keyboard or pointing device that is used in combination with a monitor. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide nonvolatile storage for a central server. It is important to note that the computer-readable media described above could be replaced by any other type of computer-readable media known in the art. Such media include, for example, magnetic cassettes, flash memory cards and digital video disks.

A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may perform the functions described above and illustrated by the figures, such as FIGS. 19, 27 and 28, and other materials disclosed herein. The modules may include, for example, an acquisition module 570 and a processing module 580 for performing the operations described in reference to FIG. 19.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. An apparatus comprising:
  a cartridge;
  a plurality of transducers each configured to detect one or more responses resulting from one or more measurement signals applied into the cartridge having a plurality of blood samples from a subject, wherein the plurality of transducers include i) one or more transducers associated with a first test chamber and ii) a transducer associated with a second test chamber, wherein the one or more transducers associated with the first test chamber is configured to detect i) a first measurement signal associated with detection of a first set of hemostasis parameters and ii) a third measurement signal associated with detection of an oxygen transport parameter, and wherein the transducer associated with the second test chamber is configured to detect a second measurement signal associated with a second set of hemostasis parameters;
  a receptacle configured to receive the cartridge, wherein the cartridge comprises a plurality of test chambers each defined by a cartridge housing, the plurality of test chambers including the first test chamber and the second test chamber, wherein the cartridge comprises a fluid pathway comprising a plurality of channels, each defined at least in part by the cartridge housing, wherein the fluid pathway includes an inlet, defined at least in part by the cartridge housing, through which a blood sample is directed into the cartridge through application of a pressure differential applied through the receptacle, wherein at least one channel of the fluid pathway is in communication with the inlet and the plurality of test chambers;
a graphical user interface;
a processor coupled to the plurality of transducers and the graphical user interface; and
a non-transitory memory in communication with the processor, the non-transitory memory comprising computer-executable instructions, wherein execution of the instructions, cause the processor to:
receive the one or more responses associated with the first, second, and third measurement signals; and
determine the first set and second set of hemostasis parameters by evaluating an assessed displacement of the blood sample associated with the respective first and second measurement signals for a viscoelastic response of the blood sample in the respective first and second chambers, wherein each first and second sets of hemostasis parameters includes i) a parameter associated with clot stiffness and ii) a parameter selected from the group consisting of clot time, clot formation rate, and lysis time for each of the respective first and second chambers;
determine the oxygen transport parameter by evaluating the one or more responses associated with the third measurement signal, wherein the oxygen transport parameter includes a parameter selected from the group consisting of hematocrit and hemoglobin concentration; and
present, via the graphical user interface, the determined oxygen transport parameter and the first and second sets of hemostasis parameters, wherein the presented oxygen transport and first and second sets of hemostasis parameters are used to guide a transfusion and/or introduction of fresh frozen plasma, platelet concentrates, cryoprecipitate, antifibrinolytics, packed red blood cells, and drugs to address assessed deficiencies in hemostasis.

2. The apparatus of claim 1, wherein the blood sample is an in-vitro blood sample.

3. The apparatus of claim 1, wherein the one or more transducers comprise an ultrasound transducer.

4. The apparatus of claim 3, wherein, execution of the instructions, cause the processor to determine the oxygen transport parameter based on an associated speed of the third measurement signal through the blood sample of the first test chamber.

5. The apparatus of claim 3, wherein, execution of the instructions, cause the processor to determine the oxygen transport parameter based on attenuation of the third measurement signal through the blood sample of the first test chamber.

6. The apparatus of claim 3, wherein, execution of the instructions, cause the processor to determine the oxygen transport parameter based on backscatter of the third measurement signal through the blood sample of the first test chamber.

7. The apparatus of claim 1, wherein the processor is further configured to use the oxygen transport parameter to calibrate the apparatus, wherein the oxygen transport parameter is determined (i) based on attenuation of the third measurement signal through the blood sample of the first test chamber, (ii) based on an associated speed of the third measurement signal through the blood sample of the first test chamber, or (iii) based on backscatter of the third measurement signal through the blood sample of the first test chamber.

8. The apparatus of claim 7, wherein the processor is configured to recalibrate the determination of the hemostasis parameter using the oxygen transport parameter.

9. The apparatus of claim 1, further comprising:
a heater configured to heat the blood samples of the first and second test chambers.

10. The apparatus of claim 1, wherein the one or more transducers comprise a first transducer and a second transducer.

11. The apparatus of claim 10, wherein the first transducer is configured to sense the first measurement signal by at least one of optical coherence tomography, focused light interferometer, and laser Doppler techniques.

12. The apparatus of claim 10, wherein the first transducer is configured to sense the first measurement signal by at least one of thromboelastography (TEG) and rotational thromboelastometry (ROTEM) techniques.

13. The apparatus of claim 1, wherein the one or more transducers comprise a single transducer.

14. A method comprising:
providing a cartridge;
providing a plurality of transducers of a system, wherein each of the plurality of transducers is configured to detect one or more responses resulting from one or more measurement signals applied into the cartridge having a plurality of blood samples from a subject, wherein the plurality of transducers include i) one or more transducers associated with a first test chamber and ii) a transducer associated with a second test chamber, wherein the one or more transducers associated with the first test chamber is configured to detect i) a first measurement signal associated with detection of a first set of hemostasis parameters and ii) a third measurement signal associated with detection of an oxygen transport parameter, and wherein the transducer associated with the second test chamber is configured to detect a second measurement signal associated with a second set of hemostasis parameters,
detecting the one or more responses resulting from the one or more measurement signals applied into the cartridge;
receiving the cartridge at a receptacle of the system, wherein the cartridge comprises a plurality of test chambers each defined by a cartridge housing, the plurality of test chambers including the first test chamber and the second test chamber, wherein the cartridge comprises a fluid pathway comprising a plurality of channels, each defined at least in part by the cartridge housing, wherein the fluid pathway includes an inlet, defined at least in part by the cartridge housing, through which a blood sample is directed into the cartridge through application of a pressure differential applied through the receptacle, wherein at least one channel of the fluid pathway is in communication with the inlet and the plurality of test chambers;
receiving, by a processor, the one or more responses associated with the first, second, and third measurement signals; and
determining, by the processor, the first set and second sets of hemostasis parameters by evaluating an assessed displacement of the blood sample associated with the respective first and second measurement signals for a viscoelastic response of the blood sample in the respective first and second chambers, wherein each first and second sets of hemostasis parameters includes i) a parameter associated with clot stiffness and ii) a parameter selected from the group consisting of clot time, clot formation rate, and lysis time for each of the respective first and second chambers;

determining, by the processor, the oxygen transport parameter by evaluating the one or more responses associated with the third measurement signal, wherein the oxygen transport parameter includes a parameter selected from the group consisting of hematocrit and hemoglobin concentration; and presenting, via a graphical user interface of the system, the determined oxygen transport parameter and the first and second sets of hemostasis parameters, wherein the presented oxygen transport and first and second sets of hemostasis parameters are used to guide a transfusion and/or introduction of fresh frozen plasma, platelet concentrates, cryoprecipitate, antifibrinolytics, packed red blood cells, and drugs to address assessed deficiencies in hemostasis.

15. The method of claim 14, wherein the one or more transducers comprise an ultrasound transducer.

16. The method of claim 14, wherein the oxygen transport parameter is determined based on an associated speed of the third measurement signal through the blood sample of the first test chamber.

17. The method of claim 15, wherein the oxygen transport parameter is determined based on an attenuation of the third measurement signal through the blood sample of the first test chamber.

18. The method of claim 15, the oxygen transport parameter is determined based on a backscatter of the third measurement signal through the blood sample of the first test chamber.

* * * * *